(12) United States Patent
Brönstrup et al.

(10) Patent No.: US 11,331,371 B2
(45) Date of Patent: May 17, 2022

(54) LABYRINTHOPEPTINS AS ANTI-VIRAL AGENTS

(71) Applicants: Helmholtz-Zentrum Für Infektionsforschung GMBH, Braunschweig (DE); Medizinische Hochschule Hannover, Hannover (DE); Twincore, Zentrum Für Experimentelle und Klinische Infektionsforschung GMBH, Hannover (DE)

(72) Inventors: Mark Brönstrup, Braunschweig (DE); Hans-Peter Prochnow, Braunschweig (DE); N.V. Suryanarayana Birudukota, Braunschweig (DE); Thomas Schulz, Hannover (DE); Martin Messerle, Hannover (DE); Thomas Pietschmann, Hannover (DE); Sibylle Haid, Hannover (DE); Sebastian Blockus, Hamburg (DE); Christine Laqmani-Goffinet, Berlin-Steglitz (DE); Sergej Franz, Hannover (DE); Dominic Howard Banda, Ghent (BE)

(73) Assignees: Helmholtz-Zentrum Für Infektionsforschung GMBH, Braunschweig (DE); Medizinische Hochschule Hannover, Hannover (DE); Twincore Zentrum Für Experimentelle und Klinische Infektionsforschung GMBH, Hannover (DE)

( * ) Notice: Subject to any disclaimer, the term of this patent is extended or adjusted under 35 U.S.C. 154(b) by 63 days.

(21) Appl. No.: 16/665,956

(22) Filed: Oct. 28, 2019

(65) Prior Publication Data
US 2020/0093888 A1 Mar. 26, 2020

Related U.S. Application Data

(62) Division of application No. 15/776,522, filed as application No. PCT/EP2016/078143 on Nov. 18, 2016, now abandoned.

(30) Foreign Application Priority Data

Nov. 18, 2015 (EP) ..................................... 15195244
Mar. 30, 2016 (EP) ..................................... 16162805

(51) Int. Cl.
| | |
|---|---|
| *A61K 38/16* | (2006.01) |
| *C07K 7/08* | (2006.01) |
| *C07K 14/36* | (2006.01) |
| *A61P 31/22* | (2006.01) |
| *A61P 31/14* | (2006.01) |
| *A61K 38/00* | (2006.01) |

(52) U.S. Cl.
CPC ............ *A61K 38/164* (2013.01); *A61P 31/14* (2018.01); *A61P 31/22* (2018.01); *C07K 7/08* (2013.01); *C07K 14/36* (2013.01); *A61K 38/00* (2013.01); *Y02A 50/30* (2018.01)

(58) Field of Classification Search
CPC ........ A61K 38/00; A61K 38/164; C07K 7/08; C07K 14/36; A61P 31/14; A61P 31/22; Y02A 50/30
See application file for complete search history.

(56) References Cited

FOREIGN PATENT DOCUMENTS

| WO | 2010058238 A1 | 5/2010 |
|---|---|---|
| WO | 2014009763 A1 | 1/2014 |

OTHER PUBLICATIONS

Drumm et al, Genetic Variation and Clinical Heterogeneity in Cystic Fibrosis, Annu. Rev. Pathol. Mech. Dis., 2012, 7, pp. 267-282.*
Yampolsky et al, The Exchangeability of Amino Acids in Proteins, Genetics, 2005, 170, pp. 1459-1472.*
Byrd et al, A Novel Inhibitor of Dengue Virus Replication That Targets the Capsid Protein, Antimicrobial Agents and Chemotherapy, 2013, 57, pp. 15-25.*

(Continued)

*Primary Examiner* — Li N Komatsu
(74) *Attorney, Agent, or Firm* — Michele M. Wales; InHouse Patent Counsel, LLC

(57) ABSTRACT

The present invention relates to novel labyrinthopeptin derivatives. These labyrinthopeptin derivatives are useful for the treatment of infectious diseases, such as an infectious disease caused by an infection with human respiratory syncytial virus (RSV), Kaposi sarcoma-associated herpesvirus (KSHV), cytomegalovirus (CMV/HCMV), dengue virus (DENV), chikungunya virus (CHIKV), tick-borne encephalitis virus (TBEV; FSME virus), vesicular stomatitis Indiana virus (VSV), zika virus (ZIKV) and/or hepatitis C virus (HCV). Said labyrinthopeptin derivatives are also useful for analyzing the mode of action of labyrinthopeptins. Also encompassed by the present invention are labyrinthopeptins for use in treating an infectious disease, in particular an infectious disease caused by an infection with any one of the viruses selected from RSV, KSHV, CMV, CHIKV, TBEV, VSV, ZIKV and HCV. The invention further relates to a combination of labyrinthopeptin A1 and A2 for use as a medicament, e.g. for treating an infectious disease caused by an infection with RSV, KSHV, CMV, DENV, CHIKV, TBEV, VSV, ZIKV and/or HCV.

Figure 5:
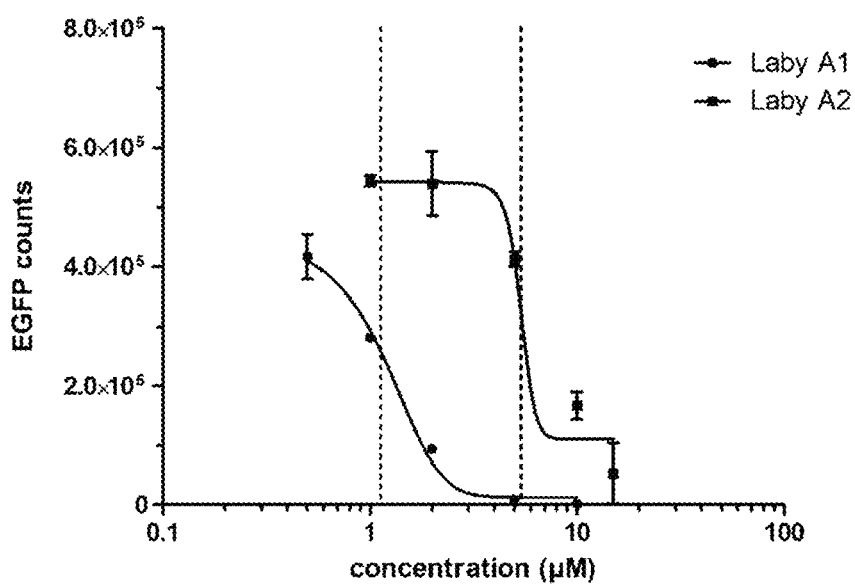

13 Claims, 18 Drawing Sheets
Specification includes a Sequence Listing.

(56) References Cited

OTHER PUBLICATIONS

Cianci et al, Orally Active Fusion Inhibitor of Respiratory Syncytial Virus, Antimicrobial Agents and Chemotherapy, 2004, 48, pp. 413-422.*
Gordts et al., Labyrinthopeptin A1, a unique lantibiotic peptide with broad-spectrum antiviral (HIV, HSV, influenza, RSV and DENV) activity, Journal of Virus Eradication, 2016, 2, p. 26.*
Krawczyk et al., Heterologous Expression and Engineering Studies of Labyrinthopeptins, Class III Lantibiotics from Actinomadura namibiensis, Chemistry & Biology, 2013, 20, pp. 111-122.*
Peppas et al, Hydrogels for oral delivery of therapeutic proteins, Expert Opin. Biol. Ther., 2004, 4, pp. 1-7.*
Alen et al., "52. Labyrinthopeptins, a New Class of Lantibiotics, Exhibit Potent Anti-Dengue Virus Activity", Program and Abstracts of the Twenty-Fifth International Conference on Antiviral Research (ICAR), Retrived from the internet http://c.ymcdn.com/sites/www.isar-icar.com/resource/resmgr/docs/final_program_2012.pdf, (2012).
EPO Office Action dated May 22, 2019 received in corresponding EP Application 16 809 653.5.
Escano et al., "Multipronged Approach for Engineering Novel Peptide Analogues of Existing Lantibiotics", Expert Opinion on Drug Discovery, vol. 10, No. 8, pp. 857-870, (2015).

Férir et al., "The Lantibiotic Peptide Labyrinthopeptin A1 Demonstrates Broad Anti-HIV and Anti-HSV Activity with Potential for Microbicidal Applications", Plos One, vol. 8, No. 5, pp. 1-16, (2013).
Martinez et al., "Antiviral Drug Discovery: Broad-Spectrum Drugs from Nature", Natural Product Reports, vol. 32, No. 1, pp. 29-48, (2015).
Meindl et al supporting information, from https://onlinelibrary.wiley.com/action/downloadSupplement?doi=10.1002%2Fanie.200905773&file=anie_200905773_sm_miscellaneous_information.pdf, 2010, pp. 1-19.
Meindl et al., "Labyrinthopeptins: A New Class of Carbacyclic Lantibiotics", Angewandte Chemie International Edition, vol. 49, No. 6, pp. 1151-1154, (2010).
Oeyen et al., "Labyrinthopeptin A1 Exerts Broad-Spectrum Antiviral Activity against Dengueand Zika Virus", Program and Abstracts of the 3st International Conference on Antiviral Research (ICAR), Retrieved from the internet: https://www.isar-icar.com/resources/Documents/icar_2018program_final.pdf, (2018).
Water, from http://www.biology-online.org/dictionary/Water, pp. 1-3, accessed Apr. 24, 2014.
Written Opinion and International Search Report dated Apr. 26, 2017 in PCT/EP2016/078143.

* cited by examiner

Figure 1. Chemical structure of (A) lanthionin and (B) labionin
A
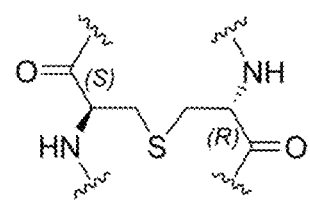
meso-Lanthionin
(Lan)
B
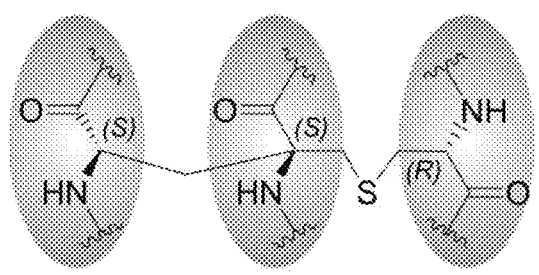
Labionin
(Lab)
Figure 2. Chemical structure of dehydrobutyrine
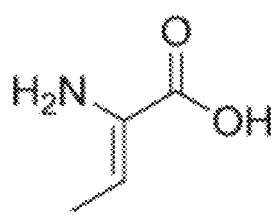

Figure 3. Chemical structure of LabyA1 and LabyA2 showing their stereochemistry
A Laby A1
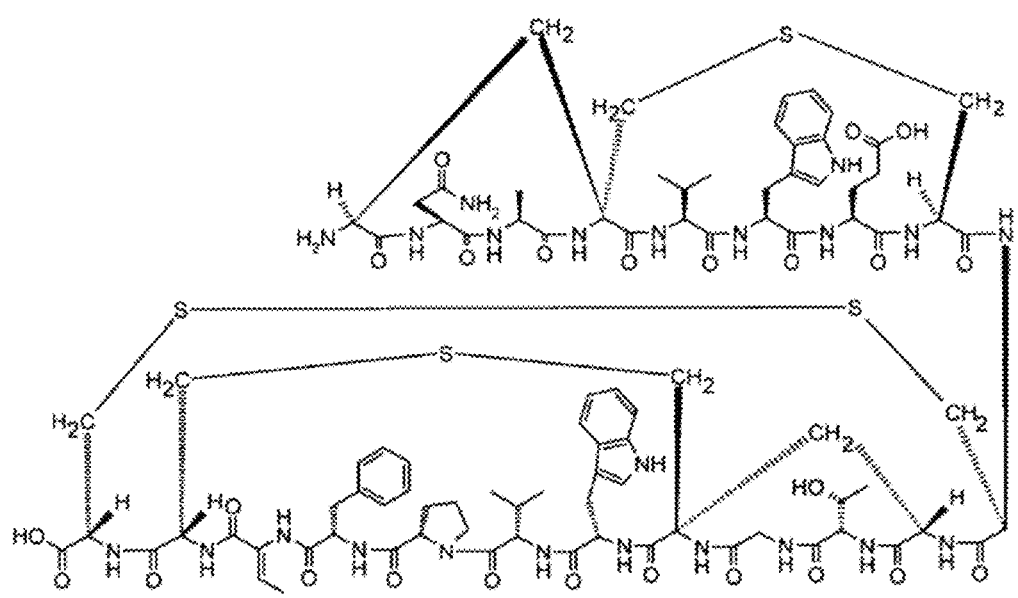
B LabyA2
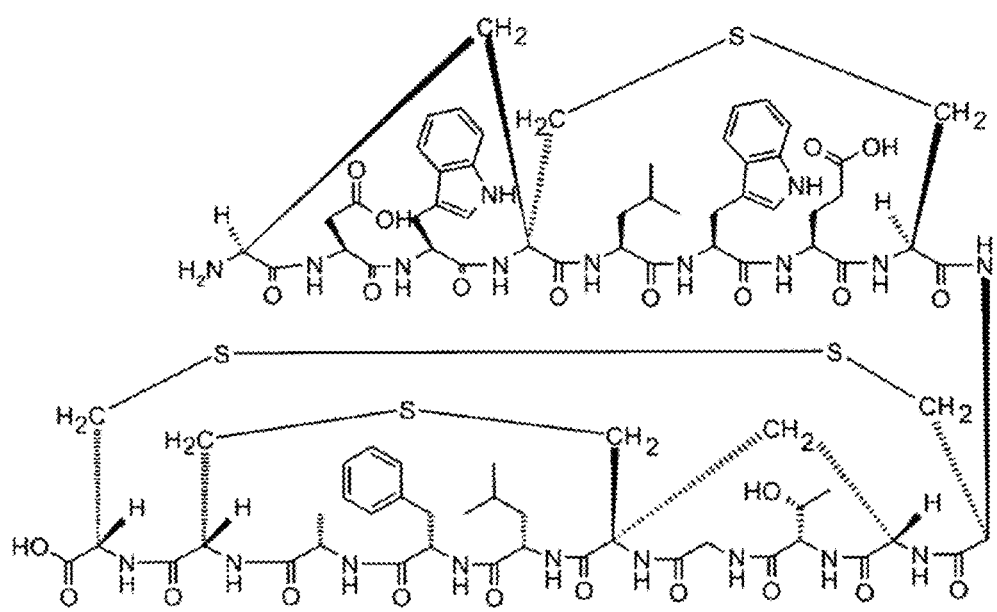

Figure 4. Chemical structures of LabyA1, LabyA2, LabyA1-Hexyn and LabyA2-Hexyn
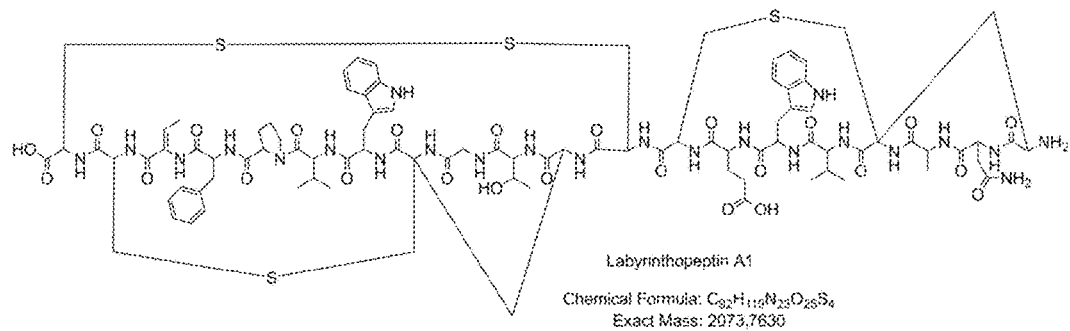
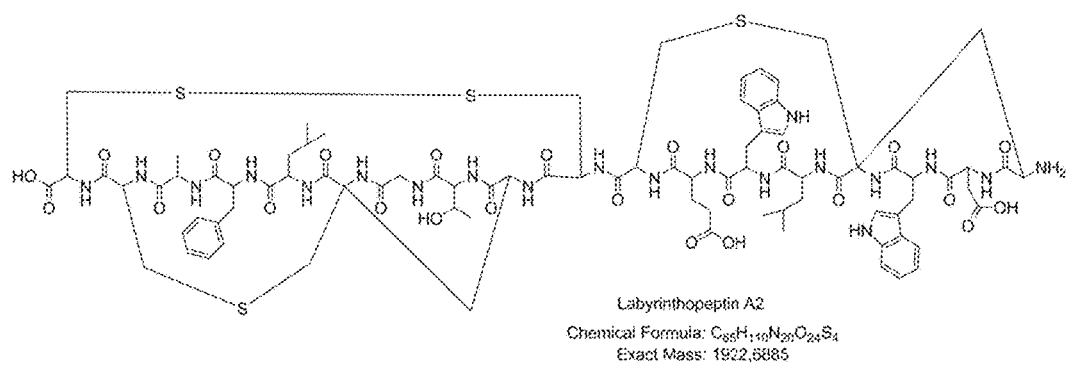
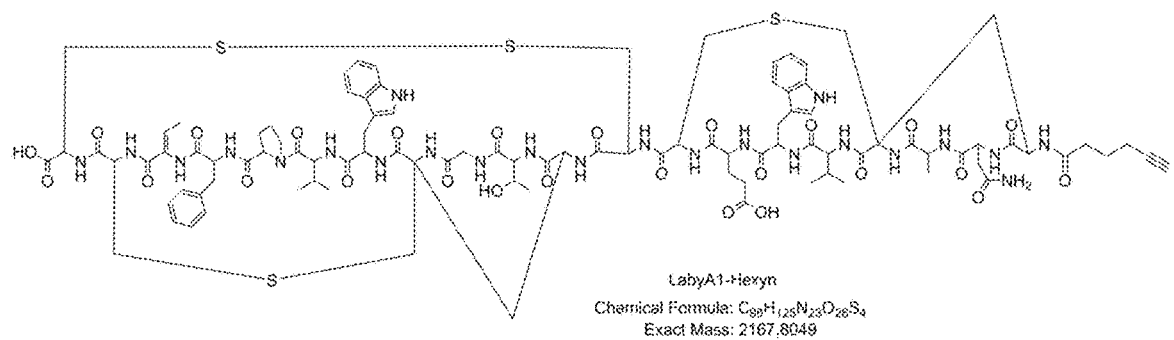
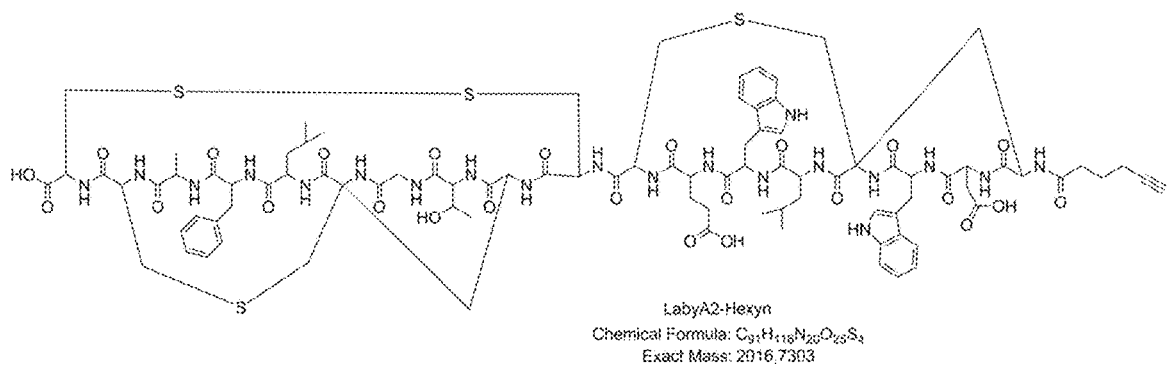

Figure 7.
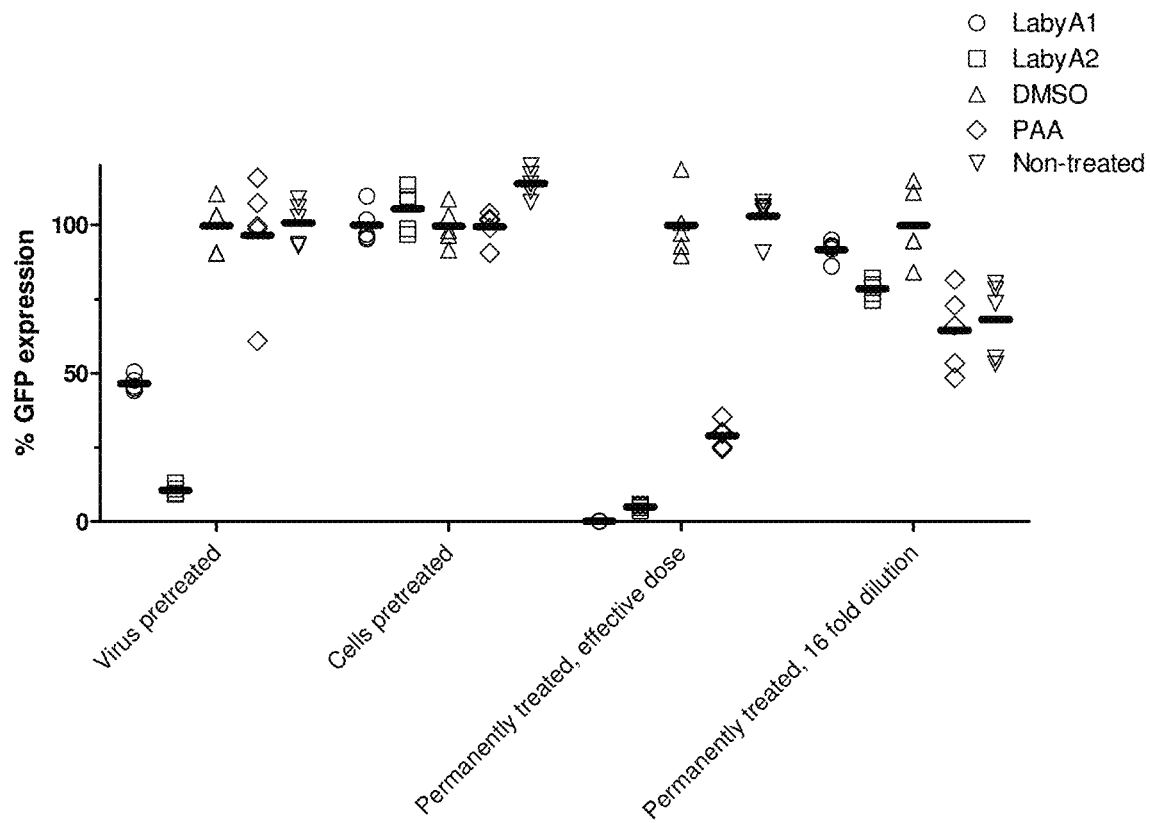
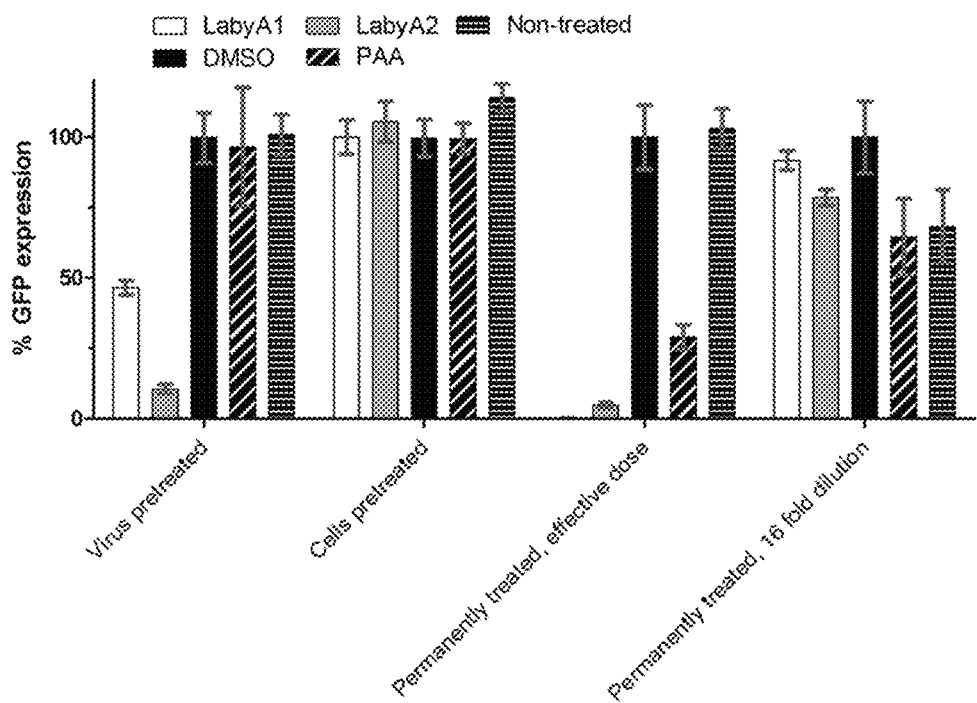

MOI =3 ; incubation time: 72 h

Figure 16:
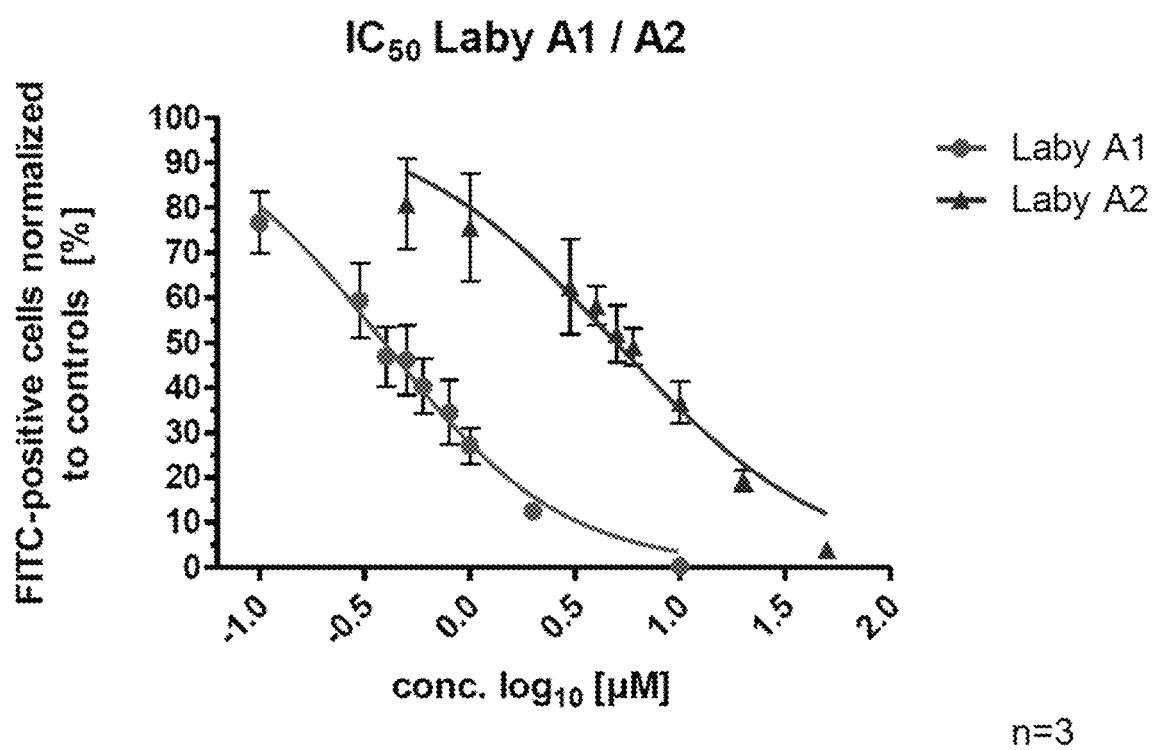

Figure 16.
A
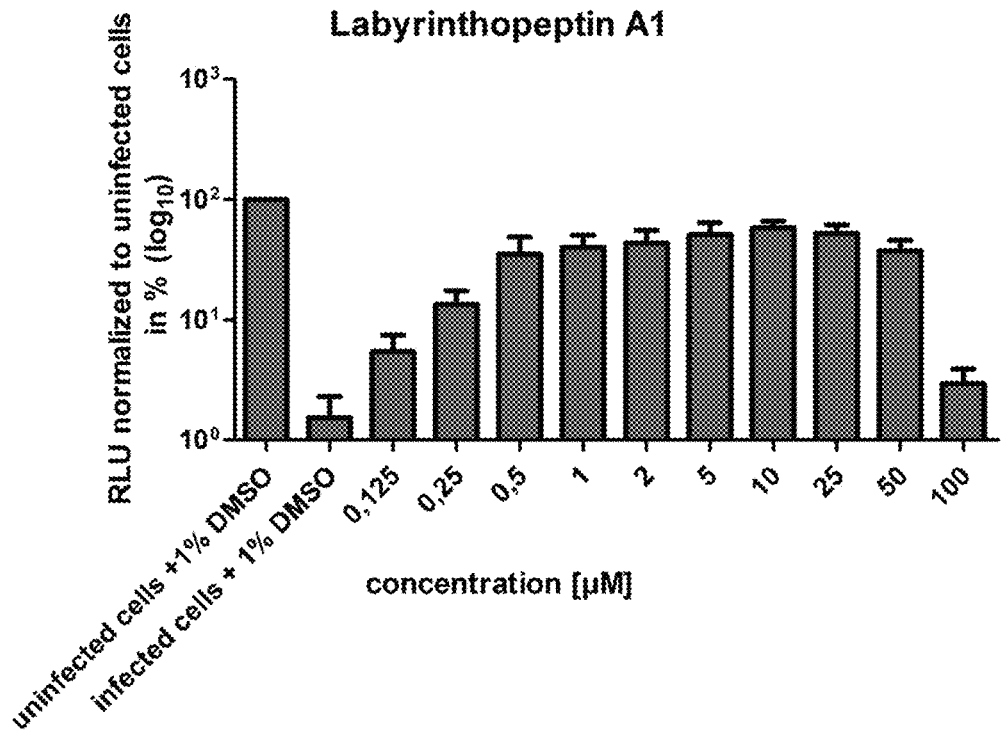
B
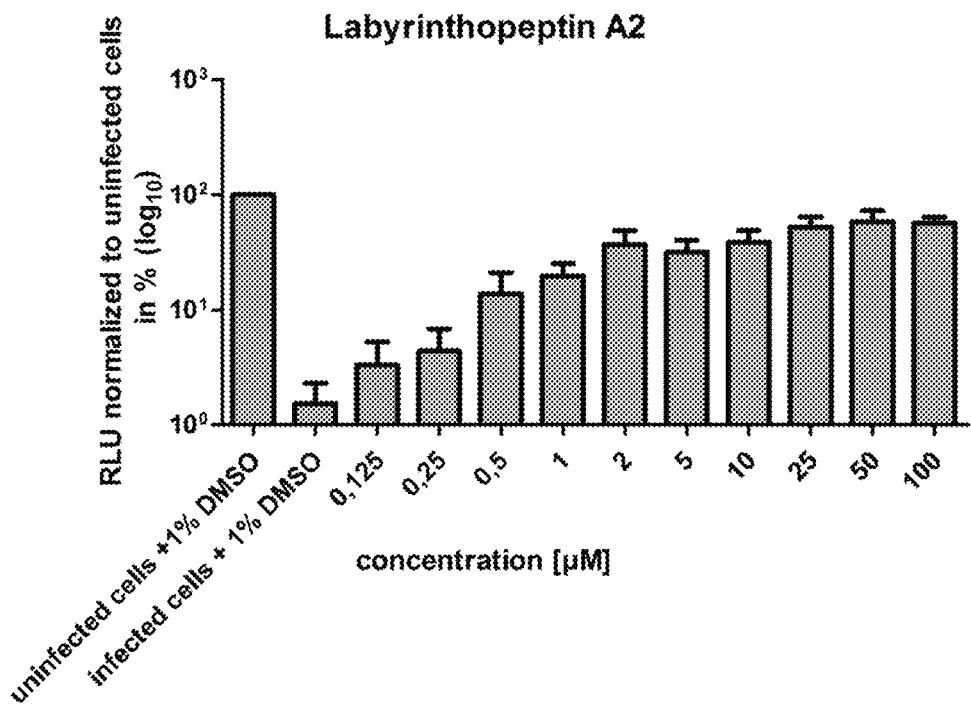

C n=3

A1:
IC$_{50}$= 0.39 µM

A2:
IC$_{50}$= 4.97 µM

A $EC_{50}$: HIV → 0.7 – 3.3 µM
     HSV → 0.29 – 2.8 µM
Férir et al. 2013 (PLoS One, 8(5):e64010)
$EC_{50}$: VSV-G → 1,1 – 3,7 µM
     CHIKV → 0.5 – 1.7 µM B
Labyrinthopeptin A1

Lab = Labionin

A

IC50 = 1.05 μM

IC90 = 9.163 μM

CC90 could not be determined

B

IC50 = 1.728 µM
IC90 = 24.9 µM
CC90 could not be determined

A1:
CC$_{50}$= 79.70 µM

SEQUENCE LISTING

```
<160> NUMBER OF SEQ ID NOS: 8

<210> SEQ ID NO 1
<211> LENGTH: 20
<212> TYPE: PRT
<213> ORGANISM: Artificial Sequence
<220> FEATURE:
<223> OTHER INFORMATION: Labyrinthopeptin derivative
<220> FEATURE:
<221> NAME/KEY: VARIANT
<222> LOCATION: (1)..(1)
<223> OTHER INFORMATION: Xaa is labionin
<220> FEATURE:
<221> NAME/KEY: VARIANT
<222> LOCATION: (2)..(2)
<223> OTHER INFORMATION: Xaa is Asn, Asp or Glu
<220> FEATURE:
<221> NAME/KEY: VARIANT
<222> LOCATION: (3)..(3)
<223> OTHER INFORMATION: Xaa is Ala, Trp or Ser
<220> FEATURE:
<221> NAME/KEY: VARIANT
<222> LOCATION: (4)..(4)
<223> OTHER INFORMATION: Xaa is labionin
<220> FEATURE:
<221> NAME/KEY: VARIANT
<222> LOCATION: (5)..(5)
<223> OTHER INFORMATION: Xaa is Val, Leu or Ile
<220> FEATURE:
<221> NAME/KEY: VARIANT
<222> LOCATION: (6)..(6)
<223> OTHER INFORMATION: Xaa is Trp or Tyr
<220> FEATURE:
<221> NAME/KEY: VARIANT
<222> LOCATION: (7)..(7)
<223> OTHER INFORMATION: Xaa is Glu or Asp
<220> FEATURE:
<221> NAME/KEY: VARIANT
<222> LOCATION: (8)..(8)
<223> OTHER INFORMATION: Xaa is labionin
<220> FEATURE:
```

```
<221> NAME/KEY: VARIANT
<222> LOCATION: (10)..(10)
<223> OTHER INFORMATION: Xaa is labionin
<220> FEATURE:
<221> NAME/KEY: VARIANT
<222> LOCATION: (11)..(11)
<223> OTHER INFORMATION: Xaa is Thr or Ser
<220> FEATURE:
<221> NAME/KEY: VARIANT
<222> LOCATION: (12)..(12)
<223> OTHER INFORMATION: Xaa is Gly or Pro
<220> FEATURE:
<221> NAME/KEY: VARIANT
<222> LOCATION: (13)..(13)
<223> OTHER INFORMATION: Xaa is labionin
<220> FEATURE:
<221> NAME/KEY: VARIANT
<222> LOCATION: (14)..(14)
<223> OTHER INFORMATION: Xaa is absent, Trp or Tyr
<220> FEATURE:
<221> NAME/KEY: VARIANT
<222> LOCATION: (15)..(15)
<223> OTHER INFORMATION: Xaa is Val, Leu or Ile
<220> FEATURE:
<221> NAME/KEY: VARIANT
<222> LOCATION: (16)..(16)
<223> OTHER INFORMATION: Xaa is absent, Pro or Gly
<220> FEATURE:
<221> NAME/KEY: VARIANT
<222> LOCATION: (17)..(17)
<223> OTHER INFORMATION: Xaa is Phe, Met, Leu or Tyr
<220> FEATURE:
<221> NAME/KEY: VARIANT
<222> LOCATION: (18)..(18)
<223> OTHER INFORMATION: Xaa is dehdrobutyrine, Ala Thr, Asn or Ser
<220> FEATURE:
<221> NAME/KEY: VARIANT
<222> LOCATION: (19)..(19)
<223> OTHER INFORMATION: Xaa is labionin

<400> SEQUENCE: 1

Xaa Xaa Xaa Xaa Xaa Xaa Xaa Xaa Cys Xaa Xaa Xaa Xaa Xaa Xaa Xaa
1               5                   10                  15

Xaa Xaa Xaa Cys
            20

<210> SEQ ID NO 2
<211> LENGTH: 20
<212> TYPE: PRT
<213> ORGANISM: Artificial Sequence
<220> FEATURE:
<223> OTHER INFORMATION: Labyrinthopeptin
<220> FEATURE:
<221> NAME/KEY: VARIANT
<222> LOCATION: (1)..(1)
<223> OTHER INFORMATION: Xaa is labionin
<220> FEATURE:
<221> NAME/KEY: VARIANT
<222> LOCATION: (2)..(2)
<223> OTHER INFORMATION: Xaa is Asn, Asp or Glu
<220> FEATURE:
<221> NAME/KEY: VARIANT
<222> LOCATION: (3)..(3)
<223> OTHER INFORMATION: Xaa is Asn, Trp or Ser
<220> FEATURE:
<221> NAME/KEY: VARIANT
<222> LOCATION: (4)..(4)
<223> OTHER INFORMATION: Xaa is labionin
<220> FEATURE:
<221> NAME/KEY: VARIANT
<222> LOCATION: (5)..(5)
<223> OTHER INFORMATION: Xaa is Val, Leu or Ile
<220> FEATURE:
<221> NAME/KEY: VARIANT
<222> LOCATION: (6)..(6)
<223> OTHER INFORMATION: Xaa is Trp or Tyr
```

```
<220> FEATURE:
<221> NAME/KEY: VARIANT
<222> LOCATION: (7)..(7)
<223> OTHER INFORMATION: Xaa is Glu or Asp
<220> FEATURE:
<221> NAME/KEY: VARIANT
<222> LOCATION: (8)..(8)
<223> OTHER INFORMATION: Xaa is labionin
<220> FEATURE:
<221> NAME/KEY: VARIANT
<222> LOCATION: (10)..(10)
<223> OTHER INFORMATION: Xaa is labionin
<220> FEATURE:
<221> NAME/KEY: VARIANT
<222> LOCATION: (11)..(11)
<223> OTHER INFORMATION: Xaa is Thr or Ser
<220> FEATURE:
<221> NAME/KEY: VARIANT
<222> LOCATION: (12)..(12)
<223> OTHER INFORMATION: Xaa is Gly or Pro
<220> FEATURE:
<221> NAME/KEY: VARIANT
<222> LOCATION: (13)..(13)
<223> OTHER INFORMATION: Xaa is labionin
<220> FEATURE:
<221> NAME/KEY: VARIANT
<222> LOCATION: (14)..(14)
<223> OTHER INFORMATION: Xaa is absent, Trp or Tyr
<220> FEATURE:
<221> NAME/KEY: VARIANT
<222> LOCATION: (15)..(15)
<223> OTHER INFORMATION: Xaa is Val, Leu or Ile
<220> FEATURE:
<221> NAME/KEY: VARIANT
<222> LOCATION: (16)..(16)
<223> OTHER INFORMATION: Xaa is Pro or Gly
<220> FEATURE:
<221> NAME/KEY: VARIANT
<222> LOCATION: (17)..(17)
<223> OTHER INFORMATION: Xaa is Phe, Met, Leu or Tyr
<220> FEATURE:
<221> NAME/KEY: VARIANT
<222> LOCATION: (18)..(18)
<223> OTHER INFORMATION: Xaa is dehdrobutyrine, Ala, Thr, Asn or Ser
<220> FEATURE:
<221> NAME/KEY: VARIANT
<222> LOCATION: (19)..(19)
<223> OTHER INFORMATION: Xaa is labionin

<400> SEQUENCE: 2

Xaa Xaa Xaa Xaa Xaa Xaa Xaa Xaa Cys Xaa Xaa Xaa Xaa Xaa Xaa Xaa
1               5                   10                  15

Xaa Xaa Xaa Cys
            20

<210> SEQ ID NO 3
<211> LENGTH: 20
<212> TYPE: PRT
<213> ORGANISM: Artificial Sequence
<220> FEATURE:
<223> OTHER INFORMATION: Labyrinthopeptin
<220> FEATURE:
<221> NAME/KEY: VARIANT
<222> LOCATION: (1)..(1)
<223> OTHER INFORMATION: Xaa is labionin
<220> FEATURE:
<221> NAME/KEY: VARIANT
<222> LOCATION: (4)..(4)
<223> OTHER INFORMATION: Xaa is labionin
<220> FEATURE:
<221> NAME/KEY: VARIANT
<222> LOCATION: (8)..(8)
<223> OTHER INFORMATION: Xaa is labionin
<220> FEATURE:
<221> NAME/KEY: VARIANT
<222> LOCATION: (10)..(10)
```

```
<223> OTHER INFORMATION: Xaa is labionin
<220> FEATURE:
<221> NAME/KEY: VARIANT
<222> LOCATION: (13)..(13)
<223> OTHER INFORMATION: Xaa is labionin
<220> FEATURE:
<221> NAME/KEY: VARIANT
<222> LOCATION: (18)..(18)
<223> OTHER INFORMATION: Xaa is dehydrobutyrine
<220> FEATURE:
<221> NAME/KEY: VARIANT
<222> LOCATION: (19)..(19)
<223> OTHER INFORMATION: Xaa is labionin

<400> SEQUENCE: 3

Xaa Asn Ala Xaa Val Trp Glu Xaa Cys Xaa Thr Gly Xaa Trp Val Pro
1               5                   10                  15

Phe Xaa Xaa Cys
            20

<210> SEQ ID NO 4
<211> LENGTH: 18
<212> TYPE: PRT
<213> ORGANISM: Artificial Sequence
<220> FEATURE:
<223> OTHER INFORMATION: Labyrinthopeptin
<220> FEATURE:
<221> NAME/KEY: VARIANT
<222> LOCATION: (1)..(1)
<223> OTHER INFORMATION: Xaa is labionin
<220> FEATURE:
<221> NAME/KEY: VARIANT
<222> LOCATION: (4)..(4)
<223> OTHER INFORMATION: Xaa is labionin
<220> FEATURE:
<221> NAME/KEY: VARIANT
<222> LOCATION: (8)..(8)
<223> OTHER INFORMATION: Xaa is labionin
<220> FEATURE:
<221> NAME/KEY: VARIANT
<222> LOCATION: (10)..(10)
<223> OTHER INFORMATION: Xaa is labionin
<220> FEATURE:
<221> NAME/KEY: VARIANT
<222> LOCATION: (13)..(13)
<223> OTHER INFORMATION: Xaa is labionin
<220> FEATURE:
<221> NAME/KEY: VARIANT
<222> LOCATION: (17)..(17)
<223> OTHER INFORMATION: Xaa is labionin

<400> SEQUENCE: 4

Xaa Asp Trp Xaa Leu Trp Glu Xaa Cys Xaa Thr Gly Xaa Leu Phe Ala
1               5                   10                  15

Xaa Cys

<210> SEQ ID NO 5
<211> LENGTH: 20
<212> TYPE: DNA
<213> ORGANISM: Artificial Sequence
<220> FEATURE:
<223> OTHER INFORMATION: RT-Primer

<400> SEQUENCE: 5
ggtttcccag cttctcctgg                                         20

<210> SEQ ID NO 6
<211> LENGTH: 20
<212> TYPE: DNA
<213> ORGANISM: Artificial Sequence
<220> FEATURE:
```

```
<223> OTHER INFORMATION: ZIKV-specific forward primer

<400> SEQUENCE: 6
aaaaacccca tgtggagagg                                              20

<210> SEQ ID NO 7
<211> LENGTH: 20
<212> TYPE: DNA
<213> ORGANISM: Artificial Sequence
<220> FEATURE:
<223> OTHER INFORMATION: ZIKV-specific reverse primer

<400> SEQUENCE: 7
cattccttca gtgtgtcacc                                              20

<210> SEQ ID NO 8
<211> LENGTH: 5
<212> TYPE: PRT
<213> ORGANISM: Artificial Sequence
<220> FEATURE:
<223> OTHER INFORMATION: Partial labyrinthopeptin or laborynthopeptin
      derivative
<220> FEATURE:
<221> NAME/KEY: VARIANT
<222> LOCATION: (5)..(5)
<223> OTHER INFORMATION: Xaa is dehydrobutyrine

<400> SEQUENCE: 8

Trp Val Pro Phe Xaa
1               5
```

LABYRINTHOPEPTINS AS ANTI-VIRAL AGENTS

CROSS-REFERENCE TO RELATED APPLICATIONS

This application is a Divisional Application of U.S. Ser. No. 15/776,522 filed May 16, 2018, now abandoned, which is a § 371 National Stage Application of PCT/EP2016/078143 filed Nov. 18, 2016, which claims priority to EP 15195244.7 filed on Nov. 18, 2015 and EP 16162805.2 filed on Mar. 30, 2016. All of these documents are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Aug. 31, 2018 is named MHH-04-US_ST_25-8-31-18-FINAL.txt and is 6 kilobytes in size.

The present invention relates to novel labyrinthopeptin derivatives. These labyrinthopeptin derivatives are useful for the treatment of infectious diseases, such as an infectious disease caused by an infection with human respiratory syncytial virus (RSV), Kaposi sarcoma-associated herpesvirus (KSHV), cytomegalovirus (CMV), dengue virus (DENV), chikungunya virus (CHIKV), tick-borne encephalitis virus (TBEV; FSME virus), vesicular stomatitis Indiana virus (VSV), zika virus (ZIKV) and/or hepatitis C virus (HCV). Said labyrinthopeptin derivatives are also useful for analyzing the mode of action of labyrinthopeptins. Also encompassed by the present invention are labyrinthopeptins for use in treating an infectious disease, in particular an infectious disease caused by an infection with any one of the viruses selected from RSV, KSHV, CMV, CHIKV, TBEV, VSV, ZIKV and HCV. The invention further relates to a combination of labyrinthopeptin A1 and A2 for use as a medicament, e.g. for treating an infectious disease caused by an infection with RSV, KSHV, CMV, DENV CHIKV, TBEV, VSV, ZIKV and/or HCV.

Lantibiotics are peptides that are ribosomally synthesized from bacteria such as staphylococci, lactobacilli, and actinomycetes. The common structural characteristic of lantibiotics is the noncanonical amino acid lanthionine, which confers conformational stability to the peptide. The labyrinthopeptins are new class of carbacyclic lantibiotics and have been identified in 1988 in *Actinomadura namibiensis* (Drug Discovery from Natural Products, Kap. 3, S. 49ff). They are representatives of a new type of lantibiotics with a unique carbacyclic post-translationally modified amino acid named labionin. The chemical structure of labionin is shown in FIG. 1(B).

The structure of the labyrinthopeptins was published in 2008 (WO2008/040469 and Meindl, 2010, Angew. Chem. Int. Ed. 49, 1151-1154). Labyrinthopeptins, particularly Labyrinthopeptin A1 (also called LabA1 or LabyA1) and Labyrinthopeptin A2 (also called LabA2 or LabyA2) have several interesting biological activities. For example, LabyA2 shows an excellent efficacy against neuropathic pain in the mouse model. LabyA1 was recently shown to inhibit both HIV and HSV at sub-micromolar concentrations in vitro (Férir, 2013, PLOS one, 8(5):e64010). The compound is suggested to block viral entry by interacting with viral envelopes and to prevent cell-to-cell transmission (Meyerhans, 2015, Nat. Prod. Rep., 2015, 32, 29-48). Although LabyA1 is effective against resistant HIV and HSV viruses, it does not cause an inflammatory response in peripheral blood mononuclear cells (PBMCs). Also antiviral activity of LabyA1 against Dengue virus (DENV) has been described (Dominique Schols, HVBD meeting 2013). Identifying the mode of action of labyrinthopeptins may pave the way for the identification of further (infectious) diseases that can be treated with these molecules.

Viral infections are still a global problem, causing several million deaths each year. For example, 1-3% of the population of North America and Europe, and up to 50% of the population in some areas of equatorial Africa has or had an infection with the Kaposi sarcoma-associated herpesvirus (KSHV, also called human herpesvirus 8, HHV8, or KS agent). In addition, it was shown that about 4% of breast cancer patients in Taiwan are KSHV-infected.

Human cytomegalovirus (CMV, also called HCMV) is found throughout all geographic locations and socioeconomic groups, and infects between 60% and 70% of adults in industrialized countries and almost 100% in emerging countries. A CMV infection is typically unnoticed in healthy people, but can be life-threatening for the immunocompromised, such as HIV-infected persons, organ transplant recipients, or newborn infants. After infection, CMV remains latent within the body throughout life and can be reactivated at any time. Eventually, it may cause mucoepidermoid carcinoma and possibly other malignancies such as prostate cancer.

The Dengue virus (DENV) causes a wide range of diseases in humans, from a self limited Dengue Fever (DF) to a life-threatening syndrome called Dengue Hemorrhagic Fever (DHF) or Dengue Shock Syndrome (DSS). There currently is no human vaccine against DENV available.

Furthermore, the Lancet (2015) and the Center for Disease Control and Prevention (CDC) announced that the Human respiratory syncytial virus (RSV, also called hRSV) is a major cause of morbidity and mortality of children under 5 years and represents a major problem in elderly and immunocompromised patients. About 70% of children are infected prior to their first birthday. At the age of 2 years, nearly every child had an RSV infection. The mortality rate is relatively low, however, RSV can be dangerous for children under 2 at risk as well as for older patients. Indeed, according to the CDC, around 14,000 mostly elderly patients died in the US due to an RSV infection in 2014. There is currently no effective treatment for RSV infections of the lower respiratory tract (lower respiratory tract infection, LRTI). There are a few drugs which are approved for seasonal prophylactic treatment of RSV or for the prevention of RSV infection. However, some of these medicaments have significant side effects.

Chikungunya-virus (CHIKV) is a pathogenic RNA virus transmitted via bites by *Aedes* mosquito vectors. It causes fever, polyarthralgia, rash and is usually cleared after a short symptomatic period. However, chronification of symptoms occurs in a subset of symptomatic patients, causing painful and debilitating, inflammatory arthralgia, accompanied by disability, fatigue and depression. Recent and ongoing outbreaks, facilitated by globalization and expanded vector usage have raised scientific and public health attention. There is neither a specific antiviral treatment nor a protective vaccine available.

Tick-borne encephalitis virus (TBEV) is the virus associated with tick-borne encephalitis (TBE). TBE is a viral infectious disease involving the central nervous system. The disease most often manifests as meningitis, encephalitis, or meningoencephalitis. Although TBE is most commonly recognized as a neurological disorder, mild fever can also occur. Long-lasting or permanent neuropsychiatric sequelae are observed in 10 to 20% of infected patients. The number of reported cases has been increasing in most countries. The disease is incurable once manifested, so there is no specific drug therapy for TBE. Symptomatic brain damage requires hospitalization and supportive care based on syndrome severity.

Zika virus (ZIKV) causes Zika fever. Zika virus has a nonsegmented, single-stranded, positive-sense RNA genome and is spread by *Aedes* mosquitoes. Zika virus is related to dengue fever, yellow fever, Japanese encephalitis, and West Nile viruses. Zika fever (also known as Zika virus disease) has often no symptoms, but when present the symptoms are usually mild and can resemble dengue fever. The symptoms may include fever, red eyes, joint pain, headache, and a maculopapular rash. However, infections in pregnant women may also infect the baby and have been linked to miscarriage and microcephaly. There is no effective vaccine against Zika fever.

Vesicular stomatitis Indiana virus (VSV) is a pathogenic RNA-virus that infects insects, cattle, horses and pigs. VSV is zoonotic causing flu-like symptoms in humans. The virus is transferred by insects. There is no specific treatment available.

The hepatitis C virus (HCV) causes hepatitis C which is an infectious disease that primarily affects the liver. The virus persists in the liver in about 75% to 85% of those initially infected. Chronic HCV infection often leads to liver disease and occasionally to cirrhosis. Cirrhosis can be the cause for the development of liver failure, liver cancer, or esophageal and gastric varices. Globally, between 130-150 million people have chronic hepatitis C infection ("Hepatitis C Fact sheet No 164", WHO, July 2015, Retrieved 4 Feb. 2016). At present there is no vaccine against hepatitis C available.

Thus, there is a need for finding further anti-viral drugs, particularly for the treatment and/or prevention of infectious diseases arising from an infection with KSHV, CMV, RSV, DENV, CHIKV, TBEV, VSV, ZIKV and/or HCV. In addition, there is also a need for novel means and methods to unravel the mode of action of labyrinthopeptins.

Thus, the technical problem underlying the present invention is the provision of means and methods for the treatment and/or prevention of viral infections, particularly for the treatment and/or prevention of infections with KSHV, CMV, RSV, DENV, CHIKV, TBEV, VSV, ZIKV and/or HCV; and the provision of means and methods for analyzing the mode of action of labyrinthopeptins.

The technical problem is solved by provision of the embodiments as characterized in the claims.

Accordingly, the present invention relates to a peptide (i.e. a labyrinthopeptin derivative) comprising or consisting of the amino acid sequence (SEQ ID NO: 1)

$$R_1\text{-Lab-}X_1\text{—}X_2\text{-Lab-}X_3\text{—}X_4\text{—}X_5\text{-Lab-Cys-Lab-}X_6\text{—}X_7\text{-Lab-}X_8\text{-Lab-Cys-}R_2$$

with disulfide bridges and CH$_2$ bridges as shown wherein
Lab is labionin
$X_1$ is an amino acid selected from Asn, Asp, and Glu;
$X_2$ is an amino acid selected form Ala, Trp, and Ser;
$X_3$ is an amino acid selected from Val, Leu, and Ile;
$X_4$ is an amino acid selected from Trp and Tyr;
$X_5$ is an amino acid selected from Glu and Asp;
$X_6$ is an amino acid selected from Thr and Ser;
$X_7$ is an amino acid selected from Gly and Pro;
$X_8$ consists of a sequence of 3 to 5 amino acids;
$R_1$ is selected from H, a $(C_2\text{-}C_{12})$alkynyl, a $C(O)\text{—}(C_2\text{-}C_{12})$alkynyl, a $C(O)\text{—}O\text{—}(C_2\text{-}C_{12})$alkynyl, and a $C(O)NH\text{—}(C_2\text{-}C_{12})$alkynyl; wherein $R_1$ carries the alkynyl group at the terminal position; and
$R_2$ is selected from H, a $[C(O)]\text{—}NH\text{—}(C_2\text{-}C_{12})$alkynyl or a $[C(O)]\text{—}O\text{—}(C_2\text{-}C_{12})$alkynyl; wherein the moiety $[C(O)]$ is the carbonyl group of the terminal amino acid; wherein $R_2$ carries the alkynyl group at the terminal position;
wherein if $R_1$ is H, then $R_2$ is not H.

The present invention solves the above identified technical problem since, as documented herein below and in the appended Examples, labyrinthopeptin derivatives that can be further derivatized with compounds such as anti-viral drugs or marker molecules have been obtained. These labyrinthopeptin derivatives enable a more efficient anti-viral treatment (e.g. by linkage to anti-viral drugs) and also enable a more detailed analysis of the mode of action of labyrinthopeptins (e.g. by linkage to marker molecules). As mentioned above, understanding the mode of action of labyrinthopeptins would pave the way to the development of further effective anti-viral drugs.

The labyrinthopeptin derivative of the present invention has anti-viral activity, particularly against RSV, KSHV, CMV, DENV, CHIKV, TBEV, VSV, ZIKV and/or HCV, preferably against DENV.

Assays for testing the anti-viral activity of compounds such as labyrinthopeptins are commonly known in the art. For example, to test for the anti-viral activity of the labyrinthopeptin derivative of the invention, the labyrinthopeptin derivative may be added to cells (e.g. Huh-7.5 cells). Then, the cells may be infected with the virus to be tested (e.g. RSV, KSHV, CMV, DENV, CHIKV, TBEV, VSV, ZIKV and/or HCV, preferably DENV). The amount of virus-positive cells may be evaluated by immunocytochemistry. For example, a primary antibody directed against the virus and a secondary antibody that has a conjugated fluorophore may be applied. The number of total cells may be determined by counting DAPI-stained nuclei. Thus, the percentage of virus-positive cells may be calculated. The obtained result is preferably compared to non-infected cells.

In more detail, to test for the anti-viral activity of labyrinthopeptins, labyrinthopeptin derivatives or combinations of labyrinthopeptins/labyrinthopeptin derivatives, Huh-7.5 cells (e.g. 3×[(10)]^4 per well) may be seeded in black 96-well optical-bottom plates [Nunc] in full growth medium one day prior to infection. After washing with PBS, 40 µl assay medium (5% FBS) may be added to cells containing the labyrinthopeptin of the invention, the labyrinthopeptin derivative of the invention (final conc. 50, 16.7, 5.56, 1.85, 0.62, 0.21, 0.069 µg/ml) or a combination of labyrinthopeptins/labyrinthopeptin derivatives (25, 8.3, 2.8, 0.93, 0.31, 0.10, 0.034 µg/ml each). Treatments are preferably run in doublets. PBS serves as a control. After 30 min of incubation, cells may be infected with the virus, (e.g. RSV, KSHV, CMV, DENV, CHIKV, TBEV, VSV, ZIKV, and/or HCV, preferably DENV, e.g. DENV Type 2 New Guinea C) at an MOI of 0.5 to give a final volume of 60 µl/well. After 2 h incubation at room temperature cells may be washed with PBS and 100 µl assay medium may be added per well. Infected cells may be incubated for another 48 h. Hereafter, media may be removed from the wells and cells may be fixed with 4% PFA. Fixed cells may be washed extensively with PBS and permeabilized with 0.25% TritonX-100 for 5 min. After blocking with 5% FBS in PBS, primary antibody directed against the virus may be applied (e.g. Anti-Dengue Virus E glycoprotein antibody [DE1] (ab41349) [Abcam], 1:100 diluted in 5% FBS/PBS) for 2 h. After washing, secondary antibody (e.g. Alexa Fluor® 488 Goat Anti-Mouse IgG (H+L) [Life Technologies], 1:1000 diluted in 5% FBS/PBS) may be applied for 1 h. Finally, cells may be stained with DAPI (500 ng/ml in PBS) for 5 min.

Fluorescent cells can be analyzed by high-content imaging using the automated microscope ImageXpressMicro [Molecular Devices] and the MetaXpress-software. The excitation wavelengths may be set to 360 nm (DAPI) and 485 nm (Alexa Fluor488) and the emission wavelengths may be set to 460 nm (DAPI) and 516 nm (Alexa Fluor488). Images of six sites/well may be acquired (2 columns, 89 µm spacing; 3 rows, 67 µm spacing). The number of total cells/site may be determined by automatically counting DAPI-stained nuclei. The percentage of virus-positive cells (e.g. DENV-positive cells) may be calculated by automatically evaluating the number of Alexa Fluor 488-positive cells in relation to the total cell number. Values obtained from the six sites may be averaged and plotted onto a semi-logarithmic X/Y-chart. $IC_{50}$-values may be calculated by non-linear regression.

As described above, if in the labyrinthopeptin derivative of the present invention $R_1$ or $R_2$ is an alkynyl, then the alkynyl group is at the terminal position. As described above, $R_1$ may be an urea derivative (i.e. C(O)NH—($C_2$-$C_{12}$)alkynyl) and/or $R_2$ may be an amide (i.e. [C(O)]—NH—($C_2$-$C_{12}$)alkynyl) or an ester (i.e. [C(O)]—O—($C_2$-$C_{12}$)alkynyl). Preferably, $R_2$ is H and $R_1$ carries one of the alkynyl-compounds mentioned above for $R_1$. Thus, preferably, $R_2$ is H and $R_1$ is an alkynyl-compound selected from the group consisting of a ($C_2$-$C_{12}$)alkynyl, a C(O)—($C_2$-$C_{12}$)alkynyl, a C(O)—O—($C_2$-$C_{12}$)alkynyl, and a C(O)NH—($C_2$-$C_{12}$)alkynyl. More preferably, $R_2$ is H and $R_1$ is a C(O)—($C_2$-$C_{12}$)alkynyl. Most preferably, $R_2$ is H and $R_1$ is hex-5ynoyl. As mentioned, if $R_1$ is an alkynyl, then the alkynyl group is at the terminal position.

The labyrinthopeptin derivative of the present invention has a terminal alkyne group (i.e. alkynyl group). Thus, the labyrinthopeptin derivative of the invention may be further derivatized with an azide via dipolar cycloaddition, particularly via "Azide-Alkyne Huisgen Cycloaddition" (Huisgen, 1961, Proceedings of the Chemical Society of London, 357). Thus, the present invention relates to the labyrinthopeptin derivative of the present invention, wherein $R_1$ and/or $R_2$ is/are derivatized with an azide-labeled compound. Said compound may be a compound selected from an anti-viral drug or a marker molecule.

Anti-viral drugs that are linked to the labyrinthopeptin derivative as described above may further enhance the anti-viral activity of the labyrinthopeptin derivative. For example, suitable anti-viral drugs that may be used as compound in the azide-labeled compound are acyclovir penciclovir, Zidovudine, brivudin, cidofovir, HDVD (L-dioxolane uracil analog), Idoxuridin, Famciclovir, Sorivudin, Valaciclovir, Cidofovir, Brincidofovir, Ganciclovir, Valganciclovir, Foscarnet, Maribavir, CMVIG, Letermovir, Leflunomide (antimetabolite, used as a disease-modifying agent in rheumatoid arthritis, has also been successfully used off-label in both CMV disease treatment and prophylaxis), RSV604 (Challa, 2015, Antimicrob Agents Chemother 59(2): 1080-7), ALS-8176 (Challa, 2015, Antimicrob Agents Chemother 59(2): 1080-7), GS-5806 (Gilead®), or a small molecule inhibitor (DeVincenzo, 2014, Proc Natl Acad Sci USA 107(19): 8800-5.). The anti-viral drug may also be NITD-008 or Balapiravir.

By linking a marker molecule to the herein provided labyrinthopeptin derivative (via dipolar cycloaddition) the mode of action of labyrinthopeptins may be analyzed. For example, by linking the labyrinthopeptin derivative to a marker molecule, the location of labyrinthopeptins within the infected cell and/or the interaction between labyrinthopeptins and virus particles may be analyzed. Therefore, imaging methods such as fluorescence microscopy, chemifluorescence microscopy, chemiluminescence microscopy, electron microscopy, nuclear magnetic resonance-based systems or radioisotope-based systems may be used.

Suitable marker molecules that may be used as compound in the azide-labeled compound are described in the following. In particular, herein the terms "marker molecule(s)" or "marker(s)" are used interchangeably and refer to a label or marker that is preferably capable of producing, either directly or indirectly, a detectable signal. For example, the marker molecule may be a radioisotope, a fluorophore or chemiluminescent (chromophore) compound, an enzyme, an imaging agent, a magnetic or paramagnetic label, or a metal ion. The term "marker molecule(s)" includes fluorophores. The term "fluorophore" comprises compounds selected from the group consisting of a dimethylaminocoumarin derivative, preferably 7-dimethylaminocoumarin-4-acetic acid succinimidyl ester, dansyl, 5/6-carboxyfluorescein and tetramethylrhodamine, BODIPY™-493/503, BODIPY™-FL, BODIPY™-TMR, BODIPY™-TMR-X, BODIPY™-TR-X, BODIPY™630/550-X, BODIPY™-650/665-X, Alexa 350, Alexa 488, Alexa 532, Alexa 546, Alexa 555, Alexa 635, Alexa 647, Cyanine 3 (Cy 3), Cyanine 3B (Cy 3B), Cyanine 5 (Cy 5), Cyanine 5.5 (Cy 5.5), Cyanine 7 (Cy 7), Cyanine 7.5 (Cy 7.5), ATTO 488, ATTO 532, ATTO 600, ATTO 655, DY-505, DY-547, DY-632, DY-647; fluorescent proteins, such as green fluorescent protein (GFP) and modifications of GFP that have different absorption/emission properties. Herein a "marker molecule" may also be a complex of certain rare earth metals (e.g., europium, samarium, terbium or dysprosium), as these complexes can be used as fluorescent nanocrystals (quantum dots). More preferably, the "marker molecule" is a fluorophore selected from the group consisting of a dimethylaminocoumarin derivative, preferably 7-dimethylaminocoumarin-4-acetic acid succinimidyl ester, dansyl, 5/6-carboxyfluorescein and tetramethylrhodamine, BODIPY™-493/503, BODIPY™-FL, BODIPY™-TMR, BODIPY™-TMR-X, BODIPY™-TR-X, BODIPY™630/550-X, BODIPY™-650/665-X, Alexa 350, Alexa 488, Alexa 532, Alexa 546, Alexa 555, Alexa 635, Alexa 647, Cyanine 3 (Cy 3), Cyanine 3B (Cy 3B), Cyanine 5 (Cy 5), Cyanine 5.5 (Cy 5.5), Cyanine 7 (Cy 7), Cyanine 7.5 (Cy 7.5), ATTO 488, ATTO 532, ATTO 600, ATTO 655, DY-505, DY-547, DY-632, and DY-647. Preferred examples of optical imaging moieties are the cyanine dyes out of the group consisting of Carbacyanines, Oxacyanines, Thiacyanines and Azacyanines. Cyanine dyes are compounds defined by a polyene chain containing an odd number of carbon atoms linked by alternating single and multiple, preferably double, carbon-carbon bonds, terminated at either end by an amino group, one of which is quaternised. The cyanine and analogues aryl-linker-aryl chromophores optionally carry pendant or fused ring substituents. The cyanine dyes are particularly useful due to the wide range of spectral properties and structural variations available. A range of cyanine dyes are well known and tested, they have low toxicity, and are commercially available. The cyanine dyes are a single family of highly intense dyes with good aqueous solubility. They are pH insensitive between pH 3-10, exhibit low non-specific binding, and are more photostable than fluorescein.

Herein the "marker molecule" that is used in the azide-labeled compound may also be a radioactive marker. Examples for radioisotopes that are suitable for diagnostic radiopharmaceuticals are given in the following. Radioisotopes that can be use for positron emission tomography (PET) are, e.g., 18F, 11C, 64Cu, 13N, 15O, or 68Ga. Radioisotopes that can be used for gamma ray/photon (SPECT/scintigraphy) are, e.g., 99mTc, 123I, 125I, 131I, 111In, 57Co, 153Sm, 133Xe, 51Cr, 81mKr, 201Tl, 67Ga, or 75Se. For mass cytometry, metal based markers may be used. The radioisotope markers (particularly the metals described above) could be attached to the azide containing rest, e.g., by using metal chelators (for example DOTA or NOGADA moieties).

In context of the invention the "compound" of the azide-labeled compound may also be an antibody, e.g. an antibody directing the labyrinthopeptin derivative of the invention to a particular cell, tissue or organ. For example, the antibody my direct the labyrinthopeptin derivative to the liver (e.g. to hepatocytes). For the treatment of a DENV infection, the antibody may direct the labyrinthopeptin derivative to cells of the immune system (e.g. to T-cells or Langerhans dendritic cells). For the treatment of an infection with Herpesviridae the antibody may direct the labyrinthopeptin derivative to nerve cells (e.g. to oligodendrocytes or neurons). For the treatment of an infection with RSV the antibody may direct the labyrinthopeptin derivative to the lung (e.g. to the alveolae). For the treatment of an infection with CHIKV the antibody may direct the labyrinthopeptin derivative to muscle, joint or nerve tissue, e.g. addressing attachment factors such as TIM-1. For the treatment of an infection with TBEV the antibody may direct the labyrinthopeptin derivative to cells of the central nervous tissue (brain, spinal cord). For the treatment of an infection with ZIKV the antibody may direct the labyrinthopeptin derivative to subcutaneous tissue, the central nervous system, the skeletal muscles or the myocardium. For the treatment of an infection with HCV the antibody my direct the labyrinthopeptin derivative to the liver (e.g. to hepatocytes).

The appended Examples show derivatization of LabyA1 and LabyA2 with azide-labeled Biotin. Thus, in a preferred aspect of the present invention, the azide-labeled compound is azide-labeled Biotin.

Thus, the present invention provides a labyrinthopeptin derivative, wherein via dipolar cycloaddition between the terminal alkynyl group of $R_1$ and/or $R_2$ and an azide-labeled compound, said compound is added to obtain $R_1'$ and/or $R_2'$. Or, in other words, according to the invention a compound can be added to the labyrinthopeptin derivative via dipolar cycloaddition. This dipolar cycloaddition takes place between the terminal alkynyl group of $R_1$ and/or $R_2$ and the azide group of the azide-labeled compound. This dipolar cycloaddition converts $R_1$ to $R_1'$ and/or $R_2$ to $R_2'$. An overview of potential $R_1$ and $R_2$ as well as the corresponding $R_1'$ and $R_2'$ is given below.

As described above, $R_1$ may be a $(C_2$-$C_{12})$alkynyl, a $C(O)$—$(C_2$-$C_{12})$alkynyl, a $C(O)$—$O$—$(C_2$-$C_{12})$alkynyl, or a $C(O)NH$—$(C_2$-$C_{12})$alkynyl, wherein $R_1$ carries the alkynyl group at the terminal position. As also described above, $R_2$ may be $[C(O)]$—$NH$—$(C_2$-$C_{12})$alkynyl or a $[C(O)]$—$O$—$(C_2$-$C_{12})$alkynyl, wherein [CO] is the carbonyl group of the terminal amino acid, and wherein $R_2$ carries the alkynyl group at the terminal position.

The $R_1'$ and $R_2'$ groups that correspond to these $R_1$ and $R_2$ groups, respectively, are shown in Tables 1 and 2, below.

TABLE 1

Potential $R_1$ groups and the corresponding $R_1'$ groups.

| $R_1$ | $R_1'$ |
|---|---|
| $(C_2)$alkynyl (i.e. ethynyl) | triazole-compound* |
| $(C_3$-$C_{12})$alkynyl | $(C_1$-$C_{10})$alkyl-triazole-compound* |
| $C(O)$—$(C_2)$alkynyl (i.e. C(O)ethynyl) | $C(O)$-triazole-compound* |
| $C(O)$—$(C_3$-$C_{12})$alkynyl | $C(O)$—$(C_1$-$C_{10})$alkyl-triazole-compound* |
| $C(O)$—$O$—$(C_2)$alkynyl (i.e. $C(O)$—O-ethynyl) | $C(O)$—O-triazole-compound* |
| $C(O)$—$O$—$(C_3$-$C_{12})$alkynyl | $C(O)$—$O$—$(C_1$-$C_{10})$alkyl-triazole-compound* |
| $C(O)NH$—$(C_2)$alkynyl (i.e. C(O)NH-ethynyl) | $C(O)NH$-triazole-compound* |
| $C(O)NH$—$(C_3$-$C_{12})$alkynyl | $C(O)NH$—$(C_1$-$C_{10})$alkyl-triazole-compound* |
| hex-5ynoyl | $C(O)$—$(C_3)$alkyl-triazole-compound* |

*Here the "compound" is the compound that was azide-labeled before it had reacted with the alkynyl group of $R_1$. For example, said compound may be an anti-viral drug or a marker molecule.

TABLE 2

Potential $R_2$ groups and the corresponding $R_2'$ groups.

| $R_2$ | $R_2'$ |
|---|---|
| c | $[C(O)]$—NH-triazole-compound* |
| $[C(O)]$—NH—$(C_3$-$C_{12})$alkynyl | $[C(O)]$—NH—$(C_1$-$C_{10})$alkyl-triazole-compound* |
| $[C(O)]$—O—$(C_2)$alkynyl (i.e. $[C(O)]$—O-ethynyl) | $[C(O)]$—O-triazole compound* |
| $[C(O)]$—O—$(C_3$-$C_{12})$alkynyl | $[C(O)]$—O—$(C_1$-$C_{10})$alkyl-triazole-compound* |

*Here the "compound" is the compound that was azide-labeled before it had reacted with the alkynyl group of $R_2$. For example, said compound may be an anti-viral drug or a marker molecule.

Thus, in the labyrinthopeptin derivative of the present invention, a dipolar cycloaddition between the terminal alkynyl group of $R_1$ and/or $R_2$ and an azide-labeled compound may have occurred to give a triazole that binds the compound (e.g. the anti-viral drug or the marker molecule) to $R_1$ and/or $R_2$. Said compound may be any one of the anti-viral drugs or marker molecules as described above. Thus, the present invention relates to a labyrinthopeptin derivative (e.g. a derivative of LabyA1 or LabyA2), which comprises an anti-viral drug or a marker molecule. Or, in other words, the present invention relates to the herein provided labyrinthopeptin derivative, which comprises $R_1'$ instead of $R_1$ and/or $R_2'$ instead of $R_2$. Preferably, said labyrinthopeptin derivative comprises $R_1'$ instead of $R_1$ and $R_2$ is H.

The appended Examples demonstrate that the labyrinthopeptin derivative of the present invention has anti-viral activity, e.g. against a DENV infection. Thus, one aspect of the present invention relates to the herein provided labyrinthopeptin derivative for use as a medicament. Also encompassed by the present invention is a pharmaceutical composition comprising the labyrinthopeptin derivative of the invention, wherein the pharmaceutical composition further comprises a pharmaceutically acceptable carrier and/or diluent. The invention further relates to the labyrinthopeptin derivative of the invention or the pharmaceutical composition of the invention for use in treating and/or preventing an infectious disease, particularly a viral infection.

Thus, the labyrinthopeptin derivative or the pharmaceutical composition of the invention can be used for both, treating an existing viral infection or preventing the occurrence of a viral invention. It is preferred herein that the labyrinthopeptin derivative of the invention or the pharmaceutical composition of the invention is used for treating an existing viral infection. Said viral infection may be an infection with any one of the viruses selected from RSV, KSHV, CMV, DENV, CHIKV, TBEV, VSV, ZIKV and HCV, preferably DENV. Said infection (i.e. said infectious disease) may also be caused by a combination of infections with at least two of the viruses selected from RSV, KSHV, CMV, DENV, CHIKV, TBEV, VSV, ZIKV and HCV.

Accordingly, the present invention relates to a method of treating and/or preventing an infection with any one of the viruses selected from RSV, KSHV, CMV, DENV, CHIKV, TBEV, VSV, ZIKV, and HCV, preferably DENV, wherein the method comprises administering an effective dose of the labyrinthopeptin derivative of the present invention or of the pharmaceutical composition comprising said labyrinthopeptin derivative to a subject in need of such a treatment.

For example, one aspect of the present invention relates to a method of treating and/or preventing an infection with any one of the viruses selected from RSV, KSHV, CMV, DENV, CHIKV, TBEV, VSV and ZIKV, preferably DENV, wherein the method comprises administering an effective dose of the labyrinthopeptin derivative of the present invention or of the pharmaceutical composition comprising said labyrinthopeptin derivative to a subject in need of such a treatment.

Herein a "viral infection" or "infection with a virus" means an infectious disease, which is cause by an infection with a virus.

Anti-viral activity of LabyA1 and LabyA2 has been shown in the prior art. In particular, anti-viral activity of these substances against mycovirus (RNA virus/Influenza A), herpes simplex virus 1 and 2, adenovirus (DNA virus), human immunodeficiency virus (HIV), Human herpesvirus 6 (HHV-6) and Bovine viral diarrhea virus (BVDV) have been shown (WO 2008/040469 A1; Férir 2013, PLOS one, 8(5):e64010; and Meyerhans, 2015, Nat. Prod. Rep., 2015, 32, 29-48). In addition, as described above, activity of LabyA1 against HIV and DENV is known in the art. However, the prior art also discloses that the anti-viral effect of labyrinthopeptins is highly virus-specific. In particular, Férir et al. (2013, PLOS one, 8(5):e64010) discloses that none of the tested lantibiotics showed antiviral activity against the influenza viruses $H_1,N_1$, $H_3N_2$ and the influenza B virus. In addition, this document shows data demonstrating that LabyA1 interacts with the virus itself and not with the $CD4^+T$ cells. These data indicate that labyrinthopeptins act through a specific and direct interaction with particular selected virus species. In contrast, in context of the present invention it was surprisingly found that LabyA1 and LabyA2 have a considerably high anti-viral activity against CMV, KSHV, RSV, TBEV, ZIKV and HCV, and that LabyA1 has also a considerably high anti-viral activity against CHIKV and VSV. These viruses are completely different from all viruses for which activity has been shown in the prior art. RSV belongs to the viral family of Paramyxoviruses that is completely unrelated to all viruses for which an activity of LabyA1 or LabyA2 has been shown in the prior art. CHIKV belongs to the family of Togaviridae; VSV belongs to the family of Rhabdoviridae; and HCV belongs to the family Flaviviridae. These families are also completely unrelated to the viruses for which an activity of labyrinthopeptins has been shown in the prior art. As HSV (for which the anti-viral activity of LabyA1 and LabyA2 has already been demonstrated) KSHV and CMV are representatives of the family of herpes viruses. However, KSHV and CMV have different biological and pathophysiological properties. HSV belongs to the subfamily of Alphaherpesvirinae whose members are neurotropic (infect nervous system tissue) and have a short reproductive cycle (~18 hrs). Their primary target cells are in the mucoepithelium. They may persist in neurons. In contrast, KSHV and CMV belong to the subfamilies of Gammaherpesvirinae and Betaherpesvirinae, respectively. Betaherpesvirinae are lymphotropic and have a long reproductive cycle. They have a restricted host range and infected cells become enlarged (cytomegalo). Compared to Alphaherpesvirinae, they establish their latency in leucocytes, not in neurons. Gammaherpesvirinae are also lymphotropic and specific for either T or B lymphocytes. Both, Gammaherpesvirinae and Betaherpesvirinae may be cancerogenic whereas Alphaherpesvirinae are not. Labyrinthopeptins have been described as having a highly specific mode of action. Therefore, the finding that LabyA1 and LabyA2 have anti-viral action on selected viruses that are completely different as compared to the viruses for which anti-viral activity of labyrinthopeptins has been described in the art is entirely unexpected.

Thus, another aspect of the present invention relates to a peptide (i.e. a labyrinthopeptin) for use in treating and/or preventing an infection with any one of the viruses selected from RSV, KSHV, CMV, CHIKV, TBEV, VSV, ZIKV and HCV wherein said peptide comprises or consists of the amino acid sequence (SEQ ID NO: 2)

$$\text{Lab-}X_1-X_2\text{-Lab-}X_3-X_4-X_5\text{-Lab-Cys-Lab-}X_6-X_7\text{-Lab-}X_8\text{-Lab-Cys}$$

with disulfide bridges S—S and S—S and CH$_2$ groups as shown.

wherein
Lab is labionin
$X_1$ is an amino acid selected from Asn, Asp, and Glu;
$X_2$ is an amino acid selected form Ala, Trp, and Ser;
$X_3$ is an amino acid selected from Val, Leu, and Ile;
$X_4$ is an amino acid selected from Trp and Tyr;
$X_5$ is an amino acid selected from Glu and Asp;
$X_6$ is an amino acid selected from Thr and Ser;
$X_7$ is an amino acid selected from Gly and Pro; and
$X_8$ consists of a sequence of 3 to 5 amino acids.

The labyrinthopeptin of the present invention has anti-viral activity, particularly against RSV, KSHV, CMV, DENV, CHIKV, TBEV, VSV, ZIKV and/or HCV (e.g. against RSV, KSHV, CMV, CHIKV, TBEV, VSV and/or ZIKV), preferably against RSV, KSHV, CMV, CHIKV, TBEV, ZIKV and/or HCV; even more preferably against RSV, KSHV, CMV, ZIKV and/or HCV; even more preferably against KSHV, CMV, ZIKV and/or HCV; even more preferably against CMV and/or HCV; and most preferably against CMV.

The amino acid labionin (or Labionin) as well as their occurrence in labyrinthopeptins is known in the art and described, e.g., in Häbich, Angew. Chem. Int. Ed., 2010, 49: 1151-1154. In particular, labionin is an amino acid that actually spans over three residues, in analogy to lanthionin (see FIG. 1). The C-alpha atom spans the bridges. The structure of labionin is shown in FIG. 1.

Another aspect of the present invention relates to a pharmaceutical composition comprising the labyrinthopeptin of the present invention for use in treating and/or preventing an infection with any one of the viruses selected from RSV, KSHV, CMV, CHIKV, TBEV, VSV, ZIKV and HCV, wherein the pharmaceutical composition further comprises a pharmaceutically acceptable carrier and/or diluent. Thus, the present invention relates to a method of treating and/or preventing an infection with any one of the viruses selected from RSV, KSHV, CMV, CHIKV, TBEV, VSV, ZIKV and HCV, wherein the method comprises administering an effective dose of the labyrinthopeptin of the present invention or of the pharmaceutical composition comprising said labyrinthopeptin to a subject in need of such a treatment. It is preferred herein that said labyrinthopeptin or said pharmaceutical composition is used for treating an existing infectious disease caused by a viral infection with any one of viruses selected from RSV, KSHV, CMV, CHIKV, TBEV, VSV, ZIKV and HCV, or an existing viral invention that is caused by a combination of infections with at least two of the viruses selected from RSV, KSHV, CMV, CHIKV, TBEV, VSV, ZIKV and HCV.

Preferably, the pharmaceutical composition or the treatment method is used for treating and/or preventing an infection with any one of the viruses selected from RSV, KSHV, CMV, CHIKV, TBEV, VSV, ZIKV and/or HCV (e.g. selected from RSV, KSHV, CMV, CHIKV, TBEV, VSV and/or ZIKV), more preferably selected from RSV, KSHV, CMV, CHIKV, TBEV, ZIKV and/or HCV; even more preferably selected from RSV, KSHV, CMV, ZIKV and/or HCV; even more preferably selected from KSHV, CMV, ZIKV and/or HCV; even more preferably selected from CMV and/or HCV; and most preferably CMV.

The labyrinthopeptin of the present invention or the labyrinthopeptin derivative of the present invention may have a length of maximal 50 amino acids, more preferably of maximal 40 amino acids, and even more preferably of maximal 30 amino acids. Thus, one aspect of the present invention relates to the herein provided labyrinthopeptin derivative, pharmaceutical composition comprising said labyrinthopeptin derivative, or to the herein provided method, wherein said peptide (i.e. said labyrinthopeptin derivative) has a length of maximal 30 amino acids. Analogously, the invention relates to the herein provided labyrinthopeptin, to the herein provided pharmaceutical composition comprising said labyrinthopeptin, or to the herein provided method, wherein said peptide (i.e. said labyrinthopeptin) has a length of maximal 30 amino acids. It is even more preferred that the labyrinthopeptin or the labyrinthopeptin derivative of the present invention has a length of maximal 25 amino acids. Most preferably, the labyrinthopeptin or the labyrinthopeptin derivative of the present invention has 18-20 amino acids.

As mentioned above, in the labyrinthopeptin or labyrinthopeptin derivative of the present invention as shown in SEQ ID NOs: 1 and 2, respectively, $X_8$ consists of a sequence of 3 to 5 amino acids. For example, $X_8$ may consist of the amino acid sequence $X_{8-1}$ to $X_{8-5}$ as shown below:
$X_{8-1}$ is absent or an amino acid selected from Trp or Tyr;
$X_{8-2}$ is an amino acid selected from Val, Leu and Ile;
$X_{8-3}$ is absent or an amino acid selected from Pro and Gly;
$X_{8-4}$ is an amino acid selected from Phe, Met, Leu and Tyr, and
$X_{8-5}$ is an amino acid selected from dehydrobutyrine, Ala, Thr, Asn and Ser.

Dehydrobutyrine (Dhb) (also called didehydrobutyrine) is a naturally occurring amino acid that is present in a range of peptides including antimicrobial peptides of the lantibiotic family. In nature, the site-specific introduction of dehydrobutyrine into peptide chains arises due to enzymatic post-translational modifications, in which a threonine residue is dehydrated by phosphorylation followed by β-elimination. The structure of dehydrobutyrine as present in LabyA1 is shown in FIG. 2.

In an example of the herein provided labyrinthopeptin or labyrinthopeptin derivative, $X_8$ consists of the amino acid sequence Trp-Val-Pro-Phe-dehydrobutyrine (SEQ ID NO:8). Alternatively, $X_8$ may consist of the amino acid sequence Leu-Phe-Ala.

One aspect of the present invention relates to the herein provided labyrinthopeptin, labyrinthopeptin derivative, pharmaceutical compositions, or methods, wherein
$X_1$ is Asn or Asp;
$X_2$ is Ala or Trp;
$X_3$ is Val or Leu;
$X_4$ is Trp;
$X_5$ is Glu;
$X_6$ is Thr;
$X_7$ is Gly; and
$X_8$ is an amino acid sequence consisting of the amino acid sequence Trp-Val-Pro-Phe-dehydrobutyrine (SEQ ID NO:8), or consisting of the amino acid sequence Leu-Phe-Ala.

The labyrinthopeptin of the invention or labyrinthopeptin comprised in the labyrinthopeptin derivative of the invention may comprise or consist of LabyA2. Thus, one aspect of the present invention relates to the labyrinthopeptin provided herein, to the labyrinthopeptin derivative provided herein, to the pharmaceutical compositions provided herein, or to the methods provided herein wherein
$X_1$ is Asp;
$X_2$ is Trp;
$X_3$ is Leu;
$X_4$ is Trp;
$X_5$ is Glu;
$X_6$ is Thr;
$X_7$ is Gly; and
$X_8$ is an amino acid sequence consisting of the amino acid sequence Leu-Phe-Ala.

In a preferred aspect of the present invention the labyrinthopeptin of the invention is LabyA2, e.g. as shown in FIG. 4. More preferably, the labyrinthopeptin of the invention is LabyA2 as shown in FIG. 3(B), having the stereochemistry of natural LabyA2. It is also preferred that the labyrinthopeptin derivative of the present invention comprises LabyA2, e.g. as shown in FIG. 4. More preferably, the labyrinthopeptin derivative of the invention comprises LabyA2 as shown in FIG. 3(B), having the stereochemistry of natural LabyA2.

A preferred aspect of the invention relates to LabyA2 for use in treating and/or preventing an infection with any one of the viruses selected from RSV, KSHV, TBEV, VSV, CMV, ZIKV and HCV (e.g. selected fro RSV, KSHV, TBEV, VSV, CMV and ZIKV), preferably selected from KSHV, CMV, ZIKV and HCV, more preferably selected from CMV, ZIKV and HCV, and even more preferably HCV.

However, it is more preferred that the labyrinthopeptin of the invention or the labyrinthopeptin comprised in the labyrinthopeptin derivative of the invention comprises or consists of LabyA1. Thus, one aspect of the present invention relates to the labyrinthopeptin provided herein, to the labyrinthopeptin derivative provided herein, to the pharmaceutical compositions provided herein, or to the methods provided herein wherein $X_1$ is Asn;
$X_2$ is Ala;
$X_3$ is Val;
$X_4$ is Trp;
$X_5$ is Glu;
$X_6$ is Thr;
$X_7$ is Gly; and
$X_8$ is an amino acid sequence consisting of the amino acid sequence Trp-Val-Pro-Phe-dehydrobutyrine (SEQ ID NO:8).

In an even more preferred aspect of the present invention the labyrinthopeptin of the invention is LabyA1, e.g. as shown in FIG. 4. Even more preferably, the labyrinthopeptin of the invention is LabyA1 as shown in FIG. 3(A), having the stereochemistry of natural LabyA1. It is also more preferred that the labyrinthopeptin derivative of the present invention comprises LabyA1, e.g. as shown in FIG. 4. Even more preferably, the labyrinthopeptin derivative of the invention comprises LabyA1 as shown in FIG. 3(A), having the stereochemistry of natural LabyA1.

A preferred aspect of the invention relates to LabyA1 for use in treating and/or preventing an infection with any one of the viruses selected from RSV, KSHV, TBEV, CMV VSV, CHIKV, ZIKV and HCV (e.g. selected from RSV, KSHV, TBEV, CMV VSV, CHIKV and ZIKV), preferably selected from RSV, KSHV, CMV, CHIKV, ZIKV and HCV, more preferably selected from KSHV, CMV, CHIKV, ZIKV and HCV, even more preferably selected from CMV, CHIKV and HCV.

In context of the invention it was surprisingly shown that the anti-viral activity of the combination of LabyA1 and LabyA2 was significantly higher than that of the individual molecules. Such a synergistic effect of a combination of LabyA1 and LabyA2 has never been disclosed or suggested in the prior art. Quite to the contrary, due to the lack of anti-HIV and only moderate anti-HSV activity, LabyA2 was described to be a less attractive candidate for further antiviral studies (Férir, 2013, PLOS one, 8(5):e64010). However, in context of the present invention it has surprisingly and unexpectedly been found that in combination with LabyA1, LabyA2 results in a considerably high anti-viral activity. This synergistic effect was not foreseeable.

Thus, the present invention relates to a combination of at least two labyrinthopeptins or labyrinthopeptin derivatives for use as a medicament. Particularly, one aspect of the present invention relates to a combination of (i) and (ii) for use as a medicament, wherein (i) and (ii) are:

(i) a labyrinthopeptin or labyrinthopeptin derivative of the present invention having $X_1$ is Asn;
$X_2$ is Ala;
$X_3$ is Val;
$X_4$ is Trp;
$X_5$ is Glu;
$X_6$ is Thr;
$X_7$ is Gly; and
$X_8$ is an amino acid sequence consisting of the amino acid sequence Trp-Val-Pro-Phe-dehydrobutyrine (SEQ ID NO:8); and (ii) a labyrinthopeptin or labyrinthopeptin derivative of the present invention having $X_1$ is Asp;
$X_2$ is Trp;
$X_3$ is Leu;
$X_4$ is Trp;
$X_5$ is Glu;
$X_6$ is Thr;
$X_7$ is Gly; and
$X_8$ is an amino acid sequence consisting of the amino acid sequence Leu-Phe-Ala.

In context of the invention it was surprisingly shown that the antiviral activity of the combination of LabyA1 and LabyA2 could even be increased if the ratio of LabyA1 and LabyA2 is 1:1. Thus, the invention relates to the herein provided combination, wherein the ratio of the labyrinthopeptin/labyrinthopeptin derivative (i), and the labyrinthopeptin/labyrinthopeptin derivative (ii) is from 1:10 to 10:1, preferably from 1:5 to 5:1, even more preferably from 2:1 to 1:2, and most preferably 1:1. Or, in other words, the ratio of the concentrations of the labyrinthopeptin/labyrinthopeptin derivative (i), and the labyrinthopeptin/labyrinthopeptin derivative (ii) is from 1:10 to 10:1, preferably from 1:5 to 5:1, even more preferably from 2:1 to 1:2, and most preferably 1:1, wherein the concentration is determined, e.g. in µM.

Assays for testing the anti-viral activity of compounds such as labyrinthopeptins are commonly known in the art. For example, to test for the anti-viral activity of the combination of the invention, the combination may be added to cells (e.g. Huh-7.5 cells). Then, the cells may be infected with the virus to be tested (e.g. RSV, KSHV, CMV, DENV, CHIKV, TBEV, VSV, ZIKV and/or HCV, preferably DENV, TBEV and/or ZIKV). The amount of virus-positive cells may be evaluated by immunocytochemistry. For example, a primary antibody directed against the virus and a secondary antibody that has a conjugated fluorophore may be applied. The number of total cells may be determined by counting DAPI-stained nuclei. Thus, the percentage of virus-positive cells may be calculated. The obtained result is preferably compared to non-infected cells.

Another aspect of the invention relates to a pharmaceutical composition comprising the combination of the present invention, wherein the pharmaceutical composition further comprises a pharmaceutically acceptable carrier and/or diluent. The combination of the invention or the pharmaceutical composition comprising said combination may be used for treating and/or preventing a viral infection. Said viral infection may be an infection with any one of the viruses selected from RSV, KSHV, CMV, DENV, CHIKV, TBEV, VSV, ZIKV and HCV (e.g. selected from RSV, KSHV, CMV, DENV, CHIKV, TBEV, VSV and ZIKV), preferably selected from DENV, TBEV and ZIKV. Thus, one aspect of the present invention relates to a method of treating and/or preventing an infection with any one of the viruses selected from RSV, KSHV, CMV, DENV, CHIKV, TBEV, VSV, ZIKV and HCV, (e. g. selected from RSV, KSHV, CMV, DENV, CHIKV, TBEV, VSV and ZIKV; preferably selected from DENV, TBEV and ZIKV), wherein the method comprises administering an effective dose of the combination of the invention, or the pharmaceutical composition comprising said combination to a subject in need of such a treatment. Preferably, the combination of the invention, the pharmaceutical composition comprising said combination, or the method of the present invention is used for treating an existing infectious disease (i.e. an existing viral infection).

One aspect of the invention relates to the herein provided labyrinthopeptin, labyrinthopeptin derivative, combination, pharmaceutical compositions, or methods, wherein the labyrinthopeptin, the combination or the pharmaceutical composition is co-administered with at least one other active agent. Said active agent may be a CMV inhibitor, a KSHV inhibitor, a RSV inhibitor, a DENV inhibitor, a CHIKV inhibitor, a TBEV inhibitor, a VSV inhibitor, a ZIKV inhibitor and/or a HCV inhibitor.

Suitable CMV inhibitors and KSHV inhibitors are known in the art and described, e.g. in Coen, 2014, Viruses 6(11): 4731-59. For example, suitable CMV and KSHV inhibitors include viral DNA polymerase inhibitors such as aciclovir, penciclovir, Zidovudine, brivudin, cidofovir HDVD (L-dioxolane uracil analog), Idoxuridin, Famciclovir, Sorivudin, Valaciclovir, Cidofovir, Brincidofovir, Ganciclovir, Valganciclovir, Foscarnet, Maribavir, CMVIG, Letermovir, Leflunomide (antimetabolite, used as a disease-modifying agent in rheumatoid arthritis, has also been successfully used off-label in both CMV disease treatment and prophylaxis) and Fomivirsen.

RSV inhibitors that are useful in the context of the present invention include monoclonal antibodies such as Palivizumab (Motavizumab). This antibody represents the only specific therapeutic option currently available for RSV (Roymans, 2010 Future Med Chem 2(10): 1523-7.). Other RSV inhibitors that can be used in accordance with the present invention are nucleoprotein (N-Protein) inhibitors such as RSV604 (Challa, 2015, Antimicrob Agents Chemother 59(2): 1080-7); and RNA interference molecules such as ALN-RSV01 (i.e. a small interfering RNA targeting the N-protein of RSV). Such a small interfering RNA is a treatment option for the at-risk adult population (DeVincenzo, 2010; Roymans, 2010, Future Med Chem 2(10): 1523-7.). Other RSV inhibitors that may be applied in context of the invention are nucleoside inhibitors such as ALS-8176 (Challa, 2015, Antimicrob Agents Chemother 59(2): 1080-7); or viral fusion inhibitors such as GS-5806 (Gilead®), (DeVincenzo, 2014, Proc Natl Acad Sci USA 107(19): 8800-5.).

DENV inhibitors that may be used in context of the invention include vaccines such as CYD-TDV (recombinant, live, attenuated, tetravalent dengue vaccine). CYD-TDV is currently in clinical trials (Hadinegoro, 2015, N Engl J Med 373(13): 1195-206.). Herein "DENV inhibitors" may further include nucleoside analogs (Lim, 2013, Antiviral Res 100(2): 500-19.) such as NITD-008 or Balapiravir.

One promising inhibitor of TBEV that may be used in context of the present invention is 7-deaza-2-C-methyladenosine (7-deaza-2-CMA).

In another example, the herein provided labyrinthopeptins, combination or pharmaceutical composition is co-administered with a HCV inhibitor, e.g. with one or a combination of direct acting antiviral(s) targeting either the HCV NS3/4A protease (telaprevir, boceprevir, simeprevir, paritaprevir, asunaprevir, vaniprevir, vedroprevir, sovaprevir, grazoprevir or ACH-2684), the NS5A phosphoprotein (daclatasvir, ledipasvir, ombitasvir, elbasvir, GS-5816 or ACH-3102) or the RNA-dependent RNA polymerase NS5B (sofosbuvir, MK-3682, ACH-3422, AL-335, dasabuvir, beclabuvir, or GS-9669). Moreover, a co-administration with host targeting antiviral drugs in the context of HCV infection is conceivable. These include miR-122 targeting therapeutics like for instance miravirsen or cyclophilin antagonists like alisporivir, NIM 811, or SCY-635.

The herein provided labyrinthopeptin, labyrinthopeptin derivative, combination, or pharmaceutical composition may be administered by suitable routes. One aspect of the present invention relates to the herein provided labyrinthopeptin, labyrinthopeptin derivative, combination, pharmaceutical compositions, or methods, wherein the peptide, the combination or the pharmaceutical composition is to be administered orally, intravenously, subcutaneously or intramuscularly. Preferably, the administration is intravenously, subcutaneously or intramuscularly. For example, the administration may be intravenously. However, subcutaneous or intramuscular administration has the advantage that these modes of administration are more practical than intravenous administration. If the administration is orally, it is envisaged that the formulation enables oral bioavailability.

The appended Examples demonstrate that the herein provided labyrinthopeptin, labyrinthopeptin derivative or combination has high anti-viral activity. Thus, one aspect of the present invention relates to the labyrinthopeptin of the invention, the labyrinthopeptin derivative of the invention, the combination of the invention, the pharmaceutical compositions of the invention, or the methods of the invention, wherein the IC50 value of the anti-viral activity of the herein provided labyrinthopeptin, labyrinthopeptin derivative, combination, or pharmaceutical composition is at least 50 µM, preferably at least 26 µM. Preferably, the labyrinthopeptin of the invention is LabyA1 and the IC50 value is at least 25 µM, more preferably at least 4 µM. With respect to the combination of the present invention the IC50 value is preferably at least 9 µM, more preferably at least 1.5 µM. With respect of the labyrinthopeptin derivative of the present invention the treated viral infection is preferably an infection with DENV and the IC50 value is preferably at least 7.5 µM. More preferably, the labyrinthopeptin derivative of the present invention is a derivative of LabyA1, the treated viral infection is an infection with DENV and the IC50 value is at least 2 µM.

Another aspect of the invention relates to the labyrinthopeptin of the invention, the labyrinthopeptin derivative of the invention, the combination of the invention, the pharmaceutical compositions of the invention, or the methods of the invention, wherein the viral infection to be treated is an infection with CMV, ZIKV or HCV and the IC50 value of the anti-viral activity of the herein provided labyrinthopeptin, labyrinthopeptin derivative, combination, or pharmaceutical composition is at least 5.5 µM. Preferably, the labyrinthopeptin of the present invention is LabyA1, the viral infection to be treated and/or prevented is an infection with CMV, or HCV and the IC50 value is at least 1.5 µM.

A further aspect of the invention relates to the labyrinthopeptin of the invention, the labyrinthopeptin derivative of the invention, the combination of the invention, the pharmaceutical compositions of the invention, or the methods of the invention, wherein the viral infection to be treated is an infection with DENV and the IC50 value of the anti-viral activity of the herein provided labyrinthopeptin, labyrinthopeptin derivative, combination, or pharmaceutical composition is at least 8 µM. Preferably, the labyrinthopeptin of the present invention is LabyA1, the viral infection to be treated and/or prevented is an infection with DENV and the IC50 value is at least 2 µM.

A further aspect of the invention relates to the labyrinthopeptin of the invention, the labyrinthopeptin derivative of the invention, the combination of the invention, the pharmaceutical compositions of the invention, or the methods of the invention, wherein the labyrinthopeptin of the present invention is LabyA1, the viral infection to be treated and/or prevented is an infection with CHIKV and the IC50 value is at least 2 µM.

Table 3 shows the IC50 values of the anti-viral activities of LabyA1, LabyA2, the combination of LabyA1 and LabyA2 (LabyA1/A2), the LabyA1 derivative "LabyA1-hexyn" (herein also called "LabyA1-Hexyn"), the LabyA2 derivative "LabyA2-hexyn" (herein also called "LabyA2-Hexyn"), as well as the combination of LabyA1-hexyn and LabyA2-hexyn (LabyA1/A2-hexyn).

TABLE 3

IC50 values (in μM and μg/ml) of the anti-viral activity of labyrinthopeptins, combinations of labyrinthopeptins and labyrinthopeptin derivatives.

| | LabyA1 | | LabyA2 | | LabyA1/A2 | | LabyA1-hexyn | | LabyA2-hexyn | | LabyA1/A2-hexyn | |
|---|---|---|---|---|---|---|---|---|---|---|---|---|
| | μM | μg/ml | μM | μg/ml | μM | μg/ml | μM | μg/ml | μM | μg/ml | μM | μg/ml |
| DENV | 1.78 | 3.7 | 8.00 | 15.4 | 1.30 | 2.6 | 1.70 | 3.7 | 7.03 | 14.2 | 0.96 | 2.0 |
| RSV | 0.39[1] | 0.8[1] | 4.97[1] | 9.56[1] | — | — | — | — | — | — | — | — |
| KSHV | 2 | 4.2 | 15 | 28.9 | — | — | — | — | — | — | — | — |
| TBEV | 24.10 | 50 | >25.99 | >50 | 8.34 | 16.67 | — | — | — | — | — | — |
| CMV | 1.3 | 2.7 | 5.4 μM | 10.4 | — | — | — | — | — | — | — | — |
| CHIKV | 0.5-1.7 | 1.0-3.5 | — | — | — | — | — | — | — | — | — | — |
| VSV | 1.1-3.7 | 2.3-7.7 | — | — | — | — | — | — | — | — | — | — |
| ZIKV | 2.22 | 4.6 | 2.81 | 5.4 | 1.75 | 3.5 | — | — | — | — | — | — |
| HCV | 1.05 | 2.18 | 1.728 | 3.32 | — | — | — | — | — | — | — | — |
| | LabyA1 = 2075.33 g/mol | | LabyA2 = 1924.16 g/mol | | | | LabyA1-hexyn = 2170.45 g/mol | | LabyA2-hexyn = 2019.28 g/mol | | | |

[1]These values are measured by intracellular RSV-P staining (see FIG. 16C).

Figure 15:
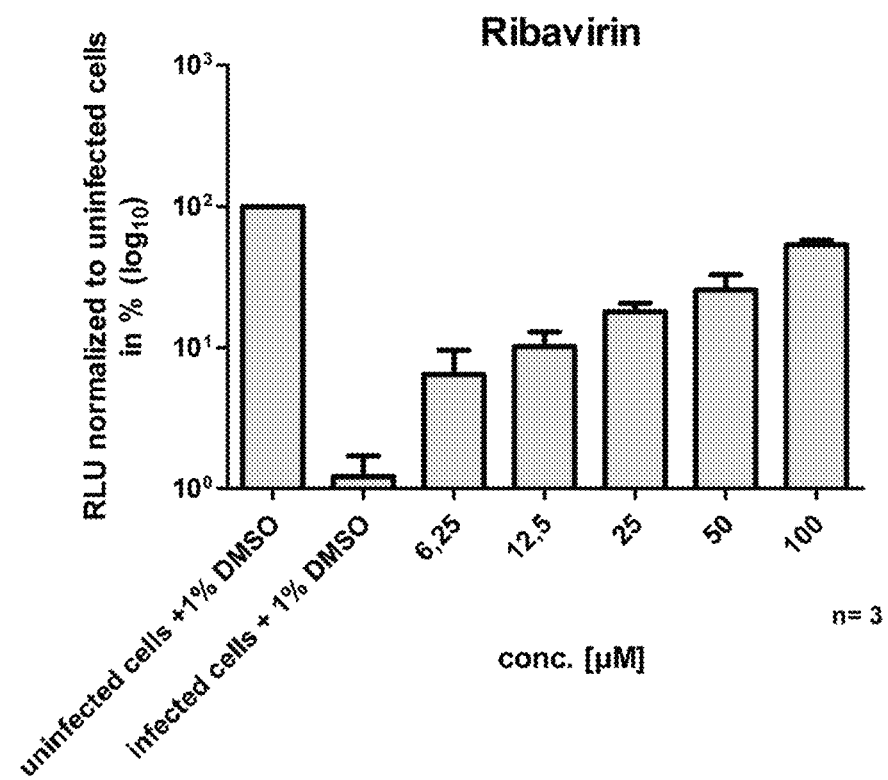

For RSV the appended examples also show somehow higher IC50 values (see FIGS. 16A and 16B). However, these higher values have been obtained by using an indirect high throughput screening assay (FIG. 15). In this indirect high throughput screening assay the antiviral activity of compounds is roughly estimated based on the ability of a compound to rescue cell survival upon challenge with RSV which is a lytic virus. Since the host cells used in this assay constitutively express a luciferase reporter gene, changes in cell survival can be quantified by luciferase assays. However, due to the indirect nature of this assay, the precision of IC50 values is limited. In other experiments summarized in FIG. 16C the IC50 of labyrinthopeptins against RSV were precisely determined by using a direct, quantitative assay that measures RSV dependent protein expression in the infected cells. Specifically, in this assay cells are inoculated with RSV (i.e. hRSV) in the presence or absence of the compound to be tested (e.g. labyrinthopeptins). Subsequently, infection efficiency is determined by using an intracellular FACS staining based on hRSV P protein detection, e.g. by using a mouse monoclonal antibody. Using this approach it is possible to directly determine the number of RSV infected cells; and thus precisely quantify the IC50.

As demonstrated in the appended Examples, labyrinthopeptins (particularly LabyA1) have a high anti-viral activity against CMV. Thus, in a preferred aspect of the herein provided labyrinthopeptin, labyrinthopeptin derivative, combination, pharmaceutical compositions, or methods, the treated viral infection is an infection with CMV (i.e. HCMV).

As mentioned above, the appended Examples show that a combination of LabA1 and LabyA2 results in a synergistic effect in the treatment of viruses. For example, a synergistic activity of LabyA1 and LabyA2 in the anti-viral activity against DENV, TBEV or ZIKV has been shown. Thus, particularly in the context of the herein provided combination, the viral infection is preferably an infection with DENV, TBEV and/or ZIKV.

The terms "labyrinthopeptin(s) of the (present) invention", "labyrinthopeptin(s) provided herein", and "herein provided labyrinthopeptin(s)" are used interchangeably herein. These terms refer to peptides (i.e. compounds) as defined in SEQ ID NO: 2 that exhibit anti-viral activity, particularly against RSV, KSHV, CMV, DENV, CHIKV, TBEV, VSV, ZIKV and HCV, which may be measured using methods known in the art. For example, to test for the anti-viral activity of the labyrinthopeptin of the invention, the labyrinthopeptin of the invention may be added to cells (e.g. Huh-7.5 cells). Then, the cells may be infected with the virus to be tested (e.g. RSV, KSHV, CMV, DENV, CHIKV, TBEV, VSV, ZIKV and/or HCV). The amount of virus-positive cells may be evaluated by immunocytochemistry. For example, a primary antibody directed against the virus and a secondary antibody that has a conjugated fluorophore may be applied. The number of total cells may be determined by counting DAPI-stained nuclei. Thus, the percentage of virus-positive cells may be calculated. The obtained result is preferably compared to non-infected cells.

Particularly, the terms "labyrinthopeptin(s) of the (present) invention", "labyrinthopeptin(s) provided herein", and "herein provided labyrinthopeptin(s)" refer to a peptide (i.e. compound) that comprises or consists of the amino acid sequence (from N- to C-terminus)

(SEQ ID NO: 2)

$$\text{Lab-}X_1\text{—}X_2\text{-Lab-}X_3\text{—}X_4\text{—}X_5\text{-Lab-Cys-Lab-}X_6\text{—}X_7\text{-Lab-}X_8\text{-Lab-Cys}$$

with disulfide bridges and CH$_2$ linkages connecting the residues as depicted.

wherein
Lab is labionin
$X_1$ is an amino acid selected from Asn, Asp, and Glu;
$X_2$ is an amino acid selected form Ala, Trp, and Ser;
$X_3$ is an amino acid selected from Val, Leu, and Ile;
$X_4$ is an amino acid selected from Trp and Tyr;
$X_5$ is an amino acid selected from Glu and Asp;
$X_6$ is an amino acid selected from Thr and Ser;
$X_7$ is an amino acid selected from Gly and Pro; and
$X_8$ consists of a sequence of 3 to 5 amino acids.

The amino acid sequence of SEQ ID NO: 2 starts with the N-terminus and ends with the C-terminus, i.e. the sequence of SEQ ID NO: 2 is displayed from N- to C-terminus.

Preferred amino acids for the positions $X_1$, $X_2$, $X_3$, $X_4$, $X_5$, $X_7$ and $X_8$ are described herein above. In SEQ ID NO: 2 "—" is a chemical bond. If "—" is placed between "X" and "X" (e.g. $X_1$-$X_2$, $X_3$-$X_4$, $X_4$-$X_5$, or $X_6$-$X_7$) or between "X" and "Lab" (e.g. "Lab-$X_1$", "$X_2$-Lab", "Lab-$X_3$", "$X_5$-Lab", "Lab-Cys", "Lab-$X_6$", "$X_7$-Lab", "Lab-$X_8$"), than "—" is preferably a peptide bond/linkage. "—S—S—" is a disulfide bridge (also called SS-bond). "—S—" is a thioether bridge between the β-C-atoms of the two alanine-residues that represent the lanthionine part of Lab.

The labionins at positions 1 and 4 of SEQ ID NO: 2 (counted from the N-terminus) and the labionins at positions 10 and 13 of SEQ ID NO: 2 (counted from the N-terminus) are linked via a methylene bridge (i.e. —$CH_2$—). In particular, a methylene group links the αC atoms of the labionins at positions 1 and 4 of SEQ ID NO: 2. Another methylene group links the αC atoms of the labionins at positions 10 and 13 of SEQ ID NO: 2.

As mentioned above, a preferred aspect of the present invention relates to a combination or LabyA1 and LabyA2 (i.e. the combination of the present invention). With respect to the labyrinthopeptin of the present invention, LabyA1 and LabyA2 are preferred; LabyA1 is more preferred. The amino acid sequence (including the internal bridges) of LabyA1 is shown in the following SEQ ID NO: 3:

(SEQ ID NO: 3)

Lab-Asn-Ala-Lab-Val-Trp-Glu-Lab-Cys-Lab-Thr-Gly-Lab-Trp-Val-Pro-Phe-Dhb-Lab-Cys with S—S bridges between Cys residues, and $CH_2$ bridges and S bridges connecting the Lab residues.

wherein Dhb is dehydrobutyrine (also called didehydrobutyrine), and Lab is labionin. The structure of Dhb is shown in FIG. 2.

The amino acid sequence (including the internal bridges) of LabyA2 is shown in the following SEQ ID NO: 4:

(SEQ ID NO: 4)

Lab-Asp-Trp-Lab-Leu-Trp-Glu-Lab-Cys-Lab-Thr-Gly-Lab-Leu-Phe-Ala-Lab-Cys with S—S bridges between Cys residues, and $CH_2$ bridges and S bridges connecting the Lab residues.

wherein Lab is labionin.

The labyrinthopeptins of the present invention also include peptides that have at least 80%, preferably at least 85%, more preferably at least 90%, and even more preferably at least 95% sequence identity to the amino acid sequence as shown in SEQ ID NO: 3, wherein the peptide has at least 50%, preferably at least 90% of the anti-viral activity of LabyA1, particularly against RSV, KSHV, CMV, DENV, CHIKV, TBEV, VSV, ZIKV and/or HCV. The labyrinthopeptins of the present invention further include peptides that have at least 80%, preferably at least 85%, more preferably at least 90%, and even more preferably at least 94% sequence identity to the amino acid sequence as shown in SEQ ID NO: 4, wherein the peptide has at least 50%, preferably at least 90% of the anti-viral activity of LabyA2, preferably against RSV, KSHV, CMV, DENV, TBEV, ZIKV and/or HCV.

The labyrinthopeptins of the present invention also include peptide analogs and peptidomimetics (or peptide mimetics), that exhibit anti-viral activity, particularly against RSV, KSHV, CMV, DENV, CHIKV, TBEV, VSV, ZIKV and/or HCV.

The labyrinthopeptins of the present invention include a peptide of SEQ ID NO: 2, 3, or 4 in any stereochemical form, or a mixture of any stereochemical forms in any ratio. Unless otherwise indicated, the chiral centers in the peptide of SEQ ID NO: 2, 3, or 4 can be present in the R configuration or in the S configuration. The invention relates to both optically pure compounds and to stereoisomeric mixtures, such as enantiomeric mixtures and diastereomeric mixtures. Preferably, the labyrinthopeptin of the present invention has the stereochemistry of natural LabyA1 or LabyA2 as shown in FIG. 3.

The labyrinthopeptins of the present invention are described herein (e.g. by SEQ ID NO: 2). However, the labyrinthopeptins of the present invention also comprise the modified labyrinthopeptins as disclosed in Krawczyk, Chemistry & Biology, 2013, 20(1), 111-122; and WO 2013/092672, provided that these modified labyrinthopeptins have anti-viral activity, particularly against RSV, KSHV, CMV, DENV, CHIKV, TBEV, VSV, ZIKV and/or HCV.

In addition, the terms "labyrinthopeptin(s) of the (present) invention", "labyrinthopeptin(s) provided herein", and "herein provided labyrinthopeptin(s)", also relate to a pharmaceutical acceptable salt of a peptide as defined in SEQ ID NO: 2, 3, or 4. Thus, also pharmaceutical acceptable salts are included by the term "labyrinthopeptin of the present invention".

The terms "labyrinthopeptin derivative(s) of the (present) invention", "labyrinthopeptin derivative(s) provided herein", and "herein provided labyrinthopeptin derivative(s)" are used interchangeably herein. These terms refer to peptides (i.e. compounds) as defined in SEQ ID NO: 1, that exhibit anti-viral activity, particularly against RSV, KSHV, CMV, DENV, CHIKV, TBEV, VSV, ZIKV and/or HCV, preferably against DENV, which may be measured using methods known in the art. For example, to test for the anti-viral activity of labyrinthopeptin derivatives of the invention, the labyrinthopeptin derivative of the invention may be added to cells (e.g. Huh-7.5 cells). Then, the cells may be infected with the virus to be tested (e.g. RSV, KSHV, CMV, DENV, CHIKV, TBEV, VSV, ZIKV and/or HCV, preferably DENV).

The amount of virus-positive cells may be evaluated by immunocytochemistry. For example, a primary antibody directed against the virus and a secondary antibody that has a conjugated fluorophore may be applied. The number of total cells may be determined by counting DAPI-stained nuclei. Thus, the percentage of virus-positive cells may be calculated. The obtained result is preferably compared to non-infected cells.

Particularly, the terms "labyrinthopeptin derivative(s) of the (present) invention", "labyrinthopeptin derivative(s) provided herein", and "herein provided labyrinthopeptin derivative(s)" refer to a peptide (i.e. compound) that comprises or consists of the amino acid sequence (from N- to C-terminus)

wherein if $R_1$ is H, then $R_2$ is not H.

The amino acid sequence of SEQ ID NO: 1 starts with the N-terminus and ends with the C-terminus, i.e. the sequence of SEQ ID NO: 1 is displayed from N- to C-terminus.

Preferred amino acids for the positions $X_1$, $X_2$, $X_3$, $X_4$, $X_5$, $X_7$ and $X_8$ are described herein above. In SEQ ID NO: 1 "—" is a chemical bond. If "—" is placed between "X" and "X" (e.g. $X_1$-$X_2$, $X_3$-$X_4$, $X_4$-$X_5$, or $X_6$-$X_7$) or between "X" and "Lab" (e.g. "Lab-$X_1$", "$X_2$-Lab", "Lab-$X_3$", "$X_5$-Lab", "Lab-Cys", "Lab-$X_6$", "$X_7$-Lab", "Lab-$X_8$"), than "—" is preferably a peptide bond/linkage. "—S—S—" is a disulfide bridge (also called SS-bond). "—S—" is a thioether bridge between the β-C-atoms of the two alanine-residues that represent the lanthionine part of Lab.

The labionins at positions 1 and 4 of SEQ ID NO: 1 (counted from the N-terminus) and the labionins at positions 10 and 13 of SEQ ID NO: 1 (counted from the N-terminus)

(SEQ ID NO: 1)

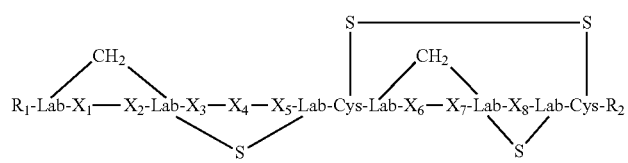

wherein
Lab is labionin
$X_1$ is an amino acid selected from Asn, Asp, and Glu;
$X_2$ is an amino acid selected form Ala, Trp, and Ser;
$X_3$ is an amino acid selected from Val, Leu, and Ile;
$X_4$ is an amino acid selected from Trp and Tyr;
$X_5$ is an amino acid selected from Glu and Asp;
$X_6$ is an amino acid selected from Thr and Ser;
$X_7$ is an amino acid selected from Gly and Pro;
$X_8$ consists of a sequence of 3 to 5 amino acids;
$R_1$ is selected from H, a $(C_2\text{-}C_{12})$alkynyl, a $C(O)$—$(C_2\text{-}C_{12})$alkynyl, a $C(O)$—$O$—$(C_2\text{-}C_{12})$alkynyl, and a $C(O)NH$—$(C_2\text{-}C_{12})$alkynyl; wherein $R_1$ carries the alkynyl group at the terminal position, and
$R_2$ is selected from H, a $[C(O)]$—$NH$—$(C_2\text{-}C_{12})$alkynyl or a $[C(O)]$—$O$—$(C_2\text{-}C_{12})$alkynyl; wherein the moiety $[C(O)]$ is the carbonyl group of the terminal amino acid; wherein $R_2$ carries the alkynyl group at the terminal position;

are linked via a methylene bridge (i.e. —$CH_2$—). In particular, a methylene group links the αC atoms of the labionins at positions 1 and 4. Another methylene group links the αC atoms of the labionins at positions 10 and 13 of SEQ ID NO: 1.

Preferred labyrinthopeptins within the labyrinthopeptin derivative of the present invention are LabyA1 and LabyA2, LabyA1 is most preferred. The amino acid sequence (including the internal bridges) of LabyA1 is shown in SEQ ID NO: 3 above.

Thus, in a preferred aspect, the labyrinthopeptin derivative of the present invention is a derivative of LabyA1 as shown in the following Formula (I):

(Formula (I))

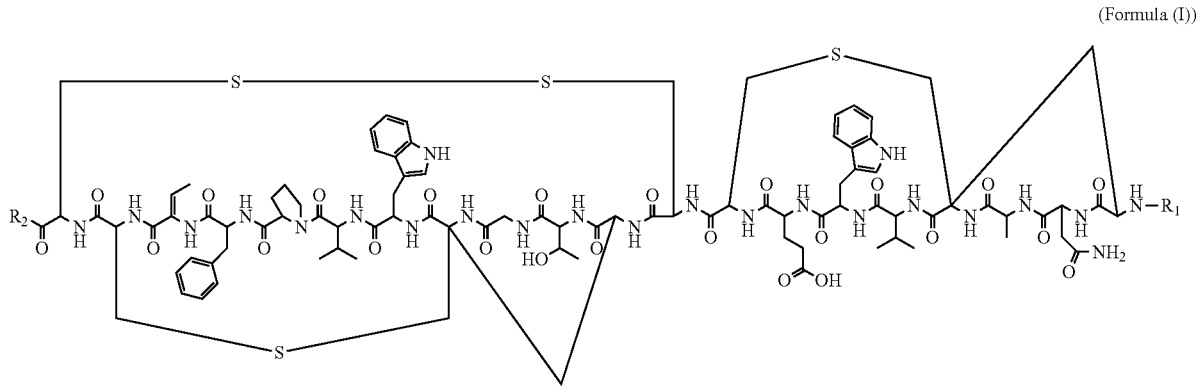

In an even more preferred aspect, the labyrinthopeptin derivative of the present invention is a derivative of LabyA1 as shown in the following Formula (II):

(Formula (II))

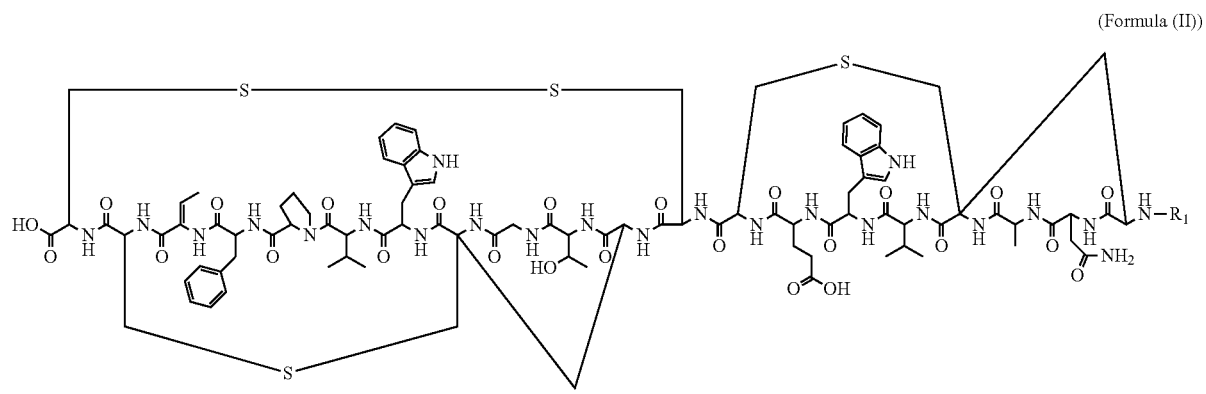

In an even more preferred aspect, the labyrinthopeptin derivative of the present invention is "LabyA1-Hexyn" as shown in FIG. 4.

In another preferred aspect, the labyrinthopeptin derivative of the present invention is a derivative of LabyA2 as shown in the following Formula (III):

In an even more preferred aspect, the labyrinthopeptin derivative of the present invention is "LabyA2-Hexyn" as shown in FIG. 4.

The explanations of $R_1$ and $R_2$ that have been given with respect to SEQ ID NO: 1 apply, mutatis mutandis, also for Formulae I-IV.

(Formula (III))

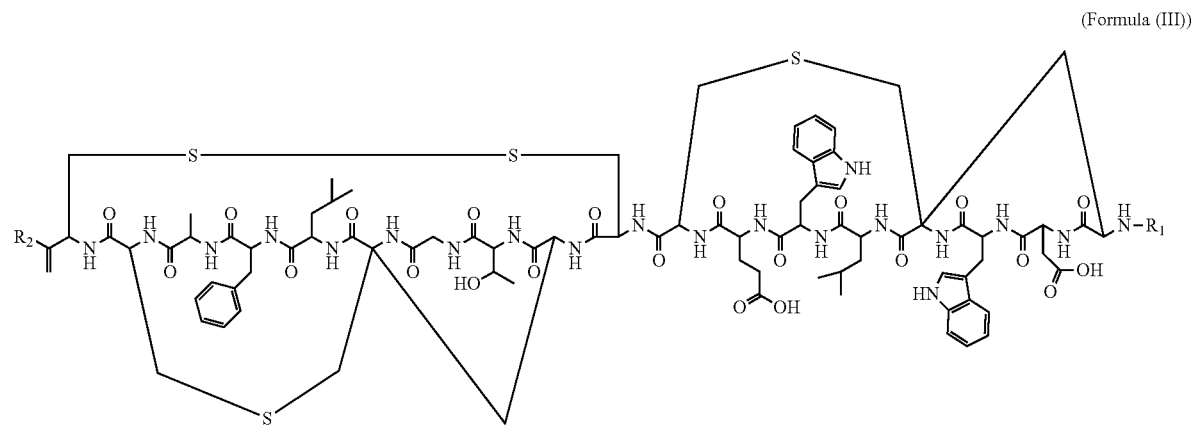

In an even more preferred aspect, the labyrinthopeptin derivative of the present invention is a derivative of LabyA2 as shown in the following Formula (IV):

The labyrinthopeptin derivative of the present invention also include labyrinthopeptin derivatives comprising (in addition to $R_1$ and/or $R_2$) peptides that have at least 80%, (Formula (IV))

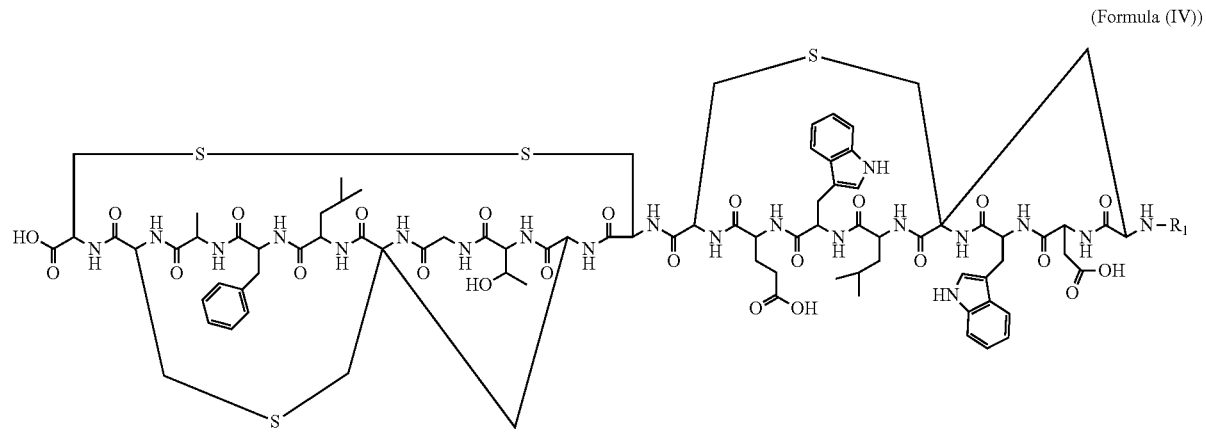

preferably at least 85%, more preferably at least 90%, and even more preferably at least 95% sequence identity to the amino acid sequence as shown in SEQ ID NO: 3, wherein the peptide has at least 50%, preferably at least 90% of the anti-viral activity of LabyA1, particularly against RSV, KSHV, CMV, DENV, CHIKV, TBEV, VSV, ZIKV and/or HCV, more preferably against DENV. The labyrinthopeptin derivative of the present invention further include labyrinthopeptin derivatives comprising (in addition to $R_1$ and/or $R_2$) peptides that have at least 80%, preferably at least 85%, more preferably at least 90%, and even more preferably at least 94% sequence identity to the amino acid sequence as shown in SEQ ID NO: 4, wherein the peptide has at least 50%, preferably at least 90% of the anti-viral activity of LabyA2, preferably against RSV, KSHV, CMV, DENV, TBEV, ZIKV and/or HCV, more preferably against DENV.

The labyrinthopeptin derivatives of the present invention also include peptide analogs and peptidomimetics (or peptide mimetics), that exhibit anti-viral activity, particularly against RSV, KSHV, CMV, DENV, CHIKV, TBEV, VSV, ZIKV and/or HCV.

The labyrinthopeptin derivative of the present invention includes a labyrinthopeptin derivative comprising a peptide of SEQ ID NO: 1 in any stereochemical form, or a mixture of any stereochemical forms in any ratio. Unless otherwise indicated, the chiral centers in the peptide of SEQ ID NO: 1 can be present in the R configuration or in the S configuration. The invention relates to both optically pure compounds and to stereoisomeric mixtures, such as enantiomeric mixtures and diastereomeric mixtures. Preferably, the labyrinthopeptin derivative of the present invention comprises (in addition to $R_1$ and/or $R_2$) a peptide having the stereochemistry of natural LabyA1 or LabA2 as shown in FIG. 3.

The labyrinthopeptin derivatives of the present invention are described herein (e.g. by SEQ ID NO: 1). However, the labyrinthopeptin derivatives of the present invention may also comprises (in addition to $R_1$ and/or $R_2$) the modified labyrinthopeptins as disclosed in Krawczyk, Chemistry & Biology, 2013, 20(1), 111-122; and WO 2013/092672, provided that these modified labyrinthopeptins have anti-viral activity, particularly against RSV, KSHV, CMV, DENV, CHIKV, TBEV, VSV, ZIKV and/or HCV.

In addition, the terms "labyrinthopeptin derivative(s) of the (present) invention", "labyrinthopeptin derivative(s) provided herein", and "herein provided labyrinthopeptin derivative(s)" also relate to a pharmaceutical acceptable salt of a peptide as defined in SEQ ID NO: 1. Thus, also pharmaceutical acceptable salts are included by the term "labyrinthopeptin derivative of the present invention".

"Peptide analogs" (also called "peptidomimetics" or "peptide mimetics") are commonly used in the pharmaceutical art as non-peptide drugs with properties analogous to those of a "template" peptide. The peptide analogs/peptidomimetics replicate the backbone geometry and physicochemical properties of biologically active peptides. Peptidomimetics that are structurally related to biologically active peptides may be used to produce an equivalent or enhanced biological activity (e.g., enhanced therapeutic and/or prophylactic effect). Generally, peptidomimetics are structurally similar to the template peptide, i.e. a peptide that has biological or pharmacological activity and that comprises naturally-occurring amino acids, but have one or more peptide linkages replaced by linkages such as —CH$_2$NH—, —CH$_2$S—, —CH$_2$—CH$_2$—, —CH═CH— (cis and trans), —CH$_2$SO—, —CH(OH)CH$_2$—, —COCH$_2$— etc. Such peptidomimetics can be prepared by methods well known in the art (see, e.g., Spatola, Peptide Backbone Modifications, Vega Data, 1:267, 1983; Spatola, Life Sei. 38:1243-1249, 1986; Hudson, Int. J. Pept. Res. 14:177-185, 1979; and Weinstein, 1983, Chemistry and Biochemistry, of Amino Acids, Peptides and Proteins, Weinstein eds, Marcel Dekker, New-York). Such peptidomimetics may have certain advantages including more economical production, greater chemical stability, enhanced pharmacological properties (e.g., half-life, absorption, potency, efficiency, etc.), reduced antigenicity and others.

The term "amino acid" or "residue" as used herein includes both, L- and D-isomers of the naturally occurring amino acids as well as of other amino acids (e.g., non-naturally-occurring amino acids, amino acids which are not encoded by nucleic acid sequences, synthetic amino acids, etc.). Examples of naturally-occurring amino acids are alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophane (Trp; W), tyrosine (Tyr; Y), valine (Val; V). Post-translationally modified naturally-occurring amino acids are dehydrobutyrine (Dhb) and labionin (Lab). The labyrinthopeptin of the present invention or the labyrinthopeptin that is comprised in the labyrinthopeptin derivative of the present invention may consist of naturally-occurring amino acids. The labyrinthopeptin of the present invention or the labyrinthopeptin that is comprised in the labyrinthopeptin derivative of the present invention may consist of L amino acids. Amino acids are abbreviated herein by the one-letter code or the three-letter code as commonly used in the art and as also set forth hereinabove.

In addition to labionin and dehydrobutyrine, naturally-occurring non-genetically encoded amino acids and synthetic amino acids include, beta-alanine, 3-aminopropionic acid, 2,3-diamino propionic acid, alpha-aminoisobutyric acid (Aib), 4-amino-butyric acid, N-methylglycine (sarcosine), hydroxyproline, ornithine (e.g., L-ornithine), citrulline, tbutylalanine, f-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (Harg), N-acetyl lysine, 2-amino butyric acid, 2-amino butyric acid, 2,4,-diaminobutyric acid (D- or L-), p-aminophenylalanine, N-methylvaline, homocysteine, homoserine, cysteic acid, epsilon-amino hexanoic acid, delta-amino valeric acid, and 2,3-diaminobutyric acid (D- or L-), etc. Unnatural amino acids include, e.g., β-amino acids ($β^3$ and $β^2$), homo-amino acids, 3-substituted alanine derivatives, ring-substituted phenylalanine and tyrosine derivatives, linear core amino acids, and N-methyl amino acids. These amino acids are well known in the art of biochemistry/peptide chemistry.

The term "amino acid" also refers to synthetic amino acids providing similar side chain functionality. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)phenylglycine, D-(trifluoromethyl)-phenylglycine, D-(trifluoromethyl)-phenylalanine, D-p-fluorophenylalanine, D- or L-pbiphenylalanine D- or L-p-methoxybiphenylalanine, D- or L-2-indole (alkyl)alanines, and D- or Lalkylalanines wherein the alkyl group is selected from the group consisting of substituted or unsubstituted methyl, ethyl, propyl, hexyl, butyl, pentyl, isopropyl, iso-butyl, and iso-pentyl. Non-carboxylate amino acids can be made to possess a negative charge, as provided by phosphono- or sulfated amino acids, which are to be considered as non-limiting examples.

The term "amino acid" also includes unnatural alkylated amino acids, made by combining an alkyl group with any natural amino acid. Basic natural amino acids such as lysine and arginine may be substituted with alkyl groups at the amine ($NH_2$) functionality. Yet other substitutions include nitrile derivatives (e.g., containing a CN-moiety in place of the $CONH_2$ functionality) of asparagine or glutamine, and sulfoxide derivative of methionine.

In the labyrinthopeptin of the present invention or the labyrinthopeptin derivative of the present invention all amino acids may be L-amino acids. Alternatively, all amino acids may be D-amino acids. In another alternative, the peptide/peptide compound may comprise a mixture of L- and D-amino acids. For example, the therein provided labyrinthopeptin or labyrinthopeptin derivative may comprise at least one D-amino acid, which is located in the N-terminal and/or C-terminal portion (e.g., within the last 2 or 3 N- and/or C-terminal residues). The presence of one or more D-amino acids typically results in peptides having increased stability (e.g., in vivo) due to decreased susceptibility to protease/peptidase cleavage, but retain biological activity.

The labyrinthopeptin and/or labyrinthopeptin derivative of the present invention may comprise, further to the compound as defined in SEQ ID NOs: 1 or 2, respectively, one or more amino acids covalently linked to the amino and/or carboxy-termini. Thus, the labyrinthopeptin and/or labyrinthopeptin derivative of the present invention may be a chimeric or fusion protein comprising SEQ ID NO: 1 or 2, respectively, linked at its N (i.e. amino)- or C (i.e. carboxy)-terminal end, or both, to another amino acid sequence. Thus, one aspect of the present invention relates to the herein provided labyrinthopeptin (i.e. SEQ ID NO: 2) comprising at its N- and/or C-terminus an amino acid sequence of 0-10 amino acids, preferably of 0-5 amino acids, more preferably of 0-3 amino acids. Similarly, the herein provided labyrinthopeptin derivative may be the herein provided labyrinthopeptin derivative (i.e. SEQ ID NO: 1) comprising at its C-terminus or at its N-terminus an amino acid sequence of 0-10 amino acids, preferably of 0-5 amino acids, more preferably of 0-3 amino acids. For example, the labyrinthopeptin/labyrinthopeptin derivative of the present invention may comprise a peptide moiety and/or an antibody for targeting the labyrinthopeptin/labyrinthopeptin derivative to a particular cell, tissue and/or organ. For example, the peptide moiety and/or antibody may direct the labyrinthopeptin/labyrinthopeptin derivative to the liver (e.g. to hepatocytes). For the treatment of a DENV infection, the peptide moiety and/or antibody may direct the labyrinthopeptin/labyrinthopeptin derivative to cells of the immune system (e.g. to T-cells or Langerhans dendritic cells). For the treatment of an infection with Herpesviridae peptide moiety and/or antibody may direct the labyrinthopeptin/labyrinthopeptin derivative to nerve cells (e.g. to oligodendrocytes or neurons). For the treatment of an infection with RSV the peptide moiety and/or antibody may direct the labyrinthopeptin/labyrinthopeptin derivative to the lung (e.g. to the alveolae). For the treatment of an infection with CHIKV the peptide moiety and/or antibody may direct the labyrinthopeptin derivative to muscle, joint or nerve tissue. For the treatment of an infection with TBEV the peptide moiety and/or antibody may direct the labyrinthopeptin derivative to cells of the central nervous tissue (brain, spinal cord). For the treatment of an infection with ZIKV the peptide moiety and/or antibody may direct the labyrinthopeptin derivative to subcutaneous tissue, the central nervous system, the skeletal muscles or the myocardium. For the treatment of an infection with HCV the peptide moiety and/or antibody may direct the labyrinthopeptin/labyrinthopeptin derivative to the liver (e.g. to hepatocytes).

The labyrinthopeptin or labyrinthopeptin derivative of the invention may comprise two or more compounds of SEQ ID NO: 1 or SEQ ID NO: 2, respectively, covalently linked to one another either directly or indirectly (through a spacer or linker). For example, the labyrinthopeptin of the invention may be a fusion protein comprising two or more linked LabyA1-subunits, two or more linked LabyA2-subunits, or one or more LabyA1-subunits linked to one or more LabyA2-subunits.

Also encompassed in the present invention is a labyrinthopeptin as provided herein, wherein the N- and/or C-terminal amino acids are modified. Similarly, in the labyrinthopeptin derivative provided herein the C-terminal or the N-terminal amino acid may be modified. Possible medications include amidation, acetylation, acylation, covalent attachment of fatty acids (e.g., C6-C18), attachment of proteins such as albumin (see, e.g., U.S. Pat. No. 7,268,113); glycosylation, biotinylation or PEGylation acetylation, acylation, addition of acetomidomethyl (Acm) group, ADP-ribosylation, alkylation, amidation, carbamoylation, carboxyethylation, esterification, covalent attachment of flavin, covalent attachment of a heme moiety, covalent attachment of a nucleotide or nucleotide derivative, covalent attachment of a drug, covalent attachment of a marker (e.g., a fluorescent or radioactive marker), covalent attachment of a lipid or lipid derivative, covalent attachment of phosphatidylinositol, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, and ubiquitination.

As described above, herein the terms "labyrinthopeptin of the (present) invention" and "labyrinthopeptin derivative of the (present) invention" also include a salt of the labyrinthopeptin/labyrinthopeptin derivative as provided herein, e.g., a pharmaceutically acceptable salt of the compound as described in SEQ ID NO: 1 or 2. Pharmaceutically acceptable salts of the labyrinthopeptin/labyrinthopeptin derivative as provided herein are understood as being both their organic salts and their inorganic salts, as are described in Remington's Pharmaceutical Sciences (17th edition, page 1418 (1985)). Because of their physical and chemical stability and their solubility, sodium, potassium, calcium and ammonium salts are preferred, inter alia, for acid groups; salts of hydrochloric acid, sulfuric acid or phosphoric acid, or of carboxylic acids or sulfonic acids, such as acetic acid, citric acid, benzoic acid, maleic acid, fumaric acid, tartaric acid and p-toluenesulfonic acid, are preferred, inter alia, for basic groups. As used herein the term "pharmaceutically acceptable salt" refers to salts of the labyrinthopeptin/labyrinthopeptin derivative of the present invention that retain the anti-viral activity of the parent compound (particularly against RSV, KSHV, CMV, DENV, CHIKV, TBEV, VSV, ZIKV and/or HCV, preferably DENV), and which are not biologically or otherwise undesirable (e.g. not toxic). Such salts can be prepared in situ during the final isolation and purification of the labyrinthopeptin/labyrinthopeptin derivative, or separately prepared by reacting a free base function with a suitable acid.

The labyrinthopeptins of the present invention (e.g. LabyA1 and/or LabyA2) may be produced as follows. The fermentation of biomass from the publicly available type strain *Actinomadura namibiensis* (DSM 6313) may be performed as described before (Meindl, 2010, Angew Chem Int Ed Engl 49: 1151-1154). Afterwards, biomass from the fermenter may be suspended in water (e.g. 2 L), extracted with acetone (e.g. 2×2 L) and methanol (e.g. 1×2 L). Then, combined organic layers may be evaporated under vacuum. Obtained crude compound may be suspended in water (e.g. 1 L) and extracted with tert-butylmethylether (e.g. 2×1 L). Afterwards, organic layer may be discarded and the aqueous layer may be evaporated to obtain (e.g. 20 g of) crude material. The crude compound may be subjected to purification (e.g. in 2 g batches). Purification may be performed on a flash chromatography system (e.g. Reveleris X2 from GRACE) with a C18-WP (40 g, 20μ) column using acetonitrile in water (10-90%) with 0.1% HCOOH as eluents. After the purification, the amount of crude mixture of the labyrinthopeptins of the invention (e.g. of LabyA1 and/or LabA2) may be reduced to 2 g which may further be purified by reverse-phase HPLC using a Gemini 5μ C18 column (dimension: 250 mm×20 mm) with acetonitrile in water (10-90%) with 0.1% HCOOH as eluents. Peaks may be fractionated based on the UV detection at 220 nm. Collected desired compounds (i.e. the labyrinthopeptin of the present invention) may be lyophilized. This procedure may yield approximately 40 mg of LabyA1 and approximately 6 mg of LabyA2.

The labyrinthopeptin of the present invention may also be produced as described in WO 2013/092672 A2, wherein recombinant production of labyrinthopeptins is disclosed. Thus, the labyrinthopeptin of the present invention may be produced by expression in a host cell comprising a nucleic acid encoding the labyrinthopeptin (recombinant expression). Alternatively, LabyA1 and/or LabyA2 may be isolated from *Actinomadura namibiensis* (i.e. wild-type *Actinomadura namibiensis*) as described in WO 2008/040469 A1, or WO 2009/121483 A1. Therefore, the *Actinomadura namibiensis* strain DSM 6313 as disclosed in WO 2009/121483 A1 or WO 2009/121483 A1 may be used. The labyrinthopeptin of the present invention may also be isolated and purified as described in Meindl (2010, Angew Chem Int Ed Engl 49: 1151-1154). In brief, the labyrinthopeptin of the present invention may be purified by extraction, chromatography and preparative HPLC as a final purification step.

Different labyrinthopeptin species may be separated on the basis of their differing polarities, by means of reversed phase chromatography, for example on MCI (adsorber resin, Mitsubishi, Japan) or Amberlite XAD (TOSOHAAS), or on other hydrophobic materials, for example on RP-8 or RP-18 phases. In addition, the separation can be effected by means of normal-phase chromatography, for example on silica gel, aluminum oxide and the like.

The labyrinthopeptin/labyrinthopeptin derivative of the present invention may also be prepared by chemical synthesis (e.g., solid-phase peptide synthesis). The quality of the labyrinthopeptin/labyrinthopeptin derivative may be checked by UV and NMR spectroscopy.

The labyrinthopeptin derivatives of the present invention (e.g. LabyA1-Hexyn or LabyA2-Hexyn as shown in FIG. 4) may be produced as follows. To a solution of 2-chloro-4,6-dimethoxy-1,3,5-triazine (e.g. 1 mg, 0.006 mmol) in dimethylformamide (e.g. 1 ml), n-methylmorpholine (e.g. 2 μL, 0.015 mmol) may be added at room temperature. After 1 h stirring at room temperature, the compound to be added (e.g. 5-Hexynoic acid if $R_1$ should be hex-5ynoyl; e.g. 0.5 μL, 0.004 mmol) may be added. After 30 minutes of stirring, the non-derivatized labyrinthopeptin (e.g. 6 mg, 0.003 mmol) may be added to the reaction mixture and allowed to stir for 16 h at room temperature. The reaction mixture may be purified by reversed-phase HPLC using a Gemini 5μ C18 column (dimension: 250 mm×20 mm) with acetonitrile in water (10-90%) with 0.1% HCOOH as eluents. Peaks may be fractionated based on the UV detection at 220 nm. The collected derivatized labyrinthopeptin may be lyophilized to yield 2 mg (31.7%). The product may be characterized by high resolution mass spectrometry.

The present invention also provides a nucleic acid encoding the labyrinthopeptin of the present invention, a cell (e.g., a host cell) comprising the above-mentioned nucleic acid and/or a vector. Thus, the invention provides a recombinant expression system, vectors and host cells for the expression/production of the labyrinthopeptin of the invention, using for example culture media, production, isolation and purification methods well known in the art. As indicated above, the labyrinthopeptin of the invention can be purified by techniques of peptide purification well known in the art, such as reverse phase chromatography, high performance liquid chromatography (HPLC), ion exchange chromatography, size exclusion chromatography, affinity chromatography, gel electrophoresis, and the like. For affinity chromatography purification, any antibody which specifically binds the herein provided labyrinthopeptin/labyrinthopeptin derivative may for example be used.

The present invention also provides a pharmaceutical composition comprising the above-described labyrinthopeptin and/or labyrinthopeptin derivative and/or combination. Said pharmaceutical composition further comprises at least one pharmaceutically acceptable carrier and/or diluent. As used herein, the term "pharmaceutically acceptable" (also called "biologically acceptable") refers to materials characterized by the absence of (or limited) toxic or adverse biological effects in vivo. The term "pharmaceutically acceptable carrier and/or diluent" refers to additives commonly used in the preparation of pharmaceutical compositions and includes, for example, solvents, dispersion media, saline solutions, surfactants, solubilizing agents, lubricants, emulsifiers, coatings, antibacterial and antifungal agents, chelating agents, pH-modifiers, soothing agents, buffers, reducing agents, antioxidants, isotonic agents, absorption delaying agents or the like (see, e.g., Rowe et al., Handbook of Pharmaceutical Excipients, Pharmaceutical Press; 6th edition, 2009).

As described above, the herein provided pharmaceutical compositions/labyrinthopeptins/labyrinthopeptin derivatives/combinations can be administered parenterally, for example intravenously, intramuscularly or subcutaneously, e.g. in the form of injection solutions or infusion solutions, microcapsules, implants or rods. The pharmaceutical compositions/labyrinthopeptins/labyrinthopeptin derivatives/combinations of the present invention can also be administered orally, for example in the form of pills, tablets, lacquered tablets, coated tablets, granules, hard and soft gelatin capsules, solutions, syrups, emulsions, suspensions or aerosol mixtures. However, the pharmaceutical compositions/labyrinthopeptins/labyrinthopeptin derivatives/combinations of the present invention may also be administered rectally, for example in the form of suppositories; or percutaneously or topically, for example in the form of ointments, solutions or tinctures; or in other ways, for example in the form of aerosols or nasal sprays.

The pharmaceutical compositions according to the invention are prepared in a manner known per se and familiar to one skilled in the art. For example, pharmaceutically acceptable inert inorganic and/or organic carrier substances and/or additives being used in addition to the labyrinthopeptin(s) of the present invention and/or the labyrinthopeptin derivative(s) and/or combinations of the present invention in any stereochemical form, or a mixture of any stereochemical forms in any ratio, or a pharmaceutical acceptable salt thereof, as described above. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid.

Herein the term "effective dose" refers to an amount effective, at dosages and for periods of time necessary, to achieve the desired anti-viral activity, i.e. the desired prophylactic/therapeutic result (i.e. prevention and/or treatment of the virus infections described above). An effective amount of the herein provided labyrinthopeptin, the herein provided labyrinthopeptin derivative, the herein provided combination or the herein provided pharmaceutical compositions may vary according to factors such as the disease state, age, sex, and weight of the individual. Thus, the dosage regimen may be adjusted to provide the optimum prophylactic/therapeutic response. An effective amount is also one in which any toxic or detrimental effects of the compound are outweighed by the prophylactic/therapeutic beneficial effects. For any particular subject, specific dosage regimens may be adjusted over time according to the individual need and the professional judgment of the person administering or supervising the administration of the compositions.

For example, the pharmaceutical compositions of the present invention may contain about 0.5 to about 90% by weight of the herein provided labyrinthopeptin, the herein provided labyrinthopeptin derivative, or the herein provided combination and/or their physiologically acceptable salts and/or their prodrugs. The amount of the active ingredient (i.e. of the herein provided labyrinthopeptin, the herein provided labyrinthopeptin derivative, or the herein provided combination) in the pharmaceutical compositions provided herein may be from about 0.5 to about 1000 mg, preferably from about 1 to about 500 mg.

The dose of the active ingredients provided herein (i.e. of the herein provided labyrinthopeptin, the herein provided labyrinthopeptin derivative, or the herein provided combination) can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. For example, the daily dose for achieving the desired results (e.g. in an adult weighing about 75 kg) may be from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

In the context of the present invention the concentration of the herein provided labyrinthopeptin, labyrinthopeptin derivative or combination within the body of the subject (i.e. the patient) to be treated may not exceed 50 µM. It is envisaged that after administration of the herein provided labyrinthopeptin/labyrinthopeptin derivative/combination or pharmaceutical composition the concentration of said labyrinthopeptin, labyrinthopeptin derivative, or combination within the body of the subject (i.e. the patient) is between 0.125 µM and 50 µM, preferably between 0.5 µM and 50 µM. This applies in particular if the labyrinthopeptin is LabyA1 or if the labyrinthopeptin comprised in the labyrinthopeptin derivative is LabyA1.

It is envisaged that in the subject to be treated the concentration of the herein provided labyrinthopeptin, labyrinthopeptin derivative or combination is lower than the cytotoxic concentration of the respective compound. For determining the cytotoxic concentration (CC50) of the labyrinthopeptin, labyrinthopeptin derivative or combination as provided herein the following assay may be applied.

Cells (e.g. HEp-2 cells), which stably express the reporter gene of a firefly luciferase (FF-luc), may be seeded in a 96-well plate in media, e.g. in Gibco® Advanced MEM. After 72 h of incubation at 37° C. in the presence of increasing concentrations of the labyrinthopeptin, labyrinthopeptin derivative or combination to be tested (e.g. up to 100 µM), the cells may be lysed and the extinction of the FF-luc (RLU) may be measured. Therefore, a plate luminometer (Berthold) may be used. The number of surviving cells is indirectly proportional to residual luciferase expression.

In addition to the active ingredient (i.e. of the herein provided labyrinthopeptin, the herein provided labyrinthopeptin derivative, or the herein provided combination) and to a carrier and/or a diluent, the pharmaceutical compositions of the present invention can contain one or more additives such as, for example, fillers, disintegrants, binders, lubricants, wetting agents, stabilizers, emulsifiers, preservatives, sweeteners, colorants, flavorings, aromatizers, thickeners, buffer substances, solvents, solubilizers, agents for achieving a depot effect, salts for altering the osmotic pressure, coating agents and/or antioxidants.

The terms "treatment", "treating" and the like are intended to mean obtaining a desired pharmacologic (i.e. anti-viral) effect, e.g., inhibiting viral entry or viral replication. It is envisaged that "treatment" and "treating" means that administration of the herein provided labyrinthopeptin, labyrinthopeptin derivative, combination or pharmaceutical composition to a subject (e.g. a human patient) results in a reduced number of virus-positive cells as compared to a control subject. Said control subject is a subject (e.g. a human patient) that did not receive said labyrinthopeptin, labyrinthopeptin derivative, combination or pharmaceutical composition. Thus, herein terms "treatment" or "treating" relate to a partial or complete cure of an infection with the viruses as mentioned above. As described above, herein a "virus infection" or "viral infection" refers to an infectious disease, i.e. a disease/disorder that is caused by a viral infection. For example, said disease/disorder may be caused by the symptoms of a viral infection. The terms "treatment" or "treating" relate to any treatment of a disease in a subject, particularly in a human; or in case of VSV as well treatment of an animal, preferably cattle, pig or horses, and include inhibiting the disease (i.e. the viral infection), arresting or slowing the development/progression of the disease (i.e. of the viral infection); or relieving the disease (e.g., reducing symptoms associated with/caused by the viral infection). The terms "treatment" or "treating" also include the therapeutic intervention of an asymptotic viral infection, e.g. an asymptotic viral infection with HCV, ZIKV or CMV. Treating an asymptotic viral infection includes, e.g., reducing the amount of virus-positive cells, the amount of virus particles and/or viral replication within the infected subject. The terms "prevention", "preventing" and the like mean that a prophylactic effect is obtained in terms of completely or partially preventing a virus infection or a symptom thereof. It is preferred that the herein provided labyrinthopeptin/ labyrinthopeptin derivative/combination/pharmaceutical composition is used to treat an existing viral infection (and not to prevent the occurrence of a viral infection).

The above-mentioned "prevention" and/or "treatment" comprise administration of the above-mentioned labyrinthopeptin/labyrinthopeptin derivative/combination/pharmaceutical composition in combination with one or more additional active/therapeutic agents, or in combination with any other therapy. The combination of prophylactic/therapeutic agents and/or compositions may be administered or co-administered (e.g., consecutively, simultaneously or at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an aspect of the invention be combined/formulated in a single composition and thus administered at the same time. In another aspect of the invention, the active agent(s) of the present invention is/are used/administered in combination with one or more agent(s) currently used to prevent or treat the disorder in question. Accordingly, in an envisaged aspect of the invention, the labyrinthopeptin/labyrinthopeptin derivative/combination/pharmaceutical composition of the invention is administered/used in combination with an anti-viral therapy. Potential anti-viral therapies that may be used in a co-therapy with the herein provided labyrinthopeptin/labyrinthopeptin derivative/combination/pharmaceutical composition are described herein above.

As used herein, the terms "subject" (also called "patient") is taken to mean a warm blooded animal such as a mammal, for example, a camel, a cat, a dog, a mouse, a guinea pig, a horse, a pig, cattle such as a bovine cow, a sheep and a human. It is preferred that the subject is a mammal. It is most preferred that the subject is a human. Particularly, in the case of an infection with VSV the subject may also be an animal, preferably cattle, a pig or a horse.

In context of the present invention, "identity", "percent identity", or "X % identical" means that amino acid sequences have identities of at least 80%, preferably at least 85%, more preferably at least 90%, and even more preferably at least 95% to the sequence of SEQ ID NO: 3; or at of least 80%, preferably at least 85%, more preferably at least 90%, and even more preferably at least 94% to the sequence of SEQ ID NO: 4, wherein the higher identity values are preferred upon the lower ones. In accordance with the present invention, the term "identity/identities" or "percent identity/identities" in the context of two or more amino acid sequences, refers to two or more sequences that are the same, or that have a specified percentage of amino acids that are the same (e.g., that have at least 80%, preferably at least 85%, more preferably at least 90%, and even more preferably at least 95% identity with the amino acid sequences of SEQ ID NO: 3; or that have at least 80%, preferably at least 85%, more preferably at least 90%, and even more preferably at least 94% identity to the sequence of SEQ ID NO: 4; and being functional, wherein the function comprises anti-viral activity, preferably against RSV, KSHV, CMV, DENV, CHIKV, TBEV, VSV, ZIKV and/or HCV, when compared and aligned for maximum correspondence over a window of comparison, or over a designated region as measured using a sequence comparison algorithm as known in the art, or by manual alignment and visual inspection.

Preferably the described identity exists over a region that is at least about 10 amino acids, preferably at least 15 amino acids, more preferably at least 20 amino acids, and most preferably all amino acids of SEQ ID NO: 3 or 4 in length.

Those having skills in the art will know how to determine percent identity between/among sequences using, for example, algorithms such as those based on CLUSTALW computer program (Thompson, 1994, Nucl Acids Res, 2: 4673-4680) or FASTDB (Brutlag, 1990, Comp App Biosci, 6: 237-245), as known in the art. Also available to those having skills in this art are the BLAST and BLAST 2.0 algorithms (Altschul, 1997, Nucl Acids Res 25: 3389-3402; Altschul, 1993, J Mol Evol, 36: 290-300; Altschul, 1990, J Mol Biol 215: 403-410). For example, BLAST 2.0, which stands for Basic Local Alignment Search Tool BLAST (Altschul, 1997, loc. cit.; Altschul, 1993, loc. cit.; Altschul, 1990, loc. cit.), can be used to search for local sequence alignments. BLAST, as discussed above, produces alignments of both nucleotide and amino acid sequences to determine sequence similarity. Because of the local nature of the alignments, BLAST is especially useful in determining exact matches or in identifying similar sequences. Analogous computer techniques using BLAST (Altschul, 1997, loc. cit.; Altschul, 1993, loc. cit.; Altschul, 1990, loc. cit.) are used to search for identical or related molecules in nucleotide databases such as GenBank or EMBL.

The present invention is further described by reference to the following non-limiting figures and Examples.

The Figures show:

FIG. 1. Chemical structure of (A) lanthionin and (B) labionin

FIG. 2. Chemical structure of dehydrobutyrine

FIG. 3. Chemical structure of LabyA1 (FIG. 3A) and LabyA2 (FIG. 3B) showing their stereochemistry FIG. 4. Chemical structures of LabyA1, LabyA2, LabyA1-Hexyn and LabyA2-Hexyn FIG. 5. Dose-dependent inhibition of CMV infection by Labyrinthopeptins. GFP signals (relative units +/−SD) of cultures of NHDF cells (triplicates) infected with a GFP-expressing CMV (i.e. HCMV) strain and treated with the indicated concentrations of Labyrinthopeptins A1 and A2 were measure at day 4 post infection. The IC50 values of the substances were calculated using Graphpad Prism nonlinear fit log (inhibitor) vs. response (three parameters) analysis. One representative result of two experiments is shown.

Figure 6:
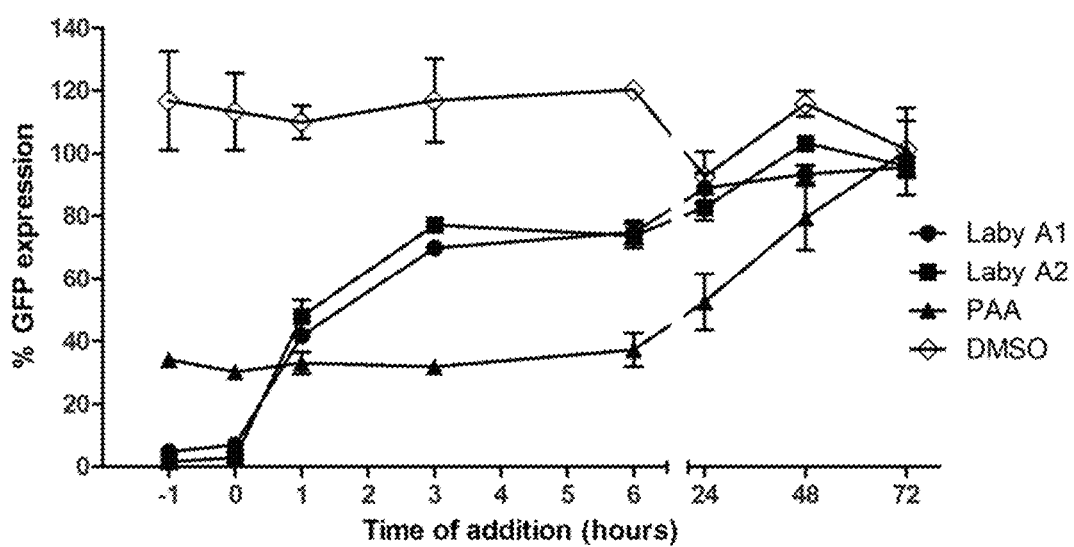

FIG. 6. Labyrinthopeptins inhibit CMV infection in an early phase. NHDF cells were infected with a GFP-expressing CMV strain and test compounds were added at the indicated time points. At 96 hpi the GFP expression in cells of infected cultures (triplicates) was measured. The concentrations of Laby A1 and A2 were 3 µM and 7 µM, respectively. Data are means (+/−SD) of values measured in triplicate cultures. Representative data from one of two experiments are shown.

FIG. 7. Mode of action of Labyrinthopeptins. CMV particles or NHDF cells were preincubated with Labyrinthopeptins, PAA or DMSO for 1 h or remained untreated. The media of the samples were then diluted 16-fold, below the concentration of Labyrinthopeptins found to be effective in previous experiment, followed by CMV inoculation for 3 h and finally replacement with new medium. For control cultures were permanently treated with an effective dose of the substances or 16-fold diluted concentrations. EGFP expression of the cells (means from five replicates) was measured at 4 d p.i. The experiment was repeated 3 times with similar results.

Figure 8:
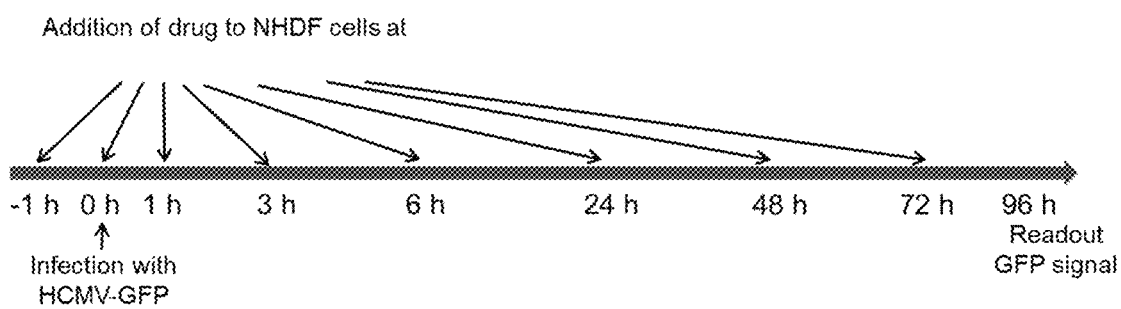

FIG. 8. Scheme depicting the design of the TOA experiment.

Figure 9:
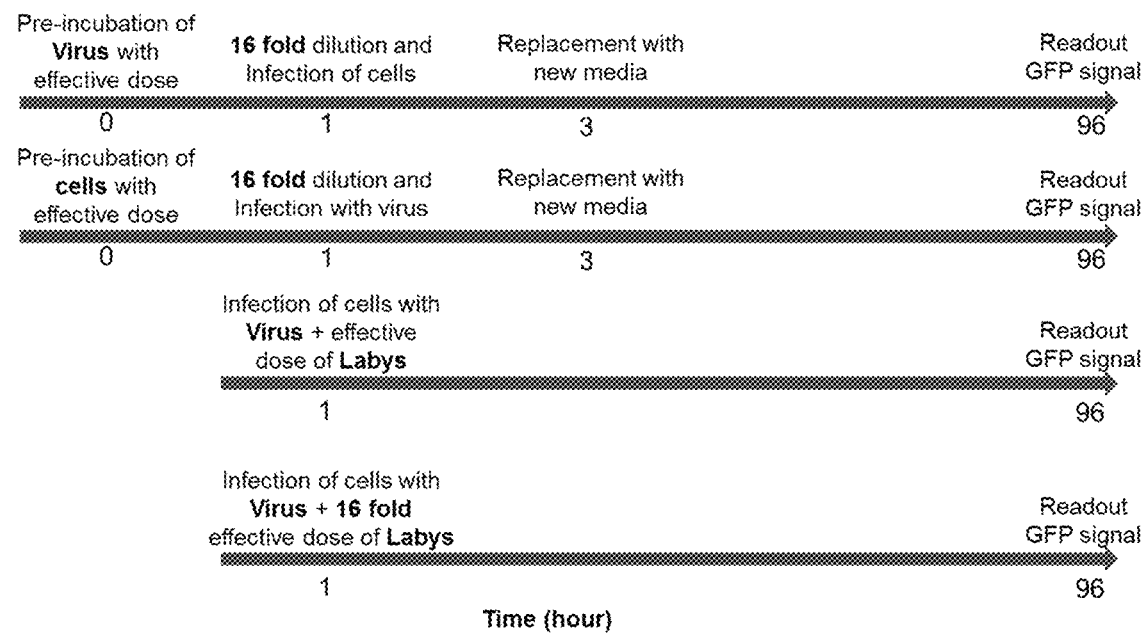

FIG. 9. Outline of the Mode of action assay.

Figure 10:
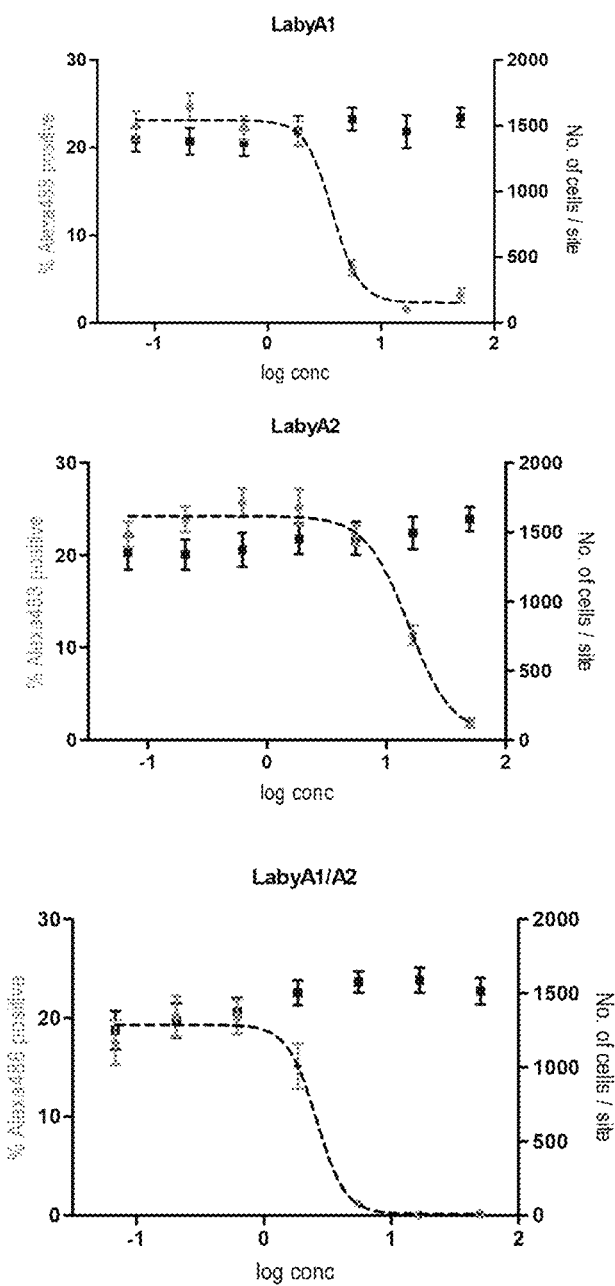

FIG. 10. Synergistic effects of Labyrinthopeptins A1 and A2 on DENV infection. Huh-7 cells were incubated in the presence of varying concentrations of Laby and after 30 min subjected to DENV. 48 h post-infection the number of DENV-positive cells was determined by evaluating DENV-envelope protein expression (AlexaFluor™488-immunostained) via high-content fluorescence imaging. The number of total cells was determined by evaluating DAPI-stained nuclei. $IC_{50}$-values indicate that LabyA1 ($IC_{50}$=3.7 µg/ml) is a more potent inhibitor of viral infection than LabyA2 ($IC_{50}$=15.4 µg/ml). When LabyA1 and LabyA2 were applied in a 1:1 combination, their anti-viral activity is further improved ($IC_{50}$=2.6 µg/ml). (Values are ±SEM; n=5)

Figure 11:
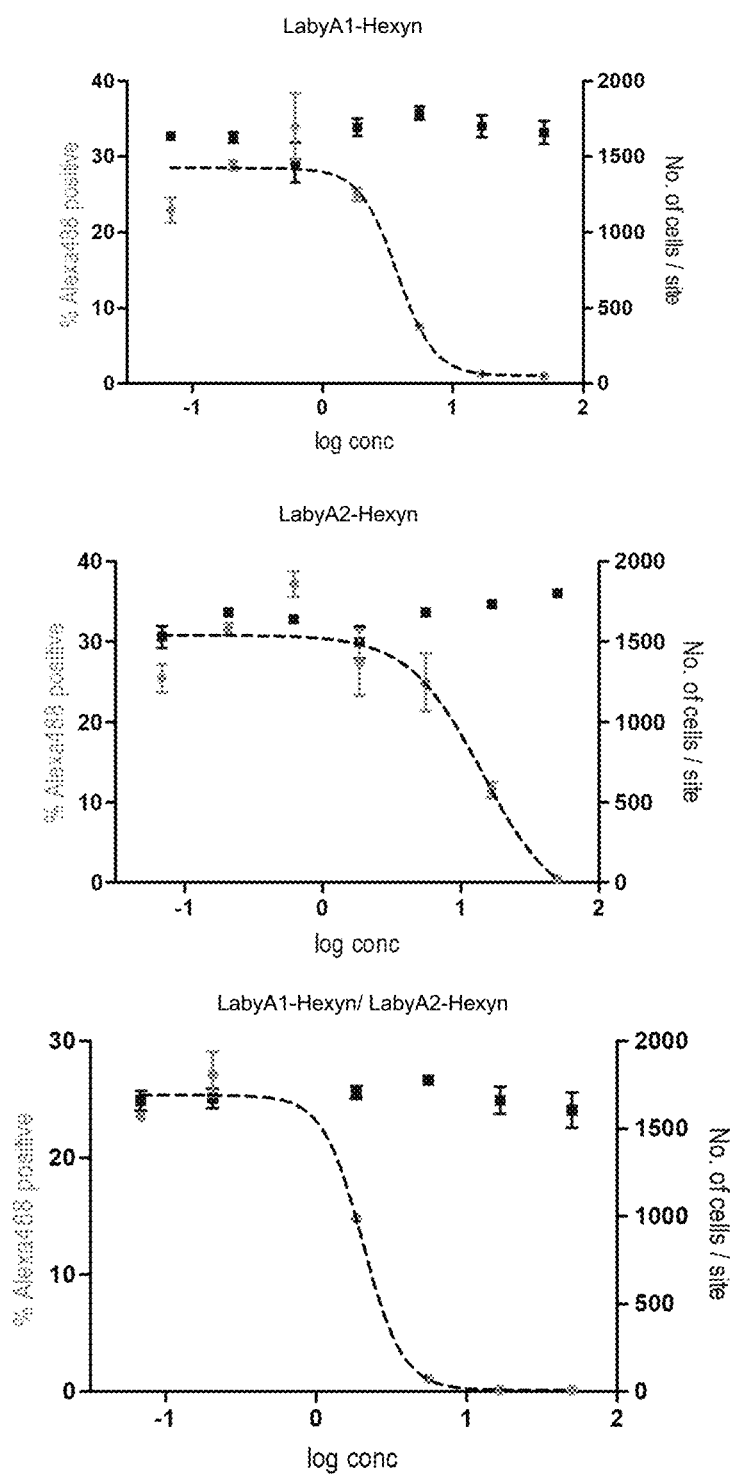

FIG. 11. Laby-Hexyn derivatives retain the anti-DENV activity. Huh-7 cells were incubated in the presence of varying concentrations of Laby-Hexyn derivatives and after 30 min subjected to DENV. 48 h post-infection the number of DENV-positive cells was determined by evaluating DENV-envelope protein expression (AlexaFluor™488-immunostained) via high-content fluorescence imaging. The number of total cells was determined by evaluating DAPI-stained nuclei. $IC_{50}$-values indicate that Laby-Hexyn derivatives retain their anti-DENV activity: $IC_{50}$ (LabyA1-Hexyn) =3.7 µg/ml, $IC_{50}$ (LabyA2-Hexyn)=14.2 µg/ml, $IC_{50}$ (1:1 combination of LabyA1-Hexyn/LabyA2-Hexyn)=2.0 µg/ml. (values are ±SEM; n=3)

Figure 12:
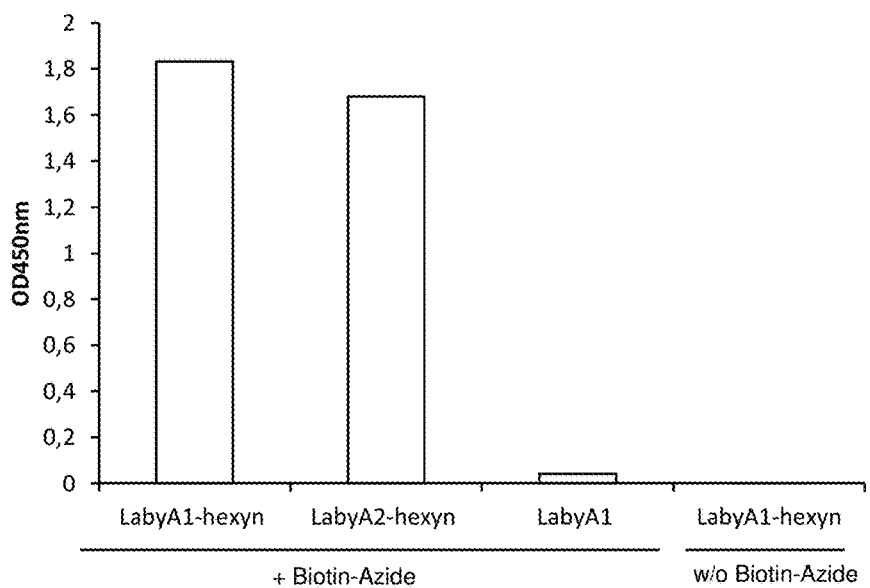

FIG. 12. Dipolar cycloaddition of Biotin-Azide to immobilized Laby-Hexyn derivatives in vitro. 2 µg of Laby-derivatives were immobilized on a Nunc Maxisorp 96 well plate. After blocking with 1% BSA in PBS reaction mix for dipolar cycloaddition with or without Biotin-azide was applied for 2 h. Subsequently success of the reaction was checked by incubating wells with Avidin-labeled HRP for 1 h followed by a color reaction induced by addition of substrate solution C [BioLegend]. Color reaction was stopped by addition of 50 µl $H_3PO_4$ (1 M) and $OD_{450nm}$ was monitored. (Values are ±SEM; n=2)

Figure 13:
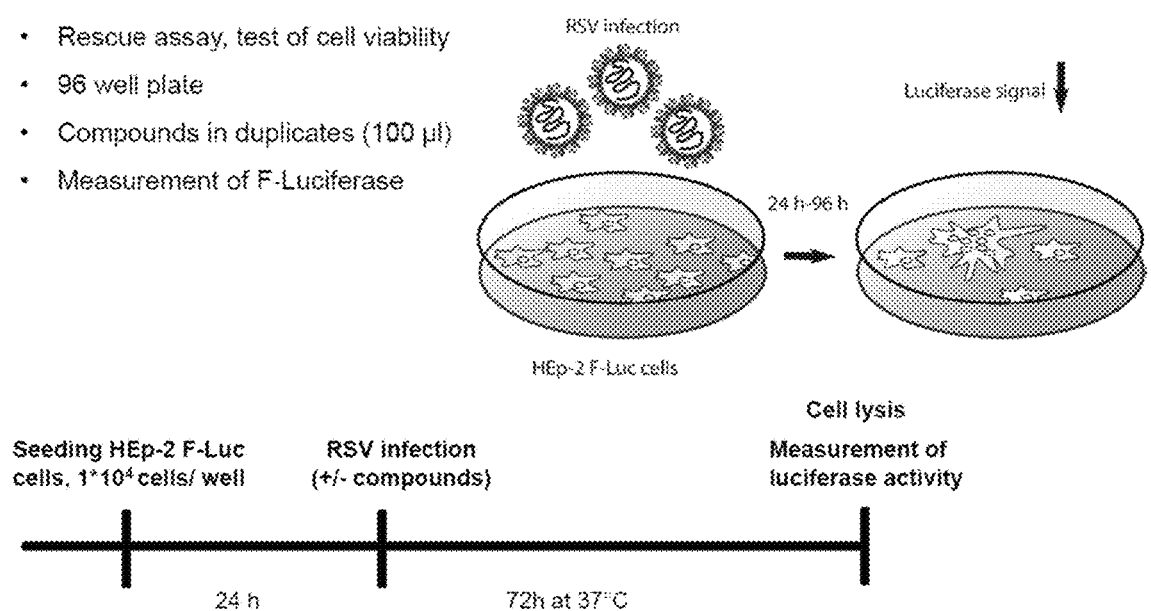

FIG. 13. Schematic representation of the screening system of Example 4.

Figure 14:
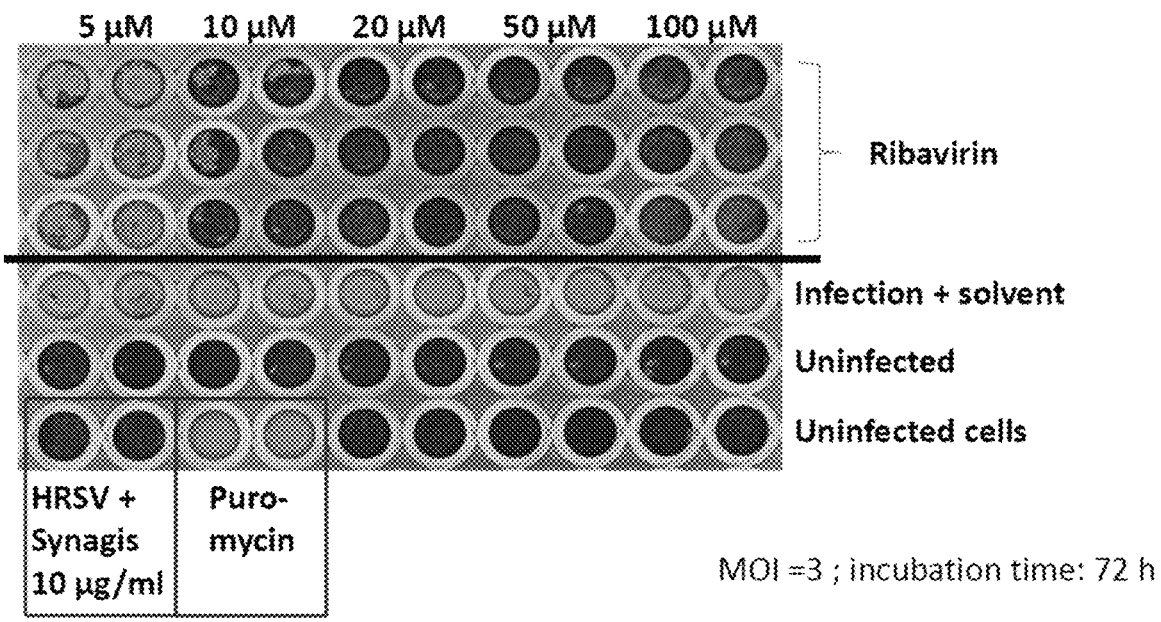

FIG. 14. Assay validation of the screening system of Example 4. Cell survival is assessed by staining with crystal violet.

FIG. 15. Assay validation of the screening system of Example 4. Cell survival in the presence of RSV and ribavirin is shown.

FIG. 16. Labyrinthopeptins inhibit RSV induced cell death and RSV infection. A: Cell survival in the presence of RSV and LabyA1; B: cell survival in the presence of RSV and LabyA2. C: Labyrinthopeptins inhibit RSV infection.

Figure 17:
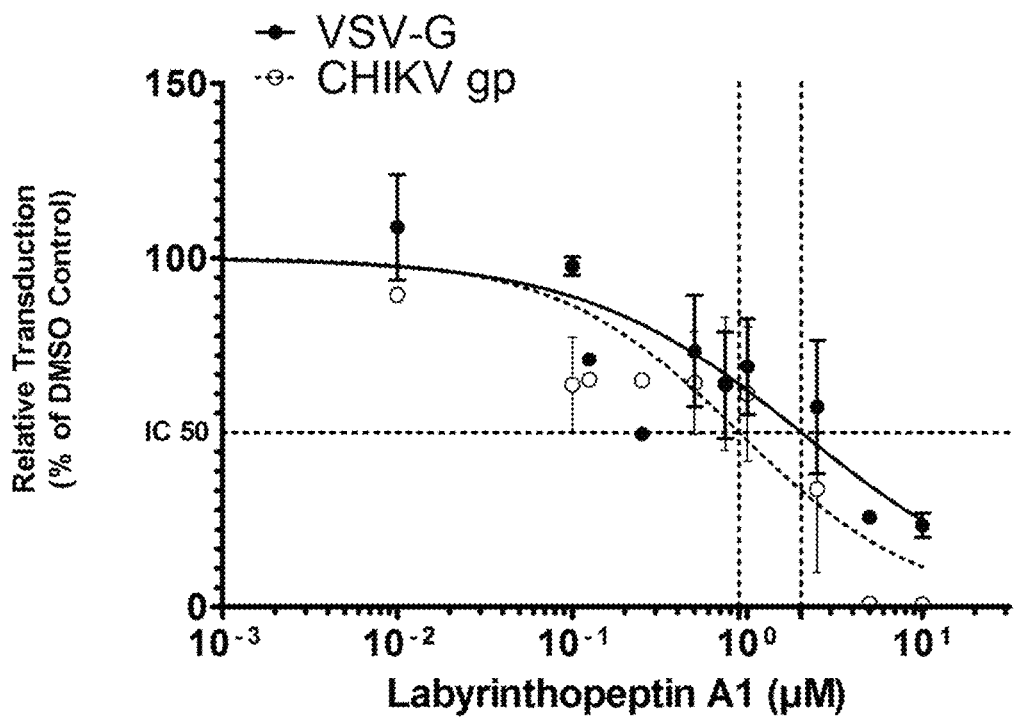
Figure 17:
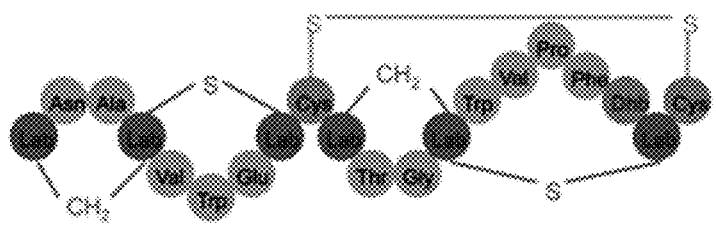

FIG. 17. A: Characterization of the susceptibility of the chikungunya virus glycoprotein-mediated and the VSV-glycoprotein-mediated cell entry process to pharmacological and immunological inhibition and cellular restriction. B: Labyrinthopeptin A1.

Figure 18:
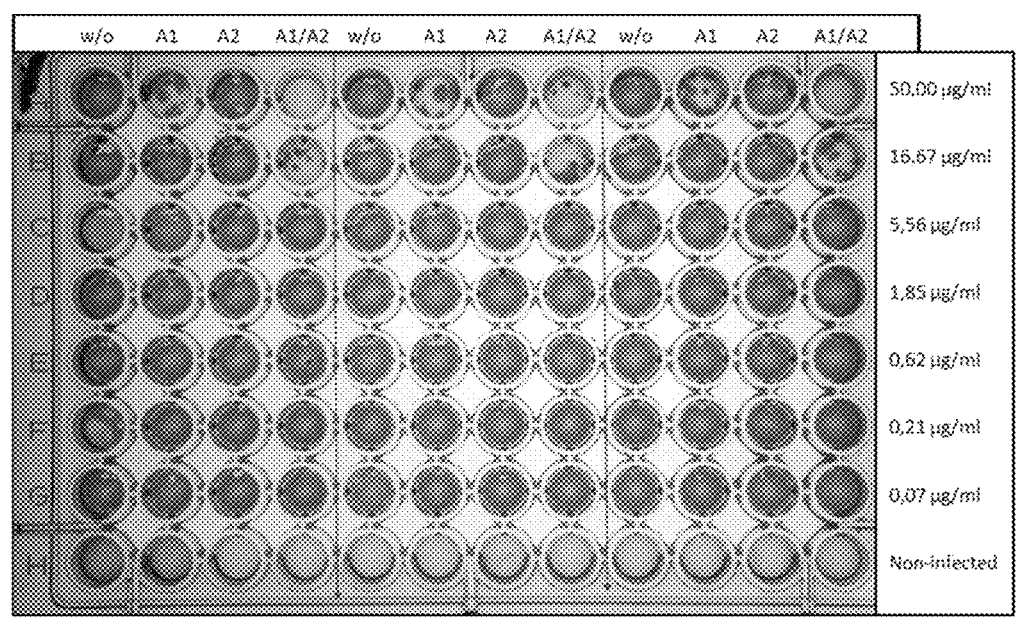

FIG. 18. Effects of labyrinthopeptins on TBEV infection.

Figure 19:
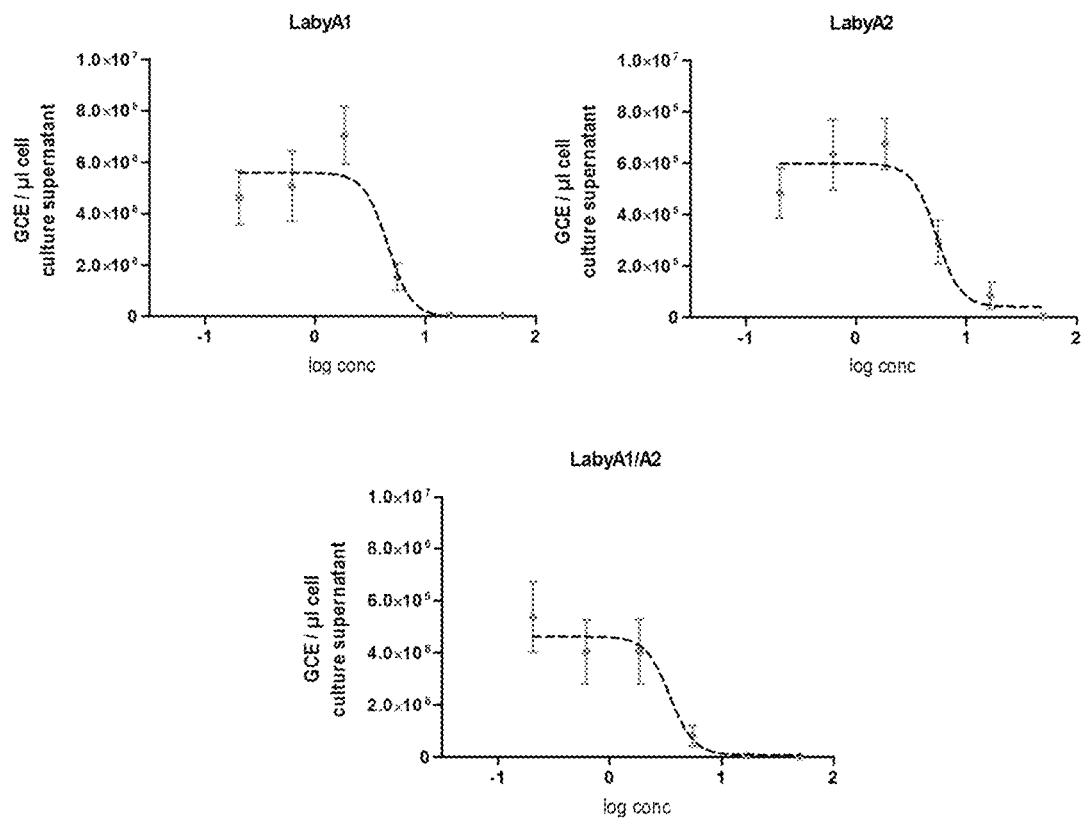

FIG. 19. Effects of labyrinthopeptins on ZIKV infection.

Figure 20:
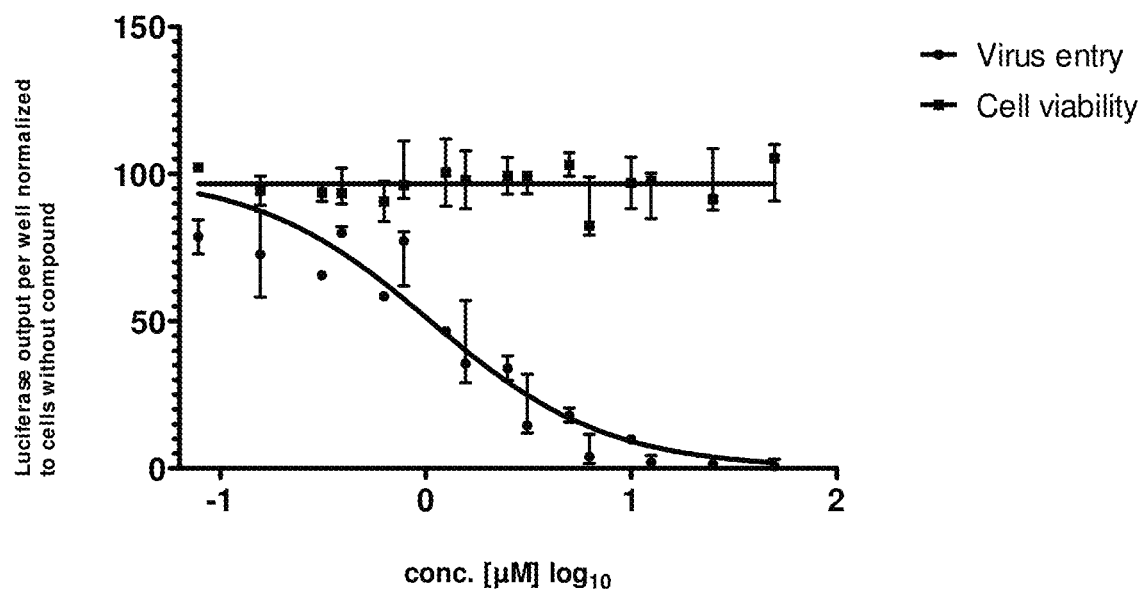
Figure 20:
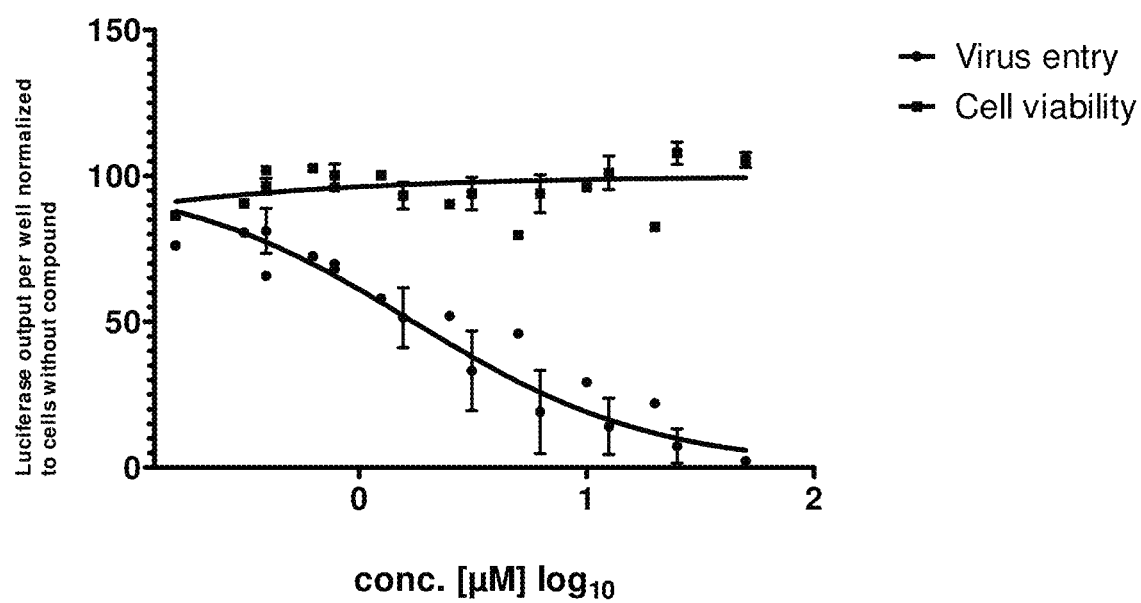

FIG. 20. Effects of labyrinthopeptins on HCV infection. A: Labyrinthopeptin A1 antiviral activity against HCV JcR2a. B: Labyrinthopeptin A2 antiviral activity against HCV JcR2a.

Figure 21:
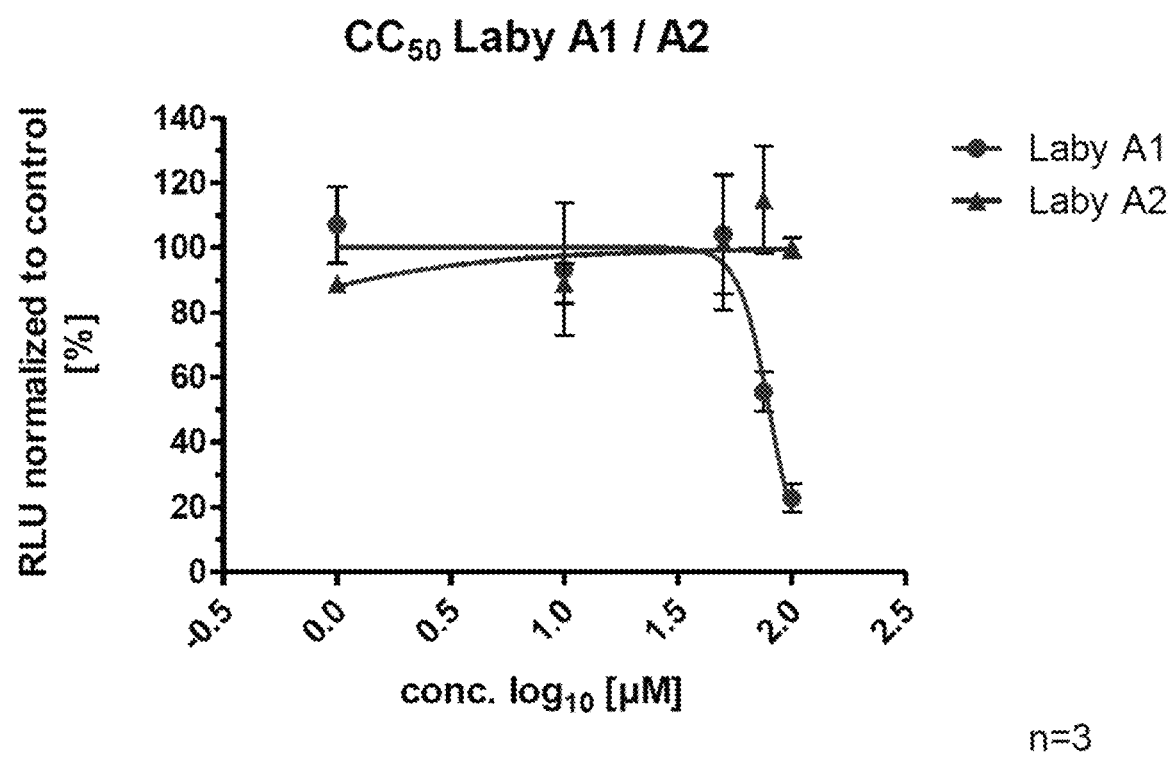

FIG. 21. Cytotoxic concentration (CC50) of Labyrinthopeptin A1 and A2.

The Examples illustrate the invention.

Example 1: Materials and Methods

Dose Response Assay

The antiviral assay is based on the inhibition of CMV-driven GFP expression in NHDF cells. Briefly, NHDF cells (~$1.6 \times 10^4$ per well) were seeded in 96-well plates 1 day prior to infection. Various concentrations of Labyrinthopeptin A1 (final conc. 10, 5, 2, 1 and 0.5 µM) and Labyrinthopeptins A2 (final conc. 15, 10, 5, 2 and 1 µM) were dispensed to the cells to a total volume of 200 µl/well in triplicates. PAA (180 µM) was added as positive control. DMSO was added to either infected cells or uninfected cells with the highest concentration as done with the substances added to cells, as a control for substances which were diluted in DMSO. After 1 h of incubation, the GFP-expressing CMV (i.e. HCMV) strain pHG-1 (Borst, J. Virol. 2005 (79): 3615-26; herein called HT8-GFP), which is based on the CMV (i.e. HCMV) laboratory strain AD169, was added to cells at an MOI of 0.5 and cells were incubated for another 4 days. At 4 dpi the media were removed from the wells and cells were fixed with 3% PFA and washed with PBS followed by adding PBS before measurement. GFP expression from the cells was measured using a BioTek Synergy 2; the protocol for excitation wavelength was set to 485/20 nm and the emission wavelength was 516/20 nm.

Time-of-Drug-Addition (TOA) Experiment

The TOA experiment was performed using $1.6 \times 10^4$ NHDF cells per well in 96 well plates. Labyrinthopeptin A1 (3 µM), A2 (7 µM), DMSO (0.1%) or PAA (180 µM) were added to the cultures at −1, 0, 1, 3, 6, 24, 48, 72 hours of addition of the virus. Cells were infected with HT8-GFP at a multiplicity of infection (MOI) of 0.5 at 0 h. At 96 hpi GFP expression of cells was measured above.

Mode of Action Assay $8 \times 10^3$ PFU of the HT8-GFP expressing AD169 strain and $1.6 \times 10^4$ NHDF cells/well were pre-incubated with 3 µM and 7 µM of TOA LabyA1 and A2, respectively for 1 h and then diluted 16-fold before adding them to cells or infecting with virus in 5 wells. The media was replaced with new media after 3 h of incubation and for controls, viruses and cells were pre-incubated with DMSO (highest concentration of substances) and PAA (180 µM) for 1 h followed by diluting them 16-fold and adding to wells for 3 hours, and then exchanged with new media.

Dose-Dependent Effects of Labyrinthopeptins on KSHV Infection $3 \times 10^4$ HEK 293 cells were seeded in growth medium (DMEM; 10% FBS) onto a 96 well plate and incubated for 24 h at 37° C. and 5% $CO_2$. After removal of the medium, 180 µl growth medium together with 20 µl of a solution of KSHV (produced from cell line BJAB-rKSHV (Kati, J Virol. 2013, 87(14):8004-16; Kati, J Virol Methods. 2015; 217:79-86) at an MOI of 0.01 were applied to each well. Simultaneously the indicated amounts of LabyA1 or LabyA2 were added. After 48 h of incubation, the GFP expressing HEK 293 cells were counted under a fluorescence microscope. The data points given in the figures are means of triplicates. The results are shown in Table 4, below.

Dose Response Assay

Huh-7.5 cells ($3\times10^4$ per well) were seeded in black 96-well optical-bottom plates [Nunc] in full growth medium one day prior to infection. After washing with PBS, 40 µl assay medium (5% FBS) was added to cells containing either Laby A1, Laby A2 (final conc. 50, 16.7, 5.56, 1.85, 0.62, 0.21, 0.069 µg/ml) or a combination of Laby A1 and Laby A2 (25, 8.3, 2.8, 0.93, 0.31, 0.10, 0.034 µg/ml each). Treatments were run in doublets. PBS served as a control. After 30 min of incubation, cells were infected with Dengue Virus (Type 2 New Guinea C) at an MOI of 0.5 to give a final volume of 60 µl/well. After 2 h incubation at room temperature cells were washed with PBS and 100 µl assay medium was added per well. Infected cells were incubated for another 48 h. Hereafter media were removed from the wells and cells were fixed with 4% PFA. Fixed cells were washed extensively with PBS and permeabilized with 0.25% TritonX-100 for 5 min. After blocking with 5% FB in PBS primary antibody was applied (Anti-Dengue Virus E glycoprotein antibody [DE1] (ab41349) [Abcam], 1:100 diluted in 5% FBS/PBS) for 2 h. After washing secondary antibody (Alexa Fluor® 488 Goat Anti-Mouse IgG (H+L) [Life Technologies], 1:1000 diluted in 5% FBS/PBS) was applied for 1 h. Finally, cells were stained with DAPI (500 ng/ml in PBS) for 5 min.

Fluorescent cells were analyzed by high-content imaging using the automated microscope ImageXpressMicro [Molecular Devices] and the MetaXpress-software. The excitation wavelengths were set to 360 nm (DAPI) and 485 nm (Alexa Fluor488) and the emission wavelengths were set to was 460 nm (DAPI) and 516 nm (Alexa Fluor488). Images of six sites/well were acquired (2 columns, 89 µm spacing; 3 rows, 67 µm spacing). The number of total cells/site was determined by automatically counting DAPI-stained nuclei. The percentage of DENV-positive cells was calculated by automatically evaluating the number of Alexa Fluor 488-positive cells in relation to the total cell number. Values obtained from the six sites were averaged and plotted onto a semi-logarithmic X/Y-chart. $IC_{50}$-values were calculated by non-linear regression.

Synthesis of Laby A1-Hexyn Derivative

To a solution of 2-chloro-4,6-dimethoxy-1,3,5-triazine (1 mg, 0.006 mmol) in dimethylformamide (1 ml), n-methylmorpholine (2 µL, 0.015 mmol) was added at room temperature. After 1 h stirring at room temperature, 5-Hexynoic acid (0.5 µL, 0.004 mmol) was added. After 30 minutes of stirring, Labyrinthopeptin A1 (6 mg, 0.003 mmol) was added to the reaction mixture and allowed to stir for 16 h at room temperature. The reaction mixture was purified by reversed-phase HPLC using a Gemini 5µ C18 column (dimension: 250 mm×20 mm) with acetonitrile in water (10-90%) with 0.1% HCOOH as eluents. Peaks were fractionated based on the UV detection at 220 nm. Collected desired compound was lyophilized to yield 2 mg (31.7%). The product was characterized by high resolution mass spectrometry.

HRMS (Q-tof): Calculated for $C_{98}H_{126}N_{23}O_{26}S_4$ $[M+H]^+$ 2168.8127, found 2168.7821

Synthesis of Laby A2-Hexyn Derivative

To a solution of 2-chloro-4,6-dimethoxy-1,3,5-triazine (1 mg, 0.006 mmol) in dimethylformamide (1 ml), n-methylmorpholine (2 µL, 0.015 mmol) was added at room temperature. After 1 h at room temperature 5-Hexynoic acid (0.5 µL, 0.004 mmol) was added. After 30 minutes of stirring, Labyrinthopeptin A2 (6 mg, 0.003 mmol) was added to the reaction mixture and allowed to stir for 16 h at room temperature. The reaction mixture was purified by reversed-phase HPLC using a Gemini 5µ C18 column (dimension: 250 mm×20 mm) with acetonitrile in water (10-90%) with 0.1% HCOOH as eluents. Peaks were fractionated based on the UV detection at 220 nm. Collected desired compound was lyophilized to yield 1.5 mg (23.8%). The product was characterized by high resolution mass spectrometry.

HRMS (Q-tof): Calculated for $C_{91}H_{117}N_{20}O_{25}S_4$ $[M+H]^+$ 2017.7381, found 2017.7376

Dipolar Cycloaddition of Biotin-Azide to Immobilized Laby-Hexyn Derivatives

All subsequent washing steps were performed with three times with 200 µl of PBS. 2 µg of either LabyA1-Hexyn, LabyA2-Hexyn or LabyA1 were diluted in Coating Buffer A [BioLegend] and adsorbed in triplets for 16 h at 4° C. to a 96 well plate (Nunc Maxisorp). After washing with PBS wells were blocked with 1% BSA (w/v) in PBS (blocking buffer) for 1 h at room temperature. Wells were again washed with PBS and 100 µl cycloaddition reaction mix (2 mM $CuSO_4$, 5 mM Sodium ascorbate, 100 µM Biotin-azide [Azide-PEG3-Biotin conjugate, Sigma], diluted in blocking buffer) were applied. Cycloaddition reaction mix without Biotin-Azide served as a control. The reaction was performed for 2 h at room temperature. After washing with PBS, wells were incubated with 100 µl blocking solution containing Avidin-labeled Horse radish peroxidase (HRP) [BioLegend] for 1 h. Finally wells were washed with PBS and 100 µl substrate solution C [BioLegend] was applied to each well. Color reaction was stopped after 15 min by addition of 50 µl $H_3PO_4$ (1 M). $OD_{450nm}$ was determined using an automated plate reader [Biotek].

Chikungunya Virus Assay

HEK293T cells were seeded into a 96-well plate ($2\times10^4$ cells/well) and cultured under standard conditions. On the next day VSV-G- and CHIKV gp-pseudotyped lentiviral particles encoding luciferase were treated with indicated concentrations of Labyrinthopeptin A1 or DMSO. Cells were transduced with Labyrinthopeptin A1-treated or DMSO-treated vector particles and cultured for 48 h. Afterwards, luciferase activity in transduced cells was measured luminometrically. IC50 values were calculated using GraphPad Prism 5; see Example 5 and FIG. 17.

Example 2: Effect of Labyrinthopeptins A1 and A2 on CMV Infection

Dose-Dependent Effects of Labyrinthopeptins on CMV Infection

To determine a potential effect of Labyrinthopeptins on CMV (i.e. HCMV) infection, cultures of normal human dermal fibroblasts (NHDF) were treated with various concentrations of Labyrinthopeptins A1 and A2 one hour before infection with a GFP-expression CMV strain at a multiplicity of infection of 0.5 PFU/cell. 4 days later GFP expression of the cells was measured as readout for viral gene expression. DMSO-treated cells (DMSO is the diluent for the Labyrinthopeptins) and untreated cells served as positive controls for the infection, and non-infected cells as negative control. Treatment of infected cell cultures with phosphonoacetic acid (PAA) was used a positive control for inhibition of viral replication.

The Labyrinthopeptins inhibited virus-driven GFP expression in cells inoculated with CMV in a dose-dependent manner (FIG. 5). The IC50 values for Labyrinthopeptins A1 and A2 were approximately 1.3 and 5.4 µM, respectively.

Time Point of the Inhibitory Effect of Labyrinthopeptins During the Life Cycle of CMV To get an idea on which phase of the CMV infection cycle the Labyrinthopeptins exert their effect, a time-of-addition experiment was performed. Labyrinthopeptins A1 and A2 (at a final concentration of 3 and 7 µM, respectively) were added to the cell cultures, either before, concomitantly or subsequently to inoculation with CMV (see FIG. 6). GFP expression as a readout for successful viral infection was measured at day 4 p.i. DMSO-treated cultures served as controls.

The strongest inhibition of viral gene expression (almost complete inhibition) was observed when the substances were added before or concomitantly with virus inoculation of the cultures. About 50% inhibition occurred when the compounds were added 1 h post inoculation and approximately 25% inhibition upon addition at 3 and 6 h p.i. At later times points viral infection could be inhibited only minimally.

These results suggest that the labyrinthopeptins act on an early step of viral infection or possibly directly on viral particles. One has to point out that in the experiment shown, entry of CMV into the cells is not synchronized. Although a substantial portion of the inoculated virus has entered the cells one hour p.i., other particles could remain attached to the cell surface and enter the cells only subsequently.

Putative Effect of Labyrinthopeptins A1 and A2 on Virus Particles

To learn whether the substances act primarily on the virus particles or on cells, pretreatment was performed using concentrations of Labyrinthopeptins A1 and A2 3 µM and 7 µM of LabyA1 and A2, respectively) that in the previous experiments were found to be effective (>98% inhibition of infection).

Following incubation for 1 h the virus sample or the medium in the cell cultures were diluted 16-fold, resulting in a concentration of the compounds which according to the dose-response curve (cf. FIG. 5) would not exert an effect. Pretreated virus was then added to cells (FIG. 7, group "virus pretreated") or untreated virus was added to pretreated cells (FIG. 7, group "cells pretreated"), followed by incubation for 3 h and replacement of the inocula with new media. GFP expression was determined at 96 h p.i. In parallel, cultures were treated with the effective doses of the compounds or 16-fold diluted concentrations concomitantly with CMV inoculation to verify inhibition by the compounds and loss upon 16-fold dilution (FIG. 7, dilution). PAA and DMSO were used as controls.

Upon pretreatment of viruses with Labyrinthopeptins A1 and A2, viral gene expression was inhibited by ~50% and ~90%, respectively. Basically no inhibition was observed upon pretreatment of cells. Treatment of infected cells throughout the infection cycle with high concentrations of Labyrinthopeptins A1 and A2 resulted in nearly 100% inhibition as expected (FIG. 7, group "permanently treated, effective dose), whereas only slight inhibition was seen following permanent treatment with the 16-fold diluted concentration (FIG. 7, group "permanently treated, 16-fold dilution"). PAA—as a soluble substance that acts on the viral DNA polymerase at a later stage of infection—exerted inhibition only when permanently present in the culture medium (to a lesser extent when the 16-fold diluted concentration was applied as expected), but not when it was removed after pretreatment of the virus or cells.

The results suggest that the labyrinthopeptins act primarily on the virus particles. The somehow reduced inhibitory effect upon pretreatment with Labyrinthopeptin A1 compared to the effect seen upon permanent treatment could either indicate that the inhibition is partially reversible or that the substance is additionally effective during the cell attachment or entry phase of CMV.

Example 3: Effects of Labyrinthopeptins A1 and A2 on DENV Infection

Synergisitc Effects of Labyrinthopeptins A1 and A2 on DENV Infection

To determine a potential synergistic effect of Labyrinthopeptins A1 and A2 on DENV-infection a dose response assay was performed. Cultures of Huh-7.5 cells (human hepatocarcinoma cell line) were treated with various concentrations of either Laby A1, LabyA2 or an equivalent combination of LabyA1 and LabyA2 for 30 min. Cells were subsequently infected with DENV (Type 2 New Guinea C) at a MOI of 0.5 PFU for 2 h at room temperature. Unbound viral particles were removed and infected cells were incubated for 48 h. Hereafter cells were fixed using 4% PFA in PBS and immunostained for DENV envelope protein expression. For this purpose, a combination of anti-Dengue Virus E glycoprotein antibody and an Alexa Fluor 488-conjugated secondary antibody was applied. Additionally cell nuclei were stained with DAPI. The number of total cells as well as the percentage of Alexa Fluor 488-positive cells (=DENV positive cells) was determined by high-content fluorescence imaging.

$IC_{50}$-values indicate that LabyA1 ($IC_{50}$=3.7 µg/ml) is a more potent inhibitor of viral infection than LabyA2 ($IC_{50}$=15.4 µg/ml). When LabyA1 and LabyA2 were applied in a 1:1 combination, their anti-viral activity is further improved ($IC_{50}$=2.6 µg/ml) (FIG. 10).

Laby-Hexyn Derivatives Retain the Anti-DENV Activity

To conduct mode of action studies we generated Laby-derivatives carrying an N-terminal Hexyn-group. These can further be derivatized in vitro and in vivo by dipolar cycloaddition e.g. of an azide-labeled fluorophore. To determine the biological activity of Laby-Hexyn derivatives on DENV-infection a dose response assay was performed as depicted above. The $IC_{50}$-values obtained are similar to the $IC_{50}$-values obtained for uncoupled Laby and thus indicate that Laby-Hexyn derivatives retain their anti-DENV activity: $IC_{50}$ (LabyA1-Hexyn)=3.7 µg/ml, $IC_{50}$ (LabyA2-Hexyn)=14.2 µg/ml, $IC_{50}$ (1:1 combination of LabyA1-Hexyn/LabyA2-Hexyn)=2.0 µg/ml (FIG. 11).

Dipolar Cycloaddition of Biotin-Azide to Immobilized Laby-Hexyn Derivatives

To test whether the dipolar cycloaddition works in vitro with Laby-Hexyn derivatives, these were immobilized on 96 well plate (Nunc Maxisorp). 2 µg of either LabyA1-Hexyn, LabyA2-Hexyn or LabyA1 were diluted in Coating Buffer A [BioLegend] and adsorbed in triplets to one well of the 96 well plate for 16 h at 4° C. Cycloaddition reaction of Biotin-azide was performed as given in material and methods. Cycloaddition reaction mix without Biotin-Azide served as a control.

The data demonstrate that the dipolar cycloaddition of Biotin-azide to immobilized Laby-Hexyn derivatives works well indicated by the pronounced $OD_{450nm}$. In contrast, dipolar cycloaddition does not work with non-alkenylated Laby (FIG. 12).

Example 4: Effects of Labyrinthopeptins A1 and A2 on RSV Induced Cell Death and RSV Infection Labyrinthopeptins A1 and A2 Inhibit RSV Induced Cell Death A cell-based screening system was used to determine the antiviral effect of labyrinthopeptin A1 and A2 against the human respiratory syncytial virus (RSV, also called hRSV). A schematic representation of the screening system is depicted in FIG. 13.

HEp-2 cells, which are stably expressing the reporter gene of a firefly luciferase (FF-luc), were seeded in a 96-well plate in 200 µl appropriate media. The incubation time has been set to 72 h at 37° C. with a MOI of 3 to obtain a useful measuring window between uninfected and infected cells. After 72 h the cells have been lysed and the luminescence produced by the FF-luc was measured using a plate luminometer (in RLU). The cells were infected by RSV in the presence of different concentrations of labyrinthopeptin A1 and A2. RSV is a lytic virus and kills infected cells. Therefore, unrestricted infection and spread of RSV will lead to cell death and as a result of this, decrease of luciferase gene expression. The number of surviving cells is indirectly proportional to the virus infection/replication efficiency. In other words, the more cells survive, the less RSV was able to infect cells. Cell survival can be assessed and quantified either by determination of total viable cells (e.g. by staining with crystal violet, which stains remaining cells; compare FIG. 14). Moreover, cell survival is proportional to residual luciferase expression. To validate our assay, we used ribavirin, a guanosine nucleoside analogue, which is known to inhibit RSV replication in cell culture (FIG. 15). The half maximal inhibitory concentration ($IC_{50}$) has been calculated for labyrinthopeptin A1 $IC_{50}$=3.87 µM in 6 independent experiments (FIG. 16A) and for labyrinthopeptin A2 $IC_{50}$=47.93 µM in 3 independent experiments (FIG. 16B).

Labyrinthopeptins A1 and A2 Inhibit RSV Infection

Wild-type RSV (i.e. hRSV) infection and intracellular RSV-P staining was used to determine IC50 of labyrinthopeptin A1 and A2 (see FIG. 16 C).

Therefore, 1×10⁵ HEp 2 cells seeded in a 12-well plate were inoculated for 4 h with the wild-type RSV at a multiplicity of infection (MOI) of 1 on a horizontal shaker. Inoculation was done together with different concentrations of labyrinthopeptin A1 or A2. After 4 h the cells were washed with sterile PBS and incubated at 37° C. 18 hours post infection the cells were detached by trypsinization and fixed in fixation buffer (0.5% paraformaldehyde, 1% fetal calf serum [FCS] in phosphate-buffered saline [PBS]) for 30 min at 4° C. Subsequently, the cells were permeabilized with a saponin-containing permeabilization buffer (0.1% saponin, 1% FCS in PBS) for 20 min at 4° C. Afterwards, the cells were stained for 30 min at 4° C. with an RSV-P-specific antibody (26D6G5C6) diluted 1:500 in permeabilization buffer. Subsequently, the cells were washed with PBS, and bound antibodies were detected by incubation for 30 min at 4° C. with mouse-specific Alexa 488 secondary antibodies (Thermo Fisher Scientific) at a 1:200 dilution in permeabilization buffer. The stained cells were washed twice with PBS and analyzed using an Accuri C6 and FlowJo software.

The half maximal inhibitory concentrations (IC50) have been calculated for labyrinthopeptin A1 IC50=0.39 µM and for labyrinthopeptin A2 IC50=4.97 µM (see FIG. 16 C).

Example 5: Characterization of the Susceptibility of the Chikungunya Virus (CHIKV) Glycoprotein-Mediated and Stomatitis Indiana Virus (VSV) Glycoprotein-Mediated Cell Entry Process to Pharmacological and Immunological Inhibition and Cellular Restriction Here, use is made of lentiviral vectors carrying CHIKV glycoproteins E1 and E2 or VSV glycoprotein on their surface for studying properties of the CHIKV or VSV glycoprotein-mediated entry process and their susceptibility to pharmacological and immunological inhibition, as well as to restriction by cellular antiviral IFITM proteins.

Treatment of 293T cells with Labyrinthopeptin A1 resulted in dose-dependent reduction of transduction efficiency upon challenge with CHIKV glycoprotein-expressing pseudotypes, yielding an $IC_{50}$ value between 0.5-1.7 µM; see FIG. 17. Introduction of sublineage-specific mutations in CHIKV glycoproteins did not grossly modulate the entry efficiency of lentiviral vectors, and all variants remained susceptible to neutralization by a monoclonal antibody targeting CHIKV E2. The capability of cellular IFITM proteins to restrict CHIKV glycoprotein-mediated cell entry of lentiviral vectors was interrogated in 293T cell lines stably expressing individual C-terminal HA-tagged human IFITM proteins. Interestingly, expression of IFITM1-HA, IFITM2-HA and IFITM3-HA on target cells resulted in a 2-fold reduction of transduction efficiency, respectively, as compared to vector-expressing cells. The necessity of appropriate post-translational modification of IFITM proteins, including palmitoylation and ubiquitination of conserved residues, for their antiviral activity, as well as the species-specificity of IFITM proteins' antiviral capacity are currently investigated. Interestingly, selected CHIKV glycoprotein variants seem to display increased susceptibility to IFITM protein-mediated restriction.

The VSV glycoprotein-mediated entry process as well as its susceptibility to inhibition by Labyrinthopeptin A1 was analyzed in the same manner as described for CHIKV, above. Treatment of 293T cells with Labyrinthopeptin A1 resulted in dose-dependent reduction of transduction efficiency upon challenge with VSV glycoprotein-expressing pseudotypes, yielding an $IC_{50}$ value as shown in FIG. 17.

Example 6: Effects of Labyrinthopeptins on TBEV Infection 1.5×10⁴ Vero-B4 cells were seeded in growth medium (DMEM; 10% FBS) onto a 96 well plate and incubated for 24 h at 37° C. and 5% $CO_2$. After removal of the medium, LabyA1, Laby A2 or a 1:1 mixture of LabyA1/LabyA2 was added to the cells in 26.5 µl medium. After 30 min of incubation at 37° C., cells were infected with TBEV (Toro isolate) at a MOI of 0.01 for 1 h. In the resulting total volume of 64 µl per well, top concentration of Laby was 50 µg/ml with serial 3-fold dilutions down to 0.07 µg/ml being applied. After removal of the inoculum, infected cells were cultivated for 3 days in a mixture of Avicel and DMEM. Eventually, infected cells were fixed with 6% Formaldehyde. After permaebilization with TritonX, TBEV-envelope protein was detected by respective primary and HRP-linked secondary antibodies. The enzymatic reaction was performed using TrueBlue Peroxidase substrate. Pictures of cell culture plates were taken with the ChemiDoc Imaging System [BioRad]; see FIG. 18. $IC_{50}$ values were estimated by visual inspection of the wells. In the picture, areas of infection appear black and non-infected areas appear white; see FIG. 18.

The $IC_{50}$ values for LabyA1 were 24.10 µM and 50 µg/ml, respectively; the $IC_{50}$ values for LabyA2 were >25.99 µM and >50 µg/ml, respectively; and the $IC_{50}$ values for the combination of LabyA1 and LabyA2 were 8.34 µM and 16.67 µg/ml, respectively; see Table 4.

Example 7: Effects of Labyrinthopeptins A1 and A2 on ZIKV Infection

Cultures of Huh-7.5 cells (human hepatocarcinoma cell line) were treated with various concentrations of either LabyA1, LabyA2 or an equivalent combination of LabyA1 and LabyA2 for 30 min. Cells were subsequently infected with ZIKV (Strain MR766-NIID) at a MOI of 0.5 PFU for 2 h at room temperature. Unbound viral particles were removed and infected cells were incubated for 48 h. Hereafter viral RNA was isolated from the cell culture supernatant (150 µl) using the NucleoSpin® 96 Virus Kit [Macherey-Nagel] according to the vendor's manual. RNA was quantified by absorbance and 2.5 µg were reversely transcribed via RevertAid Reverse Transcriptase [Thermo] with RT-Primer [5'-GGTTTCCCAGCTTCTCCTGG-3'] (SEQ ID NO:5). 100 ng of reverse transcribed RNA were subjected to SYBR-green based quantitative RT-PCR using the LightCycler®480 with LightCycler®480 SYBR Green I Master [Roche] and a ZIKV-specific forward and reverse primer pair (5'-AAAAACCCCATGTGGAGAGG-3' (SEQ ID NO:6) and 5'-CATTCCTTCAGTGTGTCACC-3 (SEQ ID NO:7)', respectively). The absolute number of ZIKV-genome copy equivalents (GCE) was determined via standard curves generated from plasmids with known concentrations carrying the respective amplified fragment of the ZIKV genome. Values are ±SEM; n=4. LabyA1 ($IC_{50}$=4.6 µg/ml); LabyA2 ($IC_{50}$=5.4 µg/ml); combination LabyA1 and LabyA2 ($IC_{50}$=3.5 µg/ml).

Example 8: Effects of Labyrinthopeptins A1 and A2 on HCV Infection

Huh 7.5 Firefly luciferase expressing cells (Huh 7.5 Fluc) cells were seeded in 96 well plates ($10*10^3$ cells/well) and incubated overnight (18 hours approx) at 37° C. with 5% $CO_2$ supply. Huh 7.5 Fluc cells are a hepatoma cell line stably expressing firefly luciferase protein which is used to measure cell viability.

The following day, labyrinthopeptin at various concentrations was added to medium containing HCV JcR2a generated in culture (445.5 µL medium containing virus was transferred to 8 eppendorfs, each of which contained 4.5 µL compound at various concentrations to achieve desired final concentrations; i.e 50 µM, 25 µM etc) the 9th eppendorf, a positive control, contained DMSO solvent. A hepatitis C virus JcR2a reporter construct was used. (A genotype 2, starin A, chemiric construct which has a *Renilla* luciferase gene fused in frame its open reading frame. Viral genome translation and replication is relative to *Renilla* luciferase expression).

The virus/compound preparation was then inoculated to the cells, in duplicates, and incubated for 4 hours at 37° C. with 5% $CO_2$ supply. After 4 hours the medium containing virus/compound was aspirated from the cells following which cells were washed with sterile PBS, 200 µL per well, to removal any residual virus or compound.

The cells were replenished with 200 µL/well DMEM and incubated for 48 hours at 37° C. with 5% $CO_2$ supply. After 48 hours, the medium was aspirated from the wells and then the cells were washed twice with 200 µL PBS. Cells were then lysed with 1× passive lysis buffer and the lysate was analysed on a Berthold plate luminometer.

Virus entry into the cells was quantified by measuring *Renilla* luciferase expression. The read-outs from wells that were treated with compounds were normalized to the read-out from wells that were treated with DMSO control. A decrease in *Renilla* luciferase expression, with stable expression of firefly luciferase, is relative to ability of the compound to inhibit virus entry into the cells.

As can be seen from FIG. 20A, LabyA1 inhibits HCV virus entry with an IC50 of 1.05 µM and an IC90 of 9.163 µM. FIG. 20B shows that LabyA2 inhibits HCV virus entry with an IC50 of 1.728 µM and an IC90 of 24.9 µM. No cytotoxicity was observed at the tested LabyA1 and LabyA2 concentrations.

Example 9: Cell-Based High-Throughput Screening (HTS) System

A cell-based screening system was used to determine the cytotoxic concentration (CC50) of labyrinthopeptin A1 and A2.

$1 \times 10^4$ HEp-2 cells, which are stably expressing the reporter gene of a firefly luciferase (FF-luc), were seeded in a 96-well plate in 200 µl appropriate media. After 72 h of incubation at 37° C. in the presence of increasing concentrations of labyrinthopeptin A1 or A2 up to 100 µM, the cells have been lysed in 35 µl lysis buffer and the extinction of the FF-luc (RLU) was measured using a plate luminometer (Berthold). The number of surviving cells is indirectly proportional to residual luciferase expression.

The half maximal cytotoxic concentration (CC50) has been calculated for labyrinthopeptin A1 CC50=79.70 µM. There was no cytotoxic affect for labyrinthopeptin A2 detectable up to a concentration of 100 µM.

Example 10: Summary of Anti-Viral Effects of Labyrinthopeptins

Table 4 shows the IC50 values of the anti-viral activities of LabyA1, LabyA2, the combination of LabyA1 and LabyA2 (LabyA1/A2), the LabyA1 derivative "LabyA1-hexyn" (herein also called "LabyA1-Hexyn"), the LabyA2 derivative "LabyA2-hexyn" (herein also called "LabyA2-Hexyn"), as well as the combination of LabyA1-hexyn and LabyA2-hexyn (LabyA1/A2-hexyn).

TABLE 4

IC50 values (in μM and μg/ml) of the anti-viral activity of labyrinthopeptins, combinations of labyrinthopeptins and labyrinthopeptin derivatives.

| | LabyA1 | | LabyA2 | | LabyA1/A2 | | LabyA1-hexyn | | LabyA2-hexyn | | LabyA1/A2 - hexyn | |
|---|---|---|---|---|---|---|---|---|---|---|---|---|
| | μM | μg/ml | μM | μg/ml | μM | μg/ml | μM | μg/ml | μM | μg/m | μM | μg/ml |
| DENV | 1.78 | 3.7 | 8.00 | 15.4 | 1.30 | 2.6 | 1.70 | 3.7 | 7.03 | 14.2 | 0.96 | 2.0 |
| RSV | 0.39[1] | 0.8[1] | 4.97[1] | 9.56[1] | — | — | — | — | — | — | — | — |
| KSHV | 2 | 4.2 | 15 | 28.9 | — | — | — | — | — | — | — | — |
| TBEV | 24.10 | 50 | >25.99 | >50 | 8.34 | 16.67 | — | — | — | — | — | — |
| CMV | 1.3 | 2.7 | 5.4 μM | 10.4 | — | — | — | — | — | — | — | — |
| CHIKV | 0.5-1.7 | 1.0-3.5 | — | — | — | — | — | — | — | — | — | — |
| VSV | 1.1-3.7 | 2.3-7.7 | — | — | — | — | — | — | — | — | — | — |
| ZIKV | 2.22 | 4.6 | 2.81 | 5.4 | 1.75 | 3.5 | — | — | — | — | — | — |
| HCV | 1.05 | 2.18 | 1.728 | 3.32 | — | — | — | — | — | — | — | — |

LabyA1 = 2075.33 g/mol    LabyA2 = 1924.16 g/mol    LabyA1-hexyn = 2170.45 g/mol    LabyA2-hexyn = 2019.28 g/mol

[1]These values are measured by intracellular RSV-P staining (see FIG. 16C).

The present invention refers to the following amino acid sequences:

SEQ ID NO: 1: Amino acid sequence of the labyrinthopeptin of the present invention
SEQ ID NO: 2: Amino acid sequence of the labyrinthopeptin derivative of the present invention
SEQ ID NO: 3: Amino acid sequence of LabyA1
SEQ ID NO: 4: Amino acid sequence of LabyA2
SEQ ID NO: 5: RT-Primer
5'-GGTTTCCCAGCTTCTCCTGG-3'

SEQ ID NO: 6: ZIKV-specific forward primer
5'-AAAAACCCCATGTGGAGAGG-3'

SEQ ID NO: 7: ZIKV-specific reverse primer
5'-CATTCCTTCAGTGTGTCACC-3'

The invention claimed is:

1. A method of treating and/or preventing an infection with any one of the viruses selected from the group consisting of respiratory syncytial virus (RSV), Kaposi sarcoma-associated herpesvirus (KSHV), cytomegalovirus (CMV), chikungunya virus (CHIKV), tick-borne encephalitis virus (TBEV), vesicular stomatitis Indiana virus (VSV), and zika virus (ZIKV) in a subject in need thereof, wherein the method comprises administering an effective dose of a peptide to the subject, and wherein said peptide comprises the amino acid sequence (SEQ ID NO: 2)

Lab-$X_1$—$X_2$-Lab-$X_3$—$X_4$—$X_5$-Lab-Cys-Lab-$X_6$—$X_7$-Lab-$X_8$-Lab-Cys, (with CH$_2$ bridges and S—S disulfide bonds as shown)

wherein:
Lab is labionin;
$X_1$ is Asn or Asp;
$X_2$ is Ala or Trp;
$X_3$ is Val or Leu;
$X_4$ is Trp;
$X_5$ is Glu;
$X_6$ is Thr;
$X_7$ is Gly; and
$X_8$ consists of the amino acid sequence Trp-Val-Pro-Phe-dehydrobutyrine (SEQ ID NO:8), or the amino acid sequence Leu-Phe-Ala.

2. The method of claim 1, wherein said peptide is maximal 30 amino acids in length.

3. The method of claim 1, wherein
$X_1$ is Asn;
$X_2$ is Ala;
$X_3$ is Val;
$X_4$ is Trp;
$X_5$ is Glu;
$X_6$ is Thr;
$X_7$ is Gly; and
$X_8$ consists of the amino acid sequence Trp-Val-Pro-Phe-dehydrobutyrine (SEQ ID NO:8).

4. The method of claim 1, wherein
$X_1$ is Asp;
$X_2$ is Trp;
$X_3$ is Leu;
$X_4$ is Trp;
$X_5$ is Glu;
$X_6$ is Thr;
$X_7$ is Gly; and
$X_8$ consists of the amino acid sequence Leu-Phe-Ala.

5. The method of claim 1, wherein the method further comprises co-administration with at least one other active agent.

6. The method of claim 5, wherein the other active agent is a CMV inhibitor, a KSHV inhibitor, a RSV inhibitor, a dengue virus (DENV) inhibitor, a CHIKV inhibitor, a TBEV inhibitor, a VSV inhibitor, a ZIKV inhibitor, or a HCV inhibitor.

7. The method of claim 1, wherein the peptide is administered orally, intravenously, subcutaneously or intramuscularly.

8. The method of claim 1, wherein the virus is RSV.

9. The method of claim 3, wherein the method further comprises administering to the subject and effective dose of a second peptide comprising the amino acid sequence (SEQ ID NO: 2)

```
          CH₂              S─────────S
         /                 |    CH₂   |
Lab-X₁-X₂-Lab-X₃-X₄-X₅-Lab-Cys-Lab-X₆-X₇-Lab-X₈-Lab-Cys.
           \              /        \
            S            S
``` wherein:

$X_1$ is Asp;
$X_2$ is Trp;
$X_3$ is Leu;
$X_4$ is Trp;
$X_5$ is Glu;
$X_6$ is Thr;
$X_7$ is Gly; and
$X_8$ consists of the amino acid sequence Leu-Phe-Ala.

10. The method of claim 9, wherein the method further comprises co-administration with at least one other active agent.

11. The method of claim 10, wherein the other active agent is a CMV inhibitor, a KSHV inhibitor, a RSV inhibitor, a DENV inhibitor, a CHIKV inhibitor, a TBEV inhibitor, a VSV inhibitor, a ZIKV inhibitor, or a HCV inhibitor.

12. The method of claim 9, wherein the combination is administered orally, intravenously, subcutaneously or intramuscularly.

13. The method of claim 9, wherein the virus is RSV.

* * * * *